United States Patent
Westberg et al.

(10) Patent No.: US 6,322,488 B1
(45) Date of Patent: Nov. 27, 2001

(54) BLOOD SEPARATION CHAMBER WITH PREFORMED BLOOD FLOW PASSAGES AND CENTRALIZED CONNECTION TO EXTERNAL TUBING

(75) Inventors: Tom Westberg; Kelly B Smith, both of Gurnee; Sanjay V. Odak, Grayslake, all of IL (US); Michel L. F. Joie, Ernage; Georges E Rondeau, Braffe, both of (BE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/389,938

(22) Filed: Sep. 3, 1999

(51) Int. Cl.[7] .................................................. B04B 7/08
(52) U.S. Cl. ............................................ 494/43; 494/39
(58) Field of Search ................................ 210/782, 787, 210/789, 512.1, 232; 494/43, 45, 39, 41, 47

(56) References Cited

U.S. PATENT DOCUMENTS

| | | |
|---|---|---|
| 1,647,292 | 11/1927 | Hill . |
| 3,666,170 | 5/1972 | Cacciabue et al. . |
| 3,785,549 | 1/1974 | Latham, Jr. . |
| 4,091,989 * | 5/1978 | Schultz . |
| 4,109,854 | 8/1978 | Brown . |
| 4,120,448 | 10/1978 | Cullis . |
| 4,146,172 | 3/1979 | Cullis et al. . |
| 4,164,318 | 8/1979 | Boggs . |
| 4,278,202 | 7/1981 | Westberg . |
| 4,389,206 | 6/1983 | Bacehowski ............................ 494/42 |
| 4,708,712 * | 11/1987 | Mulzet ................................... 494/45 |
| 4,734,089 | 3/1988 | Cullis ..................................... 494/27 |
| 4,834,890 | 5/1989 | Brown et al. ......................... 210/739 |
| 5,078,671 | 1/1992 | Dennehey et al. ..................... 494/27 |
| 5,308,309 | 5/1994 | Morris ................................... 494/85 |
| 5,350,514 | 9/1994 | Witthaus et al. ...................... 494/18 |
| 5,362,291 | 11/1994 | Williamson, IV .................... 494/18 |
| 5,370,802 | 12/1994 | Brown .................................. 210/782 |
| 5,386,734 | 2/1995 | Pusinelli .............................. 210/782 |
| 5,387,174 | 2/1995 | Rochat ................................... 494/10 |
| 5,462,416 | 10/1995 | Dennehey et al. ................... 604/153 |
| 5,494,592 | 2/1996 | Latham, Jr. et al. ................ 210/782 |
| 5,529,567 | 6/1996 | Toth et al. ............................... 494/7 |
| 5,549,834 | 8/1996 | Brown .................................. 210/782 |
| 5,571,068 | 11/1996 | Bacehowski et al. ................. 494/45 |
| 5,581,687 | 12/1996 | Lyle et al. ............................. 395/326 |
| 5,643,193 | 7/1997 | Papillon et al. ......................... 604/6 |
| 5,651,766 | 7/1997 | Kingsley et al. .................... 210/782 |
| 5,658,231 | 8/1997 | Schmitt et al. ........................ 494/12 |
| 5,720,716 | 2/1998 | Blakeslee et al. ..................... 494/45 |
| 5,750,025 | 5/1998 | Holmes et al. ...................... 210/782 |
| 5,769,811 | 6/1998 | Stacey et al. ........................ 604/407 |
| 5,792,038 | 8/1998 | Hlavinka ............................... 494/45 |
| 5,833,866 | 11/1998 | Brown .................................. 210/739 |
| 5,837,150 * | 11/1998 | Langley et al. ..................... 210/782 |
| 5,906,598 * | 5/1999 | Giesler et al. ....................... 210/787 |
| 5,939,319 | 8/1999 | Hlavinka ............................. 210/782 |
| 5,964,690 | 10/1999 | Wright et al. ......................... 494/12 |
| 5,980,757 | 11/1999 | Brown et al. ....................... 210/745 |
| 5,980,760 | 11/1999 | Min et al. ........................... 210/782 |
| 5,989,177 | 11/1999 | West et al. ............................ 494/46 |
| 6,027,657 | 2/2000 | Min et al. ........................... 210/782 |
| 6,053,856 | 4/2000 | Hlvainka .............................. 494/37 |

FOREIGN PATENT DOCUMENTS

| | | |
|---|---|---|
| 19706997 | 8/1998 | (DE) . |
| WO8900084 | 1/1989 | (WO) . |
| WO9822165 | 5/1998 | (WO) . |
| WO9848938 | 11/1998 | (WO) . |

* cited by examiner

Primary Examiner—John Kim
(74) Attorney, Agent, or Firm—Daniel D. Ryan; Bradford R. L. Price; Amy L. H. Rockwell

(57) ABSTRACT

A blood separation chamber comprises a base that includes formed walls that define a hub. A separation channel extends about the hub. A flow passage extends between the hub and the separation channel. The hub enables attachment of external tubing to convey blood to and from the separation channel through the hub.

30 Claims, 41 Drawing Sheets

FIG 16
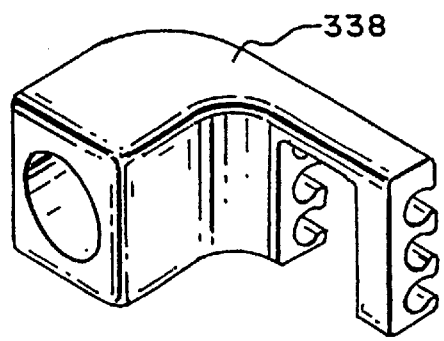
FIG. 17
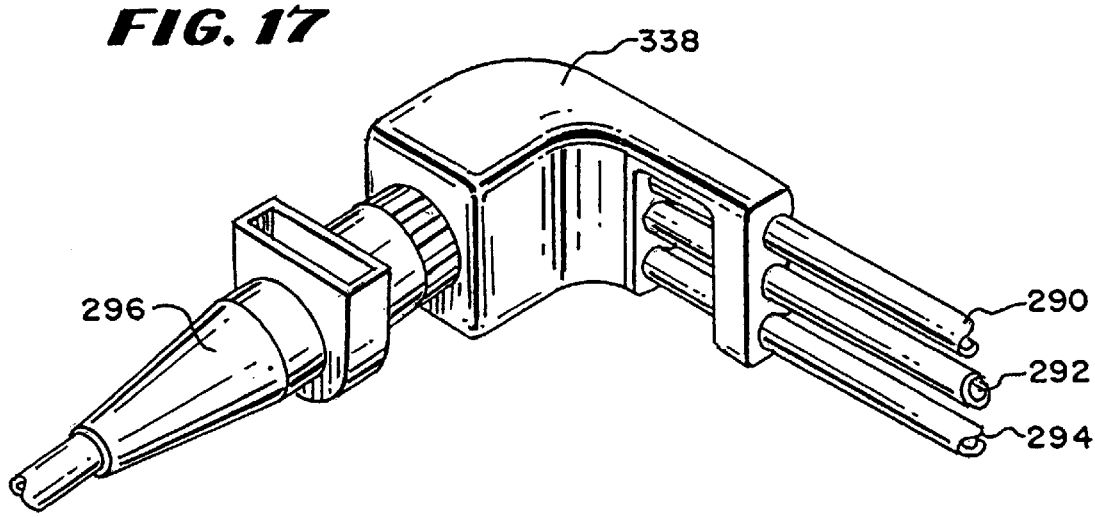
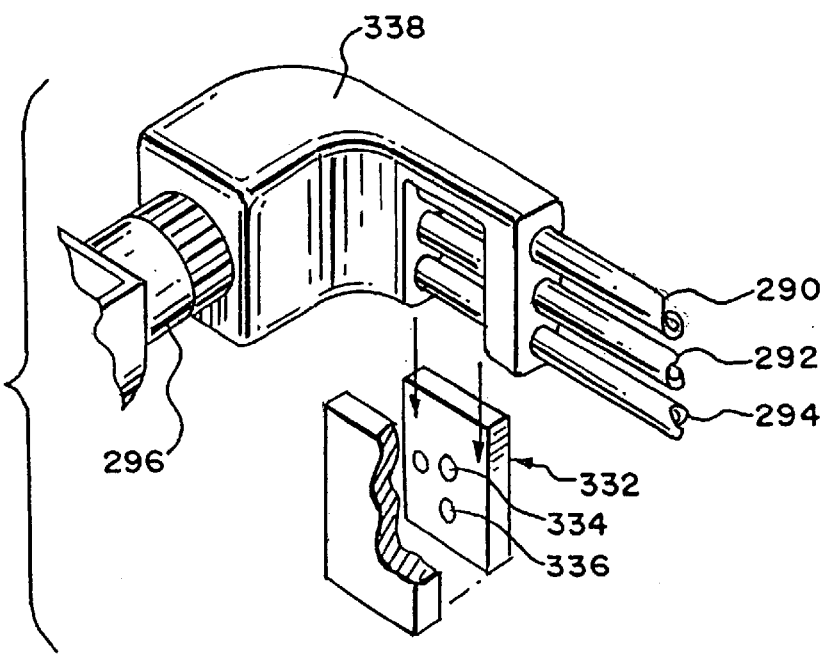
FIG. 18

FIG. 23
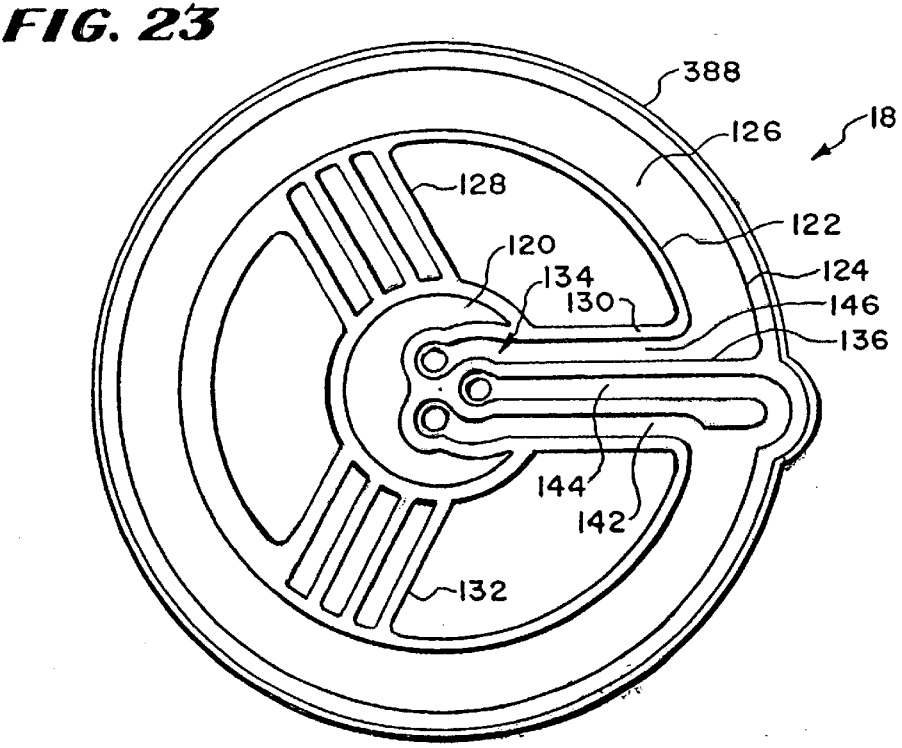
FIG. 24
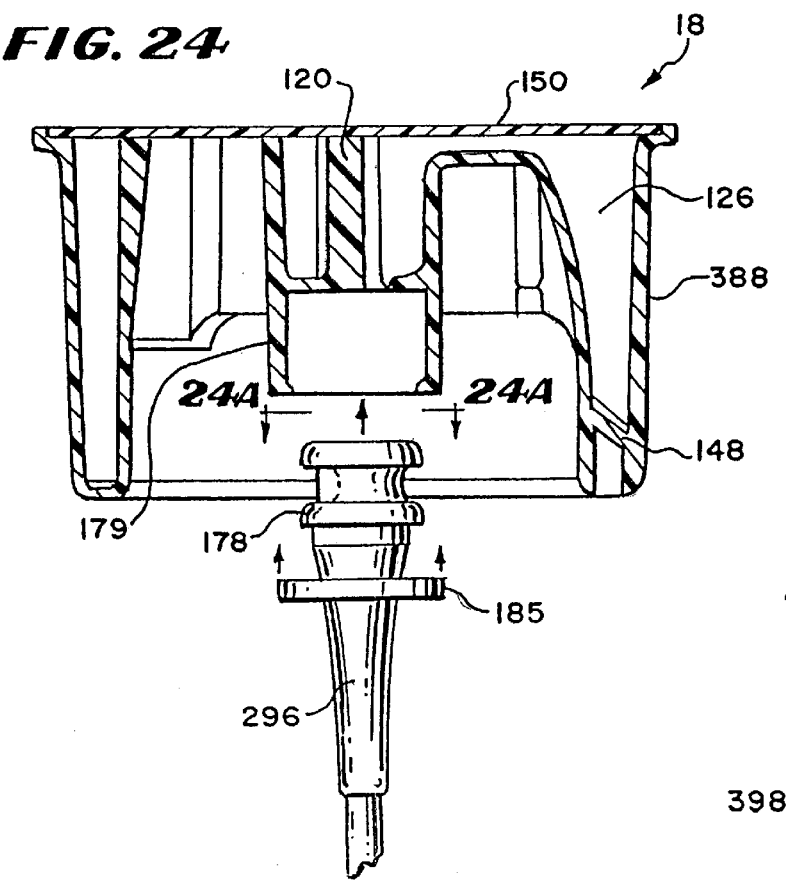
FIG. 24A

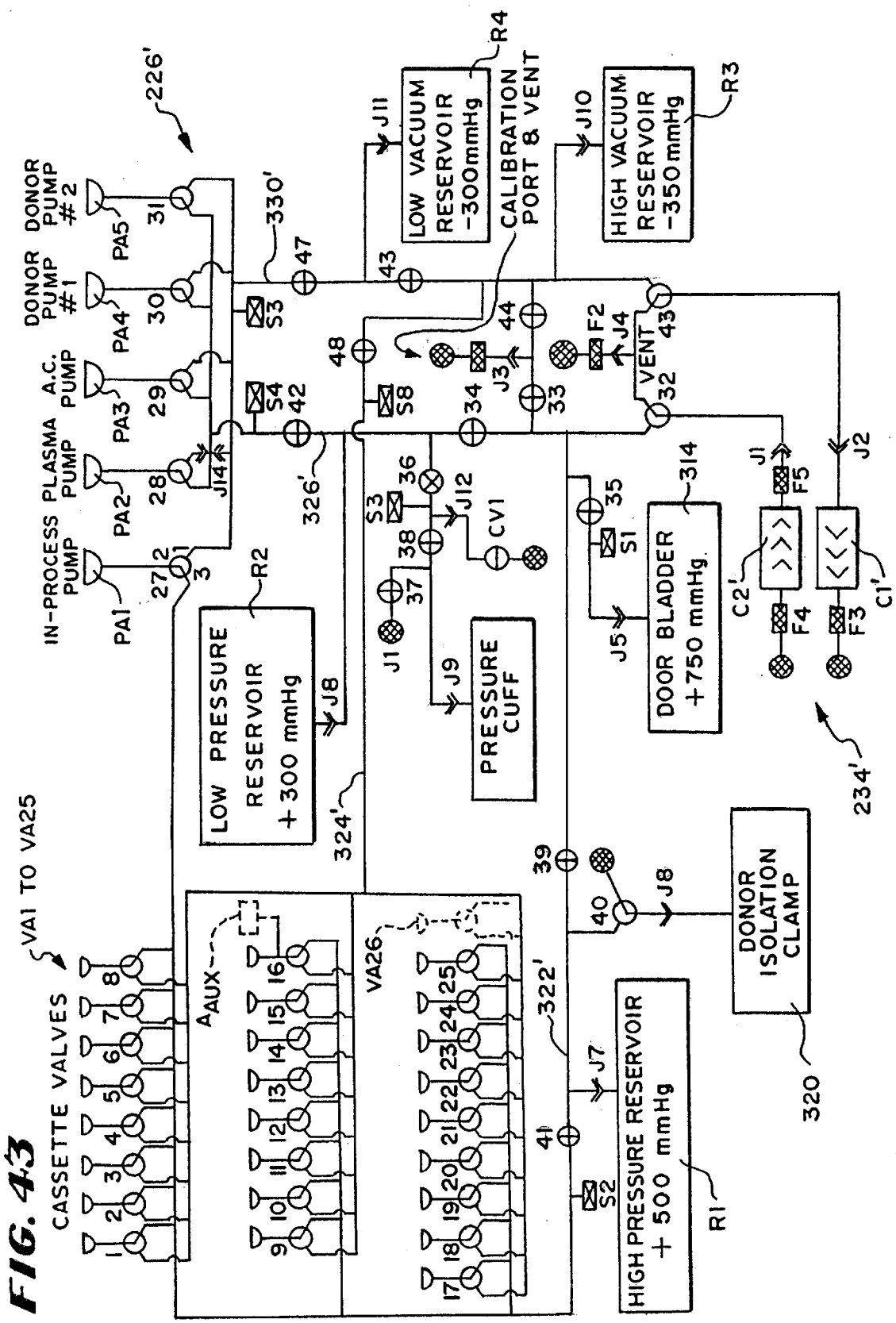

BLOOD SEPARATION CHAMBER WITH PREFORMED BLOOD FLOW PASSAGES AND CENTRALIZED CONNECTION TO EXTERNAL TUBING

FIELD OF THE INVENTION

This invention relates to systems and methods for processing and collecting blood, blood constituents, or other suspensions of cellular material.

BACKGROUND OF THE INVENTION

Today people routinely separate whole blood, usually by centrifugation, into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Conventional blood centrifuges are of a size that does not permit easy transport between collection sites. Furthermore, loading and unloading operations can sometimes be time consuming and tedious.

In addition, a need exists for further improved systems and methods for collecting blood components in a way that lends itself to use in high volume, on line blood collection environments, where higher yields of critically needed cellular blood components, like plasma, red blood cells, and platelets, can be realized in reasonable short processing times.

The operational and performance demands upon such fluid processing systems become more complex and sophisticated, even as the demand for smaller and more portable systems intensifies. The need therefore exists for automated blood processing controllers that can gather and generate more detailed information and control signals to aid the operator in maximizing processing and separation efficiencies.

SUMMARY OF THE INVENTION

The invention provides systems and methods for processing blood and blood constituents that lend themselves to portable, flexible processing platforms equipped with straightforward and accurate control functions.

More particularly, the invention provides a compact blood separation chamber comprising a base that includes formed walls that define a hub. A separation channel extends about the hub. A flow passage extends between the hub and the separation channel. The hub enables attachment of external tubing to convey blood to and from the separation channel through the hub.

According to one aspect of the invention, the blood separation chamber comprises a formed body, which, in use, rotates about a rotational axis. A first interior wall is formed on the body, which extends circumferentially about the rotational axis to define the hub. Inside and outside walls are also formed on the body, which extend circumferentially about the hub in a spaced apart relationship to define between them the separation channel. Second interior walls are formed on the body, which extend radially from the hub in a spaced apart relationship to define between them at least one passage that communicates with the separation channel to direct blood between the hub and the separation channel. A connector is formed on the body to couple exterior tubing to the hub in communication with the passage to convey blood to or from the passage during rotation of the formed base.

Various interior wall structures can be provided on the body to enhance blood flow and separation within the chamber.

In one embodiment, the second interior walls define an inlet passage to direct blood from the hub into the separation channel and an outlet passage to direct blood from the separation channel to the hub.

In one embodiment, an interior wall is formed on the body, which extends across the separation channel to define a terminus in the separation channel. In this arrangement, the second interior walls can define a first passage communicating with the separation channel on one side of the terminus and a second passage communicating with the separation channel on an opposite side of the terminus.

In one embodiment, a interior wall formed on the body extends partially into the separation channel to define a dam in the separation channel. In this arrangement, the formed second interior walls define a first passage communicating with the separation channel on one side of the dam and a second passage communicating with the separation channel on an opposite side of the dam. In one embodiment, the dam projects from the inside wall toward the outside wall to form a constricted channel along the outside wall. In one arrangement, the constricted channel includes a recess in the outside wall radially spaced from the rotational axis farther than adjacent regions of the formed outside wall.

According to another aspect of the invention, an umbilicus includes an umbilicus connector that is shaped to releasably mate with a connector on the hub, to couple the umbilicus to the blood separation chamber.

Another aspect of the invention provides a blood separation chamber for use in a blood centrifuge of the type that rotates an umbilicus in concert with a centrifuge rotor to prevent twisting of the umbilicus. The blood separation chamber comprises a unitary base including formed walls that define a hub. A separation channel extends about the hub. A flow passage that extends between the hub and the separation channel. The hub enables attachment of the umbilicus to convey blood to and from the separation channel through the hub. A lid covers the base and closes the separation channel on a side opposite to the hub. The lid is formed to enable releasable attachment of the blood processing chamber as a unit to the centrifuge rotor for rotation to separate blood in the separation channel.

Other features and advantages of the inventions are set forth in the following specification and attached drawings.

BRIEF DESCRIPTION OF THE DRAWINGS

FIG. 16 is a perspective view of a fixture that, when coupled to the plasma and red blood cell collection tubes hold the tubes in a desired viewing alignment with the in-line sensors, as shown in FIGS. 15A, 15B, and 15C;

FIG. 17 is a perspective view of the fixture shown in FIG. 16, with a plasma cell collection tube, a red blood cell collection tube, and a whole blood inlet tube attached, gathering the tubes in an organized, side-by-side array;

FIG. 18 is a perspective view of the fixture and tubes shown in FIG. 17, as being placed into viewing alignment with the two sensors shown in FIGS. 15A, 15B, and 15C;

FIG. 23 is a top view of the molded processing container shown in FIG. 21;

FIG. 24 is a side section view of the molded processing container shown in FIG. 21, showing an umbilicus to be connected the container;

FIG. 24A is a top view of the connector that connects the umbilicus to the molded processing container in the manner shown in FIG. 24, taken generally along line 24A—24A in FIG. 24;

FIG. 43 is a schematic view of a pneumatic manifold assembly, which is part of the pump and valve station shown in FIG. 6, and which supplies positive and negative pneumatic pressures to convey fluid through the cassette shown in FIGS. 35 and 36.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
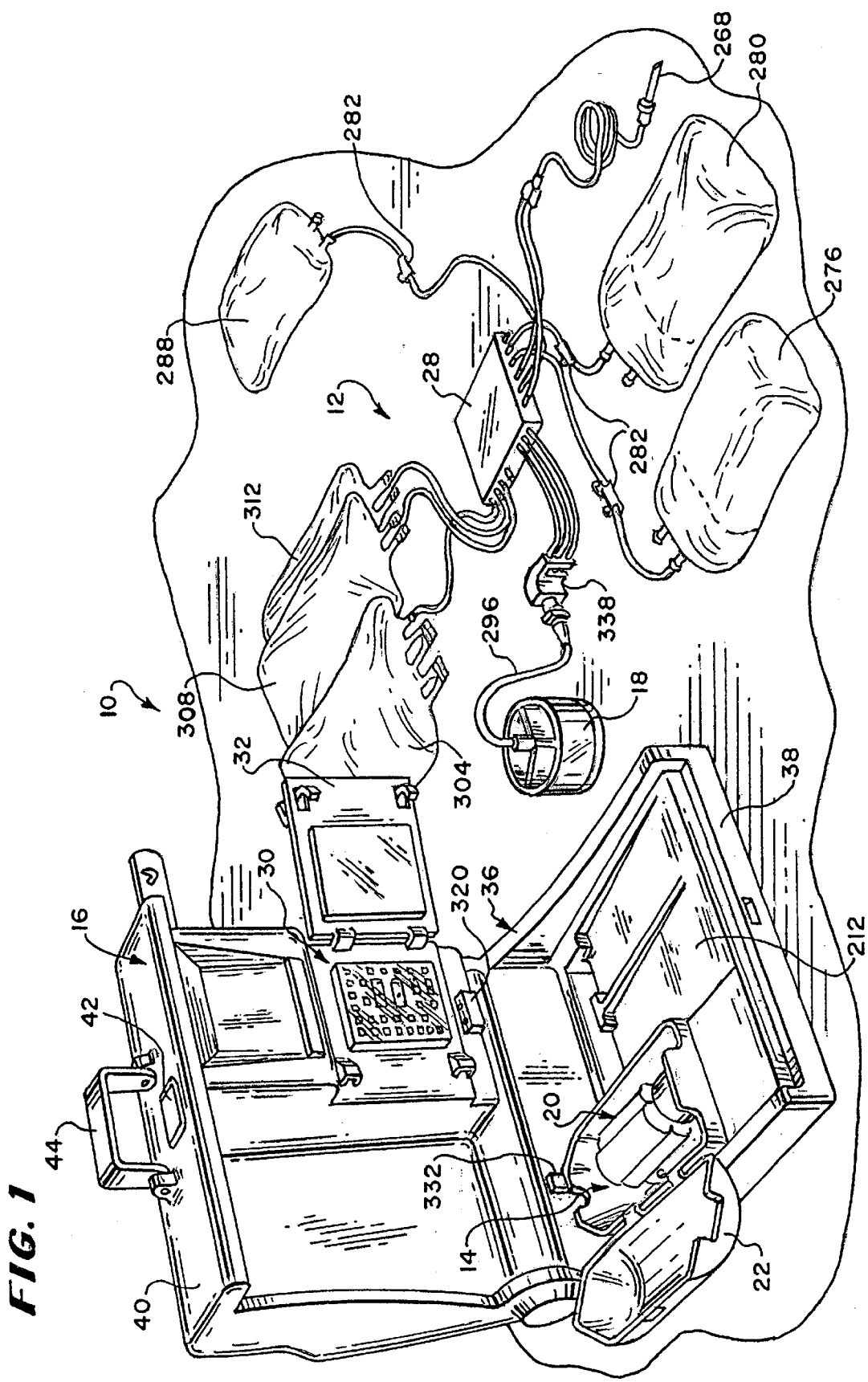
FIG. 1 is a perspective view of a system that embodies features of the invention, with the disposable processing set shown out of association with the processing device prior to use.

FIG. 1 shows a fluid processing system 10 that embodies the features of the invention. The system 10 can be used for processing various fluids. The system 10 is particularly well suited for processing whole blood and other suspensions of biological cellular materials. Accordingly, the illustrated embodiment shows the system 10 used for this purpose.

I. System Overview

The system 10 includes three principal components. These are (i) a liquid and blood flow set 12; (ii) a blood processing device 14 that interacts with the flow set 12 to cause separation and collection of one or more blood components; and (iii) a controller 16 that governs the interaction to perform a blood processing and collection procedure selected by the operator.

The blood processing device 14 and controller 16 are intended to be durable items capable of long term use. In the illustrated and preferred embodiment, the blood processing device 14 and controller 16 are mounted inside a portable housing or case 36. The case 36 presents a compact footprint, suited for set up and operation upon a table top or other relatively small surface. The case 36 is also intended to be transported easily to a collection site.

Figure 4:
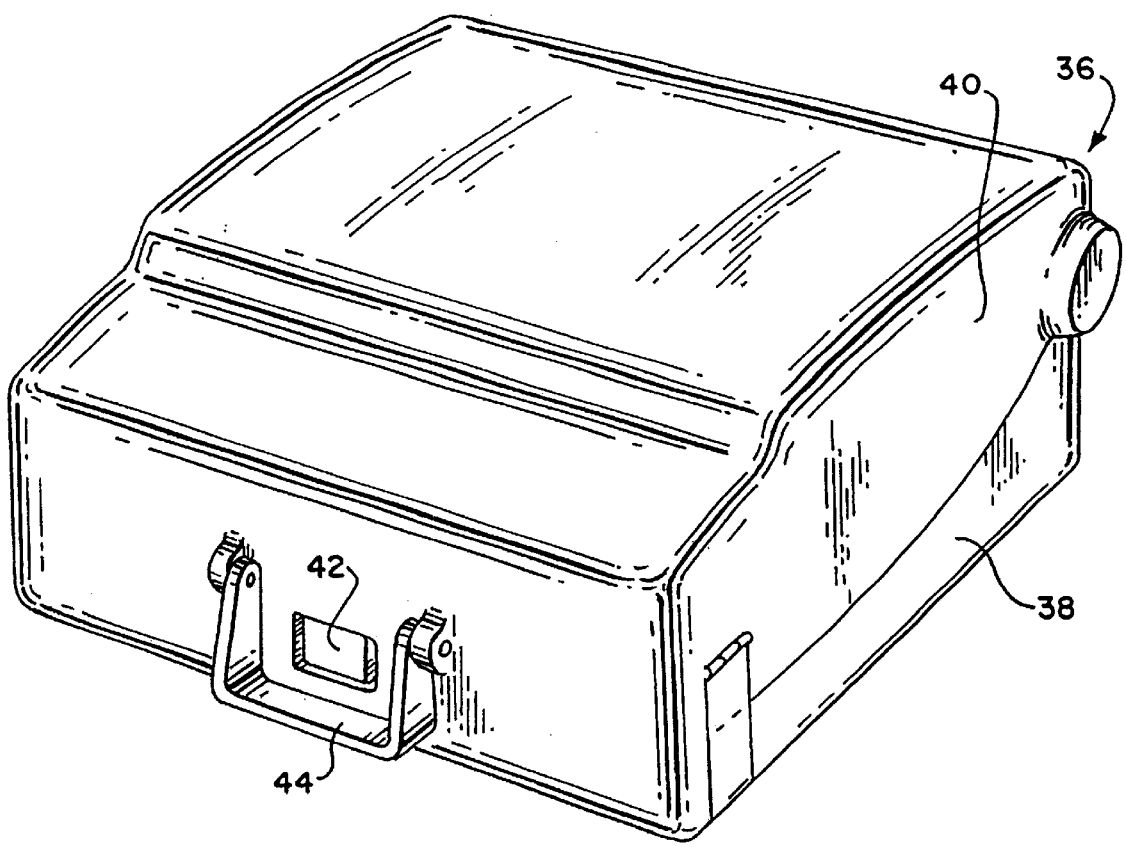
FIG. 4 is a right perspective front view of the case that houses the processing device shown in FIG. 1, with the lid closed for transporting the device.

The case 36 includes a base 38 and a hinged lid 40, which opens (as FIG. 1 shows) and closes (as FIG. 4 shows). The lid 40 includes a latch 42, for releasably locking the lid 40 closed. The lid 40 also includes a handle 44, which the operator can grasp for transporting the case 36 when the lid 40 is closed. In use, the base 38 is intended to rest in a generally horizontal support surface.

The case 36 can be formed into a desired configuration, e.g., by molding. The case 36 is preferably made from a lightweight, yet durable, plastic material.

Figure 2:
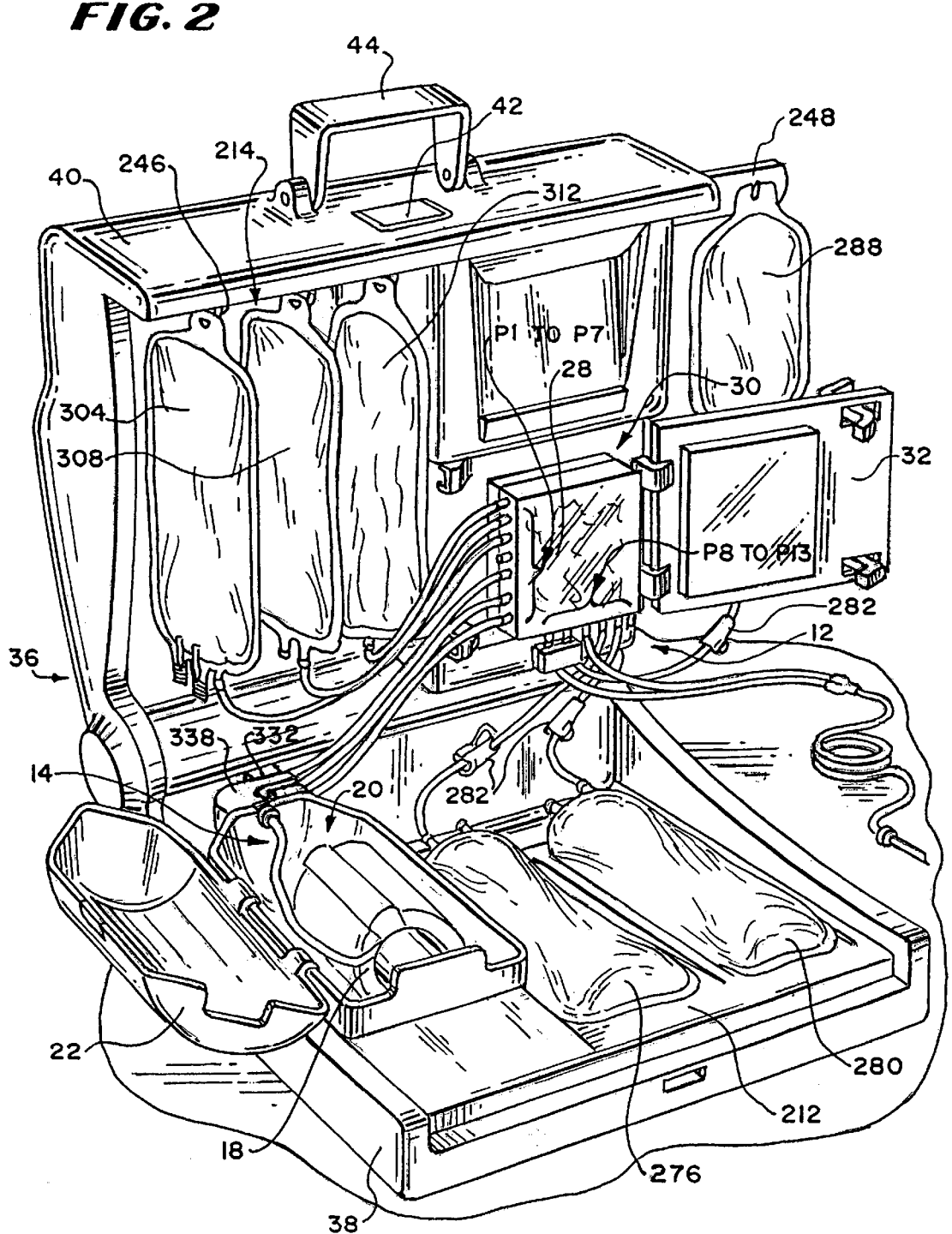
FIG. 2 is a perspective view of the system shown in FIG. 1, with the doors to the centrifuge station and pump and valve station being shown open to accommodate mounting of the processing set.

The flow set 12 is intended to be a sterile, single use, disposable item. As FIG. 2 shows, before beginning a given blood processing and collection procedure, the operator loads various components of the flow set 12 in the case 36 in association with the device 14. The controller 16 implements the procedure based upon preset protocols, taking into account other input from the operator. Upon completing the procedure, the operator removes the flow set 12 from association with the device 14. The portion of the set 12 holding the collected blood component or components are removed from the case 36 and retained for storage, transfusion, or further processing. The remainder of the set 12 is removed from the case 36 and discarded.

Figure 3:
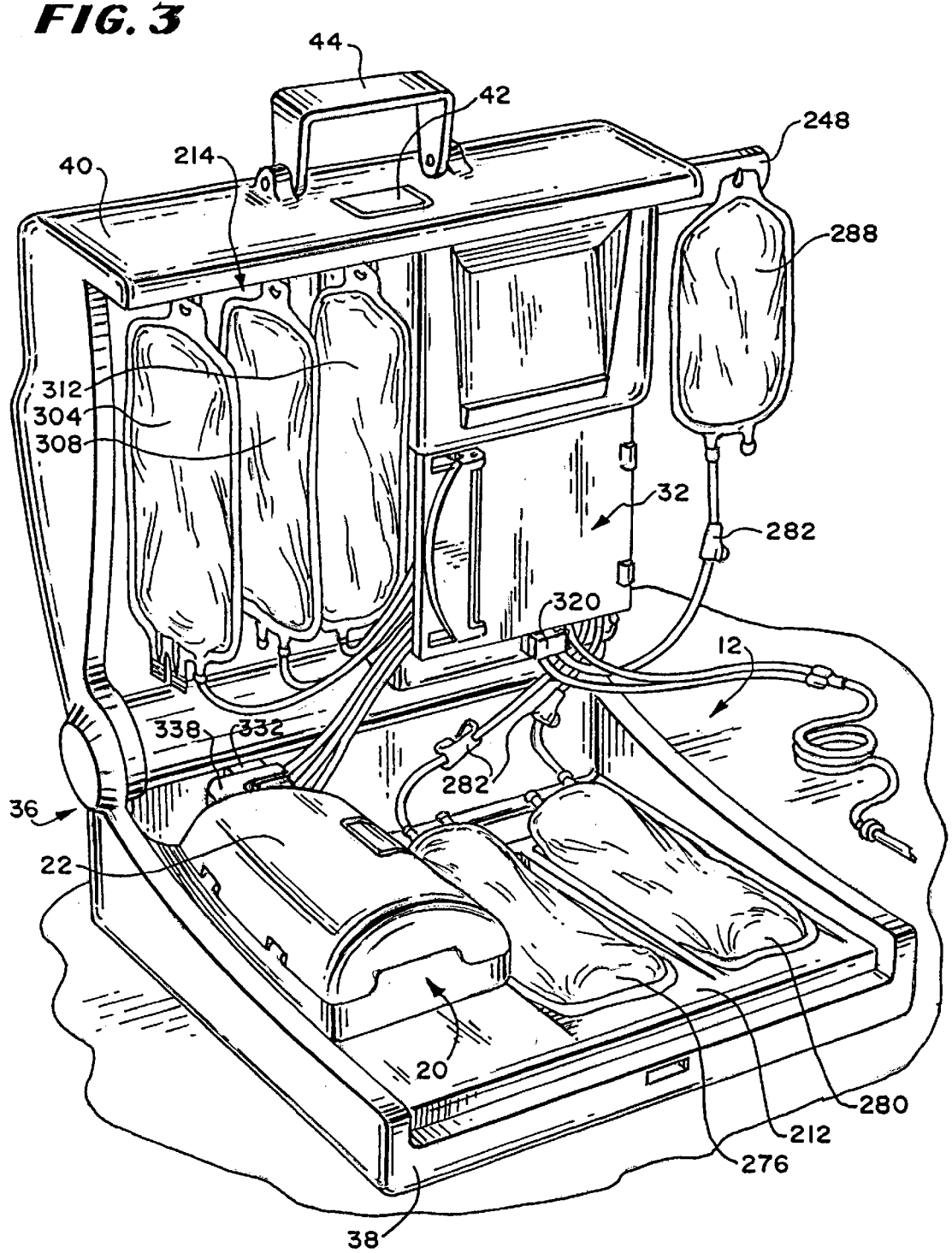
FIG. 3 is a perspective view of the system shown in FIG. 1 with the processing set fully mounted on the processing device and ready for use.

The flow set 12 shown in FIG. 1 includes a blood processing chamber 18 designed for use in association with a centrifuge. Accordingly, as FIG. 2 shows, the processing device 14 includes a centrifuge station 20, which receives the processing chamber 18 for use. As FIGS. 2 and 3 show, the centrifuge station 20 comprises a compartment formed in the base 38. The centrifuge station 20 includes a door 22, which opens and closes the compartment. The door 22 opens to allow loading of the processing chamber 18. The door 22 closes to enclose the processing chamber 18 during operation.

The centrifuge station 20 rotates the processing chamber 18. When rotated, the processing chamber 18 centrifugally separates whole blood received from a donor into component parts, e.g., red blood cells, plasma, and buffy coat comprising platelets and leukocytes.

It should also be appreciated that the system 10 need not separate blood centrifugally. The system 10 can accommodate other types of blood separation devices, e.g., a membrane blood separation device.

II. The Programmable Blood Processing Circuit

Figure 5:
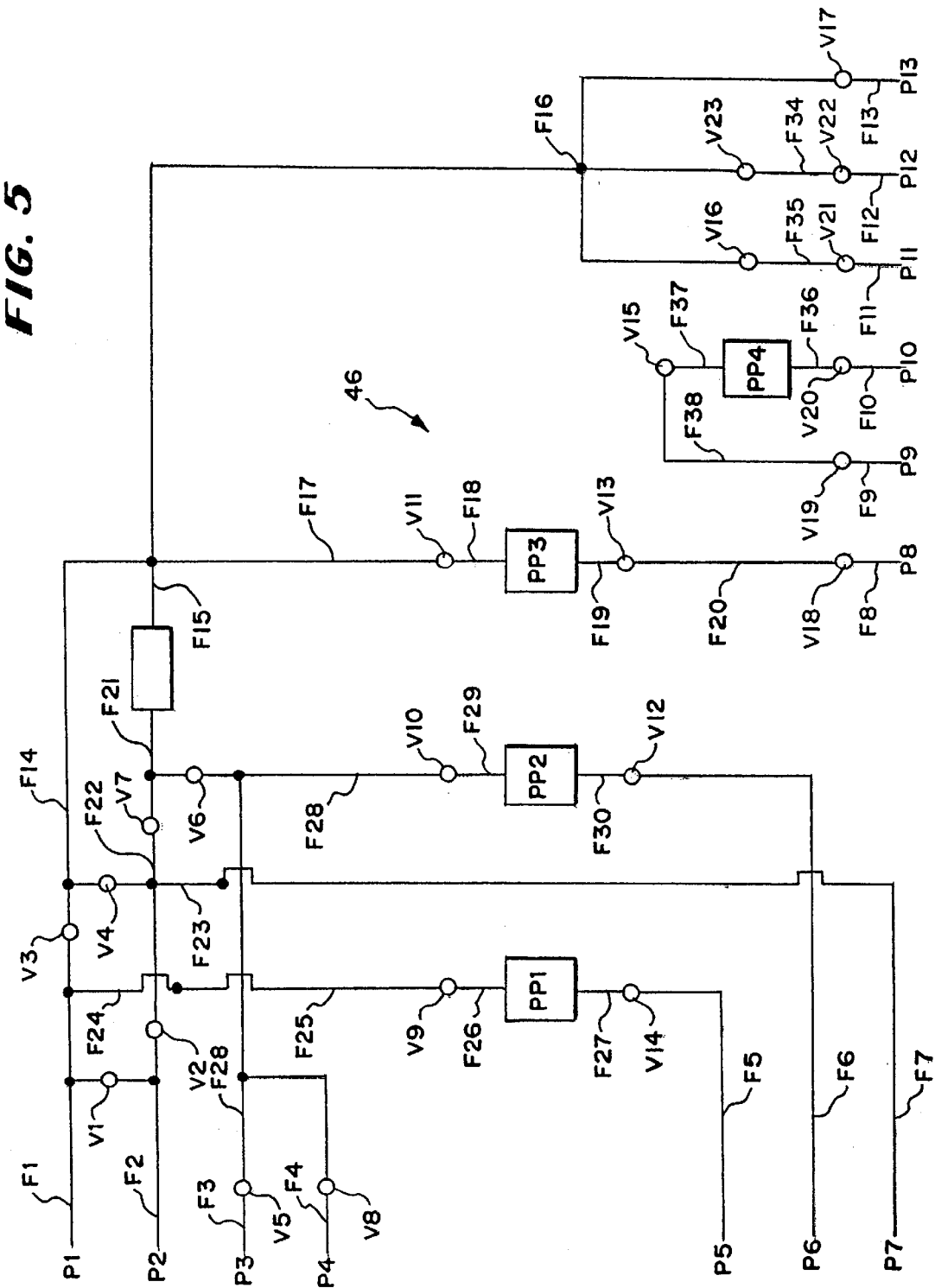
FIG. 5 is a schematic view of a blood processing circuit, which can be programmed to perform a variety of different blood processing procedures in association with the device shown in FIG. 1.
Figure 34:
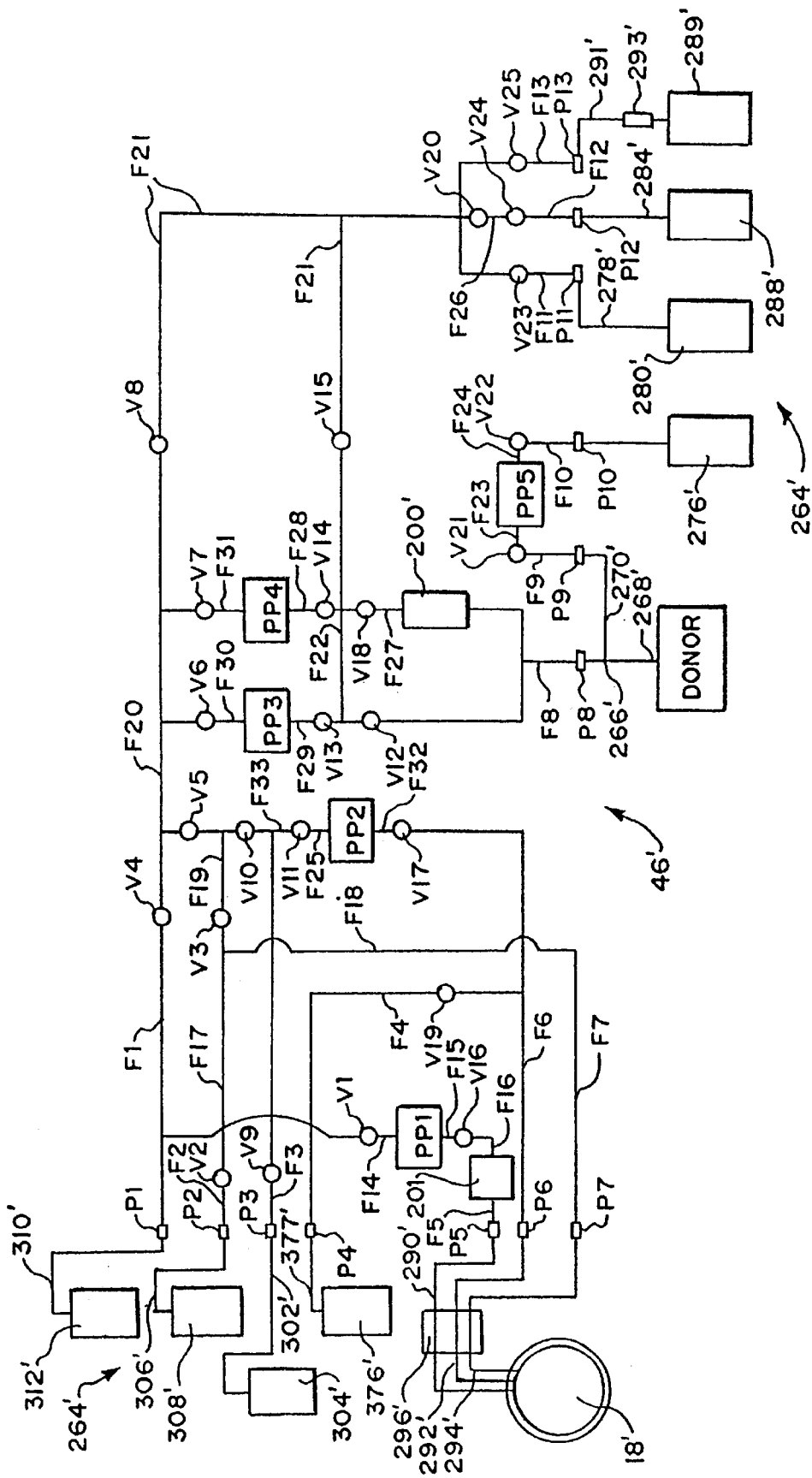
FIG. 34 is a schematic view of another blood processing circuit, which can be programmed to perform a variety of different blood processing procedures in association with the device shown in FIG. 1.

The set 12 defines a programmable blood processing circuit 46. Various configurations are possible. FIG. 5 schematically shows one representative configuration. FIG. 34 schematically shows another representative configuration, which will be described later.

Referring to FIG. 5, the circuit 46 can be programmed to perform a variety of different blood processing procedures in which, e.g., red blood cells are collected, or plasma is collected, or both plasma and red blood cells are collected, or the buffy coat is collected.

The circuit 46 includes several pump stations PP(N), which are interconnected by a pattern of fluid flow paths F(N) through an array of in line valves V(N). The circuit is coupled to the remainder of the blood processing set by ports P(N).

The circuit 46 includes a programmable network of flow paths, comprising eleven universal ports P1 to P8 and P11 to P13 and three universal pump stations PP1, PP2, and PP3. By selective operation of the in line valves V1 to V14, V16 to V18, and V21 to 23, any universal port P1 to P8 and P11 to P13 can be placed in flow communication with any universal pump station PP1, PP2, and PP3. By selective operation of the universal valves, fluid flow can be directed through any universal pump station in a forward direction or reverse direction between two valves, or an in-out direction through a single valve.

In the illustrated embodiment, the circuit also includes an isolated flow path comprising two ports P9 and P10 and one pump station PP4. The flow path is termed "isolated," because it cannot be placed into direct flow communication with any other flow path in the circuit 46 without exterior tubing. By selective operation of the in line valves V15, V19, and V20, fluid flow can be directed through the pump station in a forward direction or reverse direction between two valves, or an in-out direction through a single valve.

The circuit 46 can be programmed to assigned dedicated pumping functions to the various pump stations. For example, in a preferrred embodiment, the universal pump station PP3 can serve as a general purpose, donor interface pump, regardless of the particular blood procedure performed, to either draw blood from the donor or return blood to the donor through the port P8. In this arrangement, the pump station PP4 can serve as a dedicated anticoagulant pump, to draw anticoagulant from a source through the port P10 and to meter anticoagulant into the blood through port P9.

In this arrangement, the universal pump station PP1 can serve, regardless of the particular blood processing procedure performed, as a dedicated in-process whole blood pump, to convey whole blood into the blood separator. This dedicated function frees the donor interface pump PP3 from the added function of supplying whole blood to the blood separator. Thus, the in-process whole blood pump PP1 can maintain a continuous supply of blood to the blood separator, while the donor interface pump PP3 is simultaneously used to draw and return blood to the donor through the single phlebotomy needle. Processing time is thereby minimized.

In this arrangement, the universal pump station PP2 can serve, regardless of the particular blood processing procedure performed, as a plasma pump, to convey plasma from the blood separator. The ability to dedicate separate pumping functions provides a continuous flow of blood into and out of the separator, as well as to and from the donor.

The circuit 46 can be programmed, depending upon the objectives of the particular blood processing procedure, to retain all or some of the plasma for storage or fractionation purposes, or to return all or some of the plasma to the donor. The circuit 46 can be further programmed, depending upon the objectives of the particular blood processing procedure, to retain all or some of the red blood cells for storage, or to return all or some of the red blood cells to the donor. The circuit 46 can also be programmed, depending upon the objectives of the particular blood processing procedure, to retain all or some of the buffy coat for storage, or to return all or some of the buffy coat to the donor.

Figure 6:
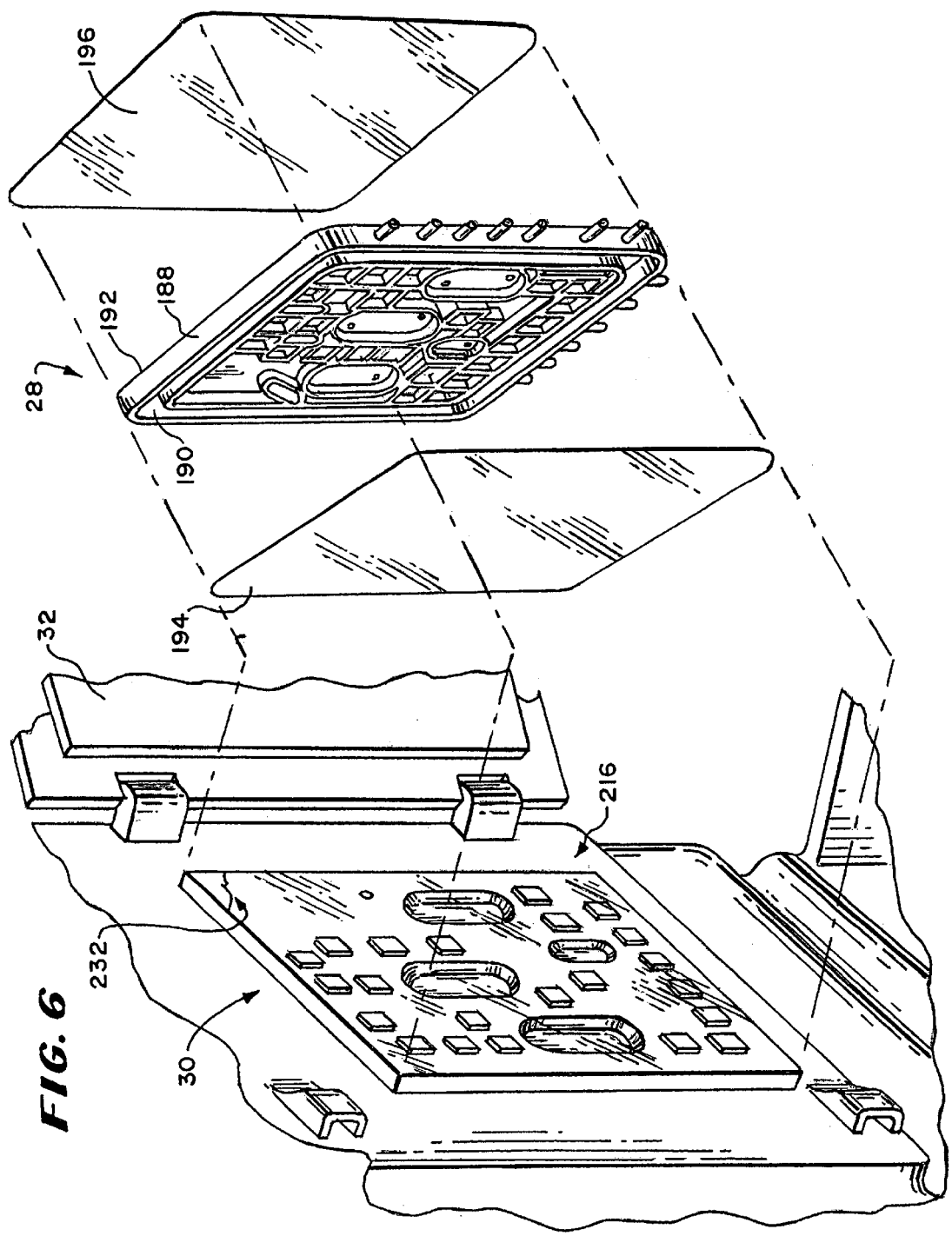
FIG. 6 is an exploded perspective view of a cassette, which contains the programmable blood processing circuit shown in FIG. 5, and the pump and valve station on the processing device shown in FIG. 1, which receives the cassette for use.

In a preferred embodiment, the programmable fluid circuit 46 is implemented by use of a fluid pressure actuated cassette 28 (see FIG. 6). The cassette 28 provides a centralized, programmable, integrated platform for all the pumping and valving functions required for a given blood processing procedure. In the illustrated embodiment, the fluid pressure comprising positive and negative pneumatic pressure. Other types of fluid pressure can be used.

As FIG. 6 shows, the cassette 28 interacts with a pneumatic actuated pump and valve station 30, which is mounted in the lid of the 40 of the case 36 (see FIG. 1). The cassette 28 is, in use, mounted in the pump and valve station 30. The pump and valve station 30 apply positive and negative pneumatic pressure upon the cassette 28 to direct liquid flow through the circuit. Further details will be provided later.

The cassette 28 can take various forms. As illustrated (see FIG. 6), the cassette 28 comprises an injection molded body 188 having a front side 190 and a back side 192. For the purposes of description, the front side 190 is the side of the cassette 28 that, when the cassette 28 is mounted in the pump and valve station 30, faces away from the operator. Flexible diaphragms 194 and 196 overlay both the front side 190 and back sides 192 of the cassette 28, respectively.

The cassette body 188 is preferably made of a rigid medical grade plastic material. The diaphragms 194 and 196 are preferably made of flexible sheets of medical grade plastic. The diaphragms 194 and 196 are sealed about their peripheries to the peripheral edges of the front and back sides of the cassette body 188. Interior regions of the diaphragms 194 and 196 can also be sealed to interior regions of the cassette body 188.

Figure 7:
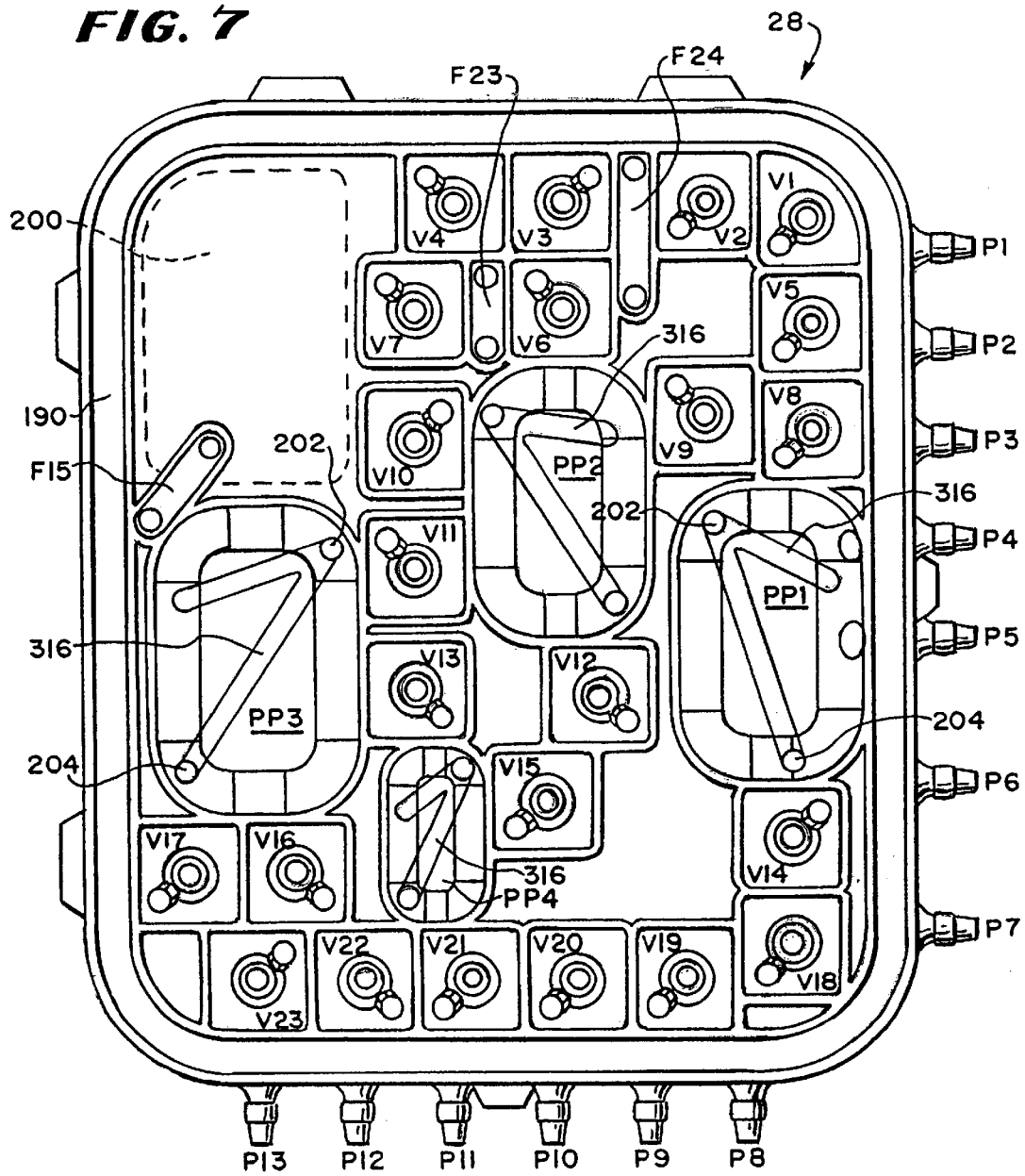
FIG. 7 is a plane view of the front side of the cassette shown in FIG. 6.
Figure 9:
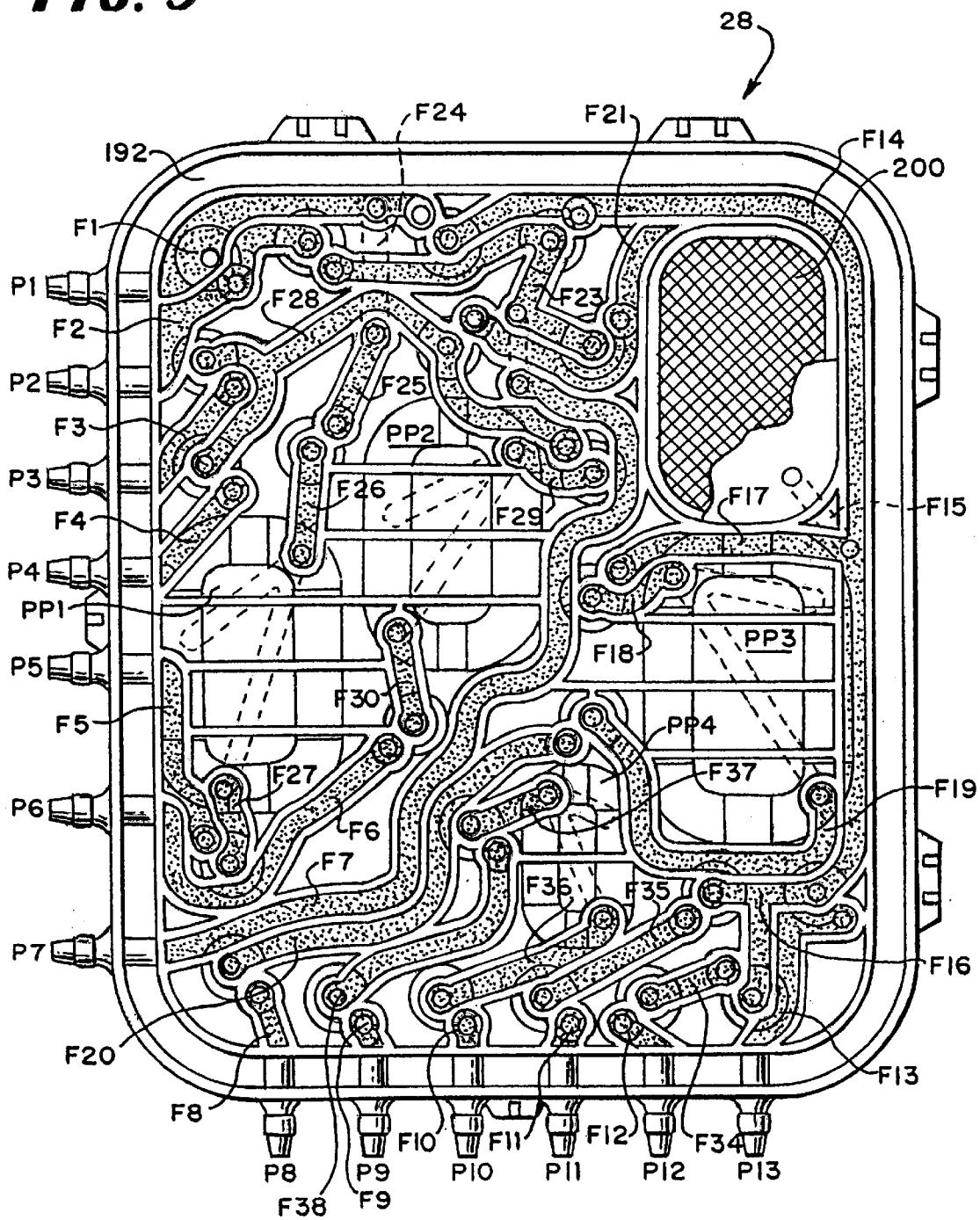
FIG. 9 is a plane view of the back side of the cassette shown in FIG. 6.

The cassette body 188 has an array of interior cavities formed on both the front and back sides 190 and 192 (see FIGS. 7 and 9). The interior cavities define the valve stations and flow paths shown schematically in FIG. 5. An additional interior cavity is provided in the back side of the cassette 28 to form a station that holds a filter material 200. In the illustrated embodiment, the filter material 200 comprises an overmolded mesh filter construction. The filter material 200 is intended, during use, to remove clots and cellular aggregations that can form during blood processing.

The pump stations PP1 to PP4 are formed as wells that are open on the front side 190 of the cassette body 188. Upstanding edges peripherally surround the open wells of the pump stations. The pump wells are closed on the back side 192 of the cassette body 188, except for a spaced pair of through holes or ports 202 and 204 for each pump station. The ports 202 and 204 extend through to the back side 192 of the cassette body 188. As will become apparent, either port 202 or 204 can serve its associated pump station as an inlet or an outlet, or both inlet and outlet.

Figure 8:
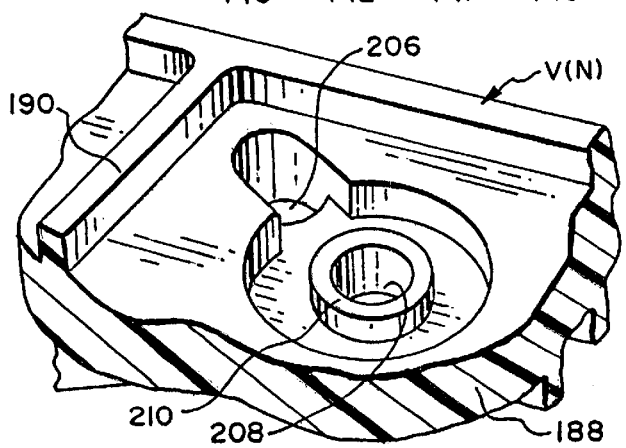
FIG. 8 is an enlarged perspective view of a valve station on the cassette shown in FIG. 6.

The in line valves V1 to V23 are likewise formed as wells that are open on the front side 190 of the cassette. FIG. 8 shows a typical valve V(N). Upstanding edges peripherally surround the open wells of the valves on the front side 190 of the cassette body 188. The valves are closed on the back side 192 of the cassette 28, except that each valve includes a pair of through holes or ports 206 and 208. One port 206 communicates with a selected liquid path on the back side 192 of the cassette body 188. The other port 208 communicates with another selected liquid path on the back side 192 of the cassette body 188.

In each valve, a valve seat 210 extends about one of the ports 208. The valve seat 210 is recessed below the surface of the recessed valve well, such that the port 208 is essentially flush with the surrounding surface of recessed valve well, and the valve seat 210 extends below than the surface of the valve well.

The flexible diaphragm 194 overlying the front side 190 of the cassette 28 rests against the upstanding peripheral edges surrounding the pump stations and valves. With the application of positive force uniformly against this side of the cassette body 188, the flexible diaphragm 194 seats against the upstanding edges. The positive force forms peripheral seals about the pump stations and valves. This, in turn, isolates the pumps and valves from each other and the rest of the system. The pump and valve station 30 applies positive force to the front side 190 of the cassette body 188 for this purpose.

Further localized application of positive and negative fluid pressures upon the regions of the diaphragm 194 overlying these peripherally sealed areas serve to flex the diaphragm regions in these peripherally sealed areas. These localized applications of positive and negative fluid pressures on these diaphragm regions overlying the pump stations serve to expel liquid out of the pump stations (with application of positive pressure) and draw liquid into the pump stations (with application of negative pressure).

In the illustrated embodiment, the bottom of each pump station PP1 to PP4 includes a recessed race 316 (see FIG. 7). The race 316 extends between the ports 202 and 204, and also includes a dogleg extending at an angle from the top port 202. The race 316 provides better liquid flow continuity between the ports 202 and 204, particularly when the diaphragm region is forced by positive pressure against the bottom of the pump station. The race 316 also prevents the diaphragm region from trapping air within the pump station. Air within the pump station is forced into the race 316, where it can be readily venting through the top port 202 out of the pump station, even if the diaphragm region is bottomed out in the station.

Likewise, localized applications of positive and negative fluid pressure on the diaphragm regions overlying the valves will serve to seat (with application of positive pressure) and unseat (with application of negative pressure) these diaphragm regions against the valve seats, thereby closing and opening the associated valve port. The flexible diaphragm is responsive to an applied negative pressure for flexure out of the valve seat 210 to open the respective port. The flexible diaphragm is responsive to an applied positive pressure for flexure into the valve seat 210 to close the respective port. Sealing is accomplished by forcing the flexible diaphragm to flex into the recessed valve seat 210, to seal about the port 208, which is flush with wall of the valve well. The flexible diaphragm forms within the recessed valve seat 210 a peripheral seal about the valve port 208.

In operation, the pump and valve station 30 applies localized positive and negative fluid pressures to these regions of front diaphragm 104 for opening and closing the valve ports.

The liquid paths F1 to F38 are formed as elongated channels that are open on the back side 192 of the cassette body 188, except for the liquid paths F15, F23, and F24 are formed as elongated channels that are open on the front side 190 of the cassette body 188. The liquid paths are shaded in FIG. 9 to facilitate their viewing. Upstanding edges peripherally surround the open channels on the front and back sides 190 and 192 of the cassette body 188.

The liquid paths F1 to F38 are closed on the front side 190 of the cassette body 188, except where the channels cross over valve station ports or pump station ports. Likewise, the liquid paths F31 to F38 are closed on the back side 192 of the cassette body 188, except where the channels cross over in-line ports communicating with certain channels on the back side 192 of the cassette 28.

The flexible diaphragms 194 and 196 overlying the front and back sides 190 and 192 of the cassette body 188 rest against the upstanding peripheral edges surrounding the liquid paths F1 to F38. With the application of positive force uniformly against the front and back sides 190 and 192 of the cassette body 188, the flexible diaphragms 194 and 196 seat against the upstanding edges. This forms peripheral seals along the liquid paths F1 to F38. In operation, the pump and valve station 30 applies positive force to the diaphragms 194 and 196 for this purpose.

The pre-molded ports P1 to P13 extend out along two side edges of the cassette body 188. The cassette 28 is vertically mounted for use in the pump and valve station 30(see FIG. 2). In this orientation, the ports P8 to P13 face downward, and the ports P1 to P7 are vertically stacked one above the other and face inward.

As FIG. 2 shows, the ports P8 to P13, by facing downward, are oriented with container support trays 212 formed in the base 38, as will be described later. The ports P1 to P7, facing inward, are oriented with the centrifuge station 20 and a container weigh station 214, as will also be described in greater detail later. The orientation of the ports P5 to P7 (which serve the processing chamber 18) below the ports P1 to P4 keeps air from entering the processing chamber 18.

This ordered orientation of the ports provides a centralized, compact unit aligned with the operative regions of the case 36.

B. The Universal Set

Figure 10:
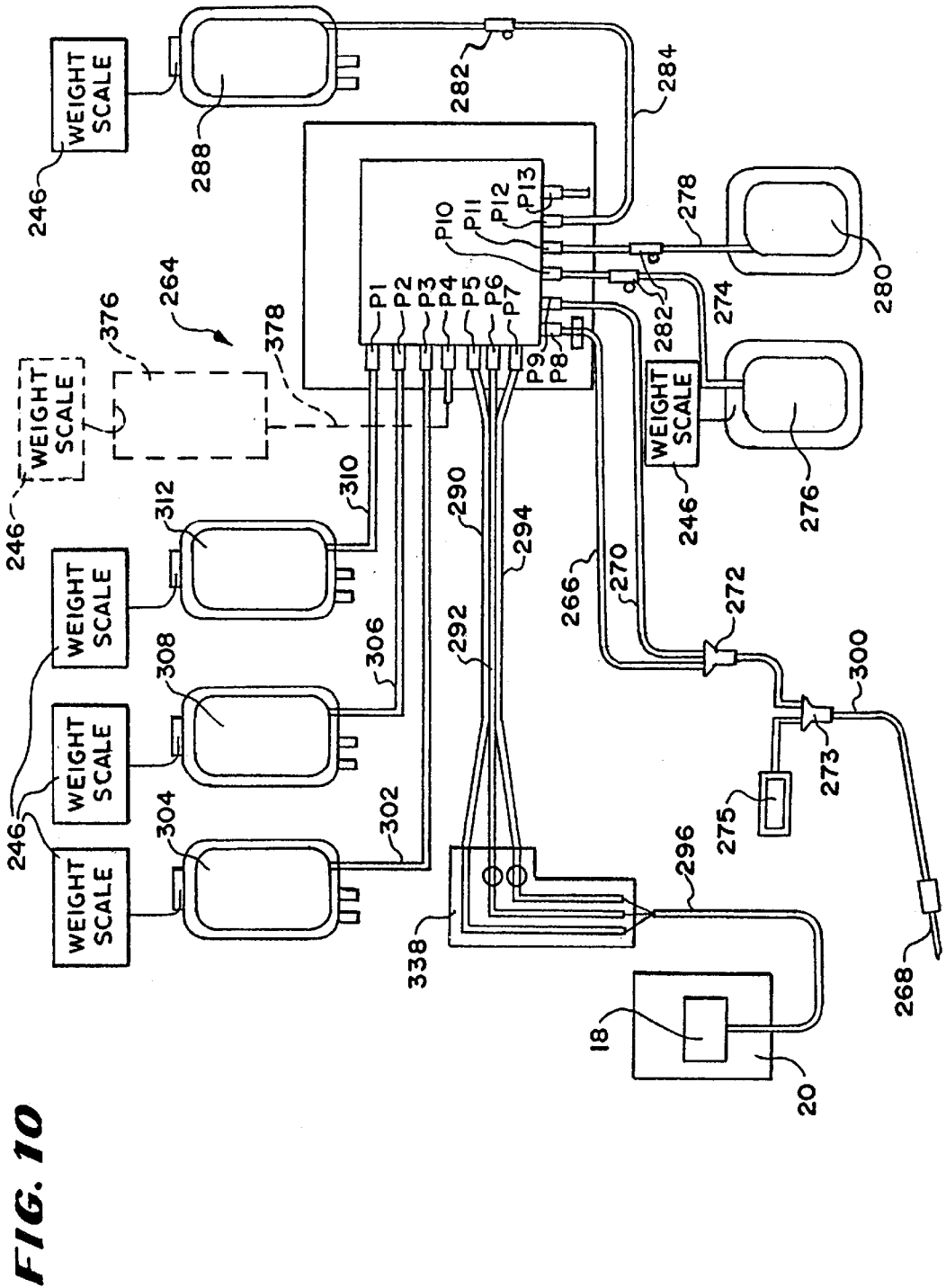
FIG. 10 is a plane view of a universal processing set, which incorporates the cassette shown in FIG. 6, and which can be mounted on the device shown in FIG. 1, as shown in FIGS. 2 and 3.

FIG. 10 schematically shows a universal set 264, which, by selective programming of the blood processing circuit 46 implemented by cassette 28, is capable of performing several different blood processing procedures.

The universal set 264 includes a donor tube 266, which is attached (through y-connectors 272 and 273) to tubing 300 having an attached phlebotomy needle 268. The donor tube 266 is coupled to the port P8 of the cassette 28.

A container 275 for collecting an in-line sample of blood drawn through the tube 300 is also attached through the y-connector 273.

An anticoagulant tube 270 is coupled to the phlebotomy needle 268 via the y-connector 272. The anticoagulant tube 270 is coupled to cassette port P9. A container 276 holding anticoagulant is coupled via a tube 274 to the cassette port P10. The anticoagulant tube 270 carries an external, manually operated in line clamp 282 of conventional construction.

A container 280 holding a red blood cell additive solution is coupled via a tube 278 to the cassette port P3. The tube 278 also carries an external, manually operated in line clamp 282.

A container 288 holding saline is coupled via a tube 284 to the cassette port P12.

FIG. 10 shows the fluid holding containers 276, 280, and 288 as being integrally attached during manufacture of the set 264. Alternatively, all or some of the containers 276, 280, and 288 can be supplied separate from the set 264. The containers 276, 280, and 288 may be coupled by conventional spike connectors, or the set 264 may be configured to accommodate the attachment of the separate container or containers at the time of use through a suitable sterile connection, to thereby maintain a sterile, closed blood processing environment. Alternatively, the tubes 274, 278, and 284 can carry an in-line sterilizing filter and a conventional spike connector for insertion into a container port at time of use, to thereby maintain a sterile, closed blood processing environment.

The set 264 further includes tubes 290, 292, 294, which extend to an umbilicus 296. When installed in the processing station, the umbilicus 296 links the rotating processing chamber 18 with the cassette 28 without need for rotating seals. Further details of this construction will be provided later.

The tubes 290, 292, and 294 are coupled, respectively, to the cassette ports P5, P6, and P7. The tube 290 conveys whole blood into the processing chamber 18. The tube 292 conveys plasma from the processing chamber 18. The tube 294 conveys red blood cells from processing chamber 18.

A plasma collection container 304 is coupled by a tube 302 to the cassette port P3. The collection container 304 is intended, in use, to serve as a reservoir for plasma during processing.

A red blood cell collection container 308 is coupled by a tube 306 to the cassette port P2. The collection container 308 is intended, in use, to receive a first unit of red blood cells for storage.

A whole blood reservoir 312 is coupled by a tube 310 to the cassette port P1. The collection container 312 is intended, in use, to serve as a reservoir for whole blood during processing. It can also serve to receive a second unit of red blood cells for storage.

As shown in FIG. 10, no tubing is coupled to the utility cassette port P13 and buffy port P4.

C. The Pump and Valve Station

The pump and valve station 30 includes a cassette holder 216. The door 32 is hinged to move with respect to the cassette holder 216 between the opened position, exposing the cassette holder 216 (shown in FIG. 6) and the closed position, covering the cassette holder 216 (shown in FIG. 3). The door 32 also includes an over center latch 218 with a latch handle 220. When the door 32 is closed, the latch 218 swings into engagement with the latch pin 222.

Figure 11:
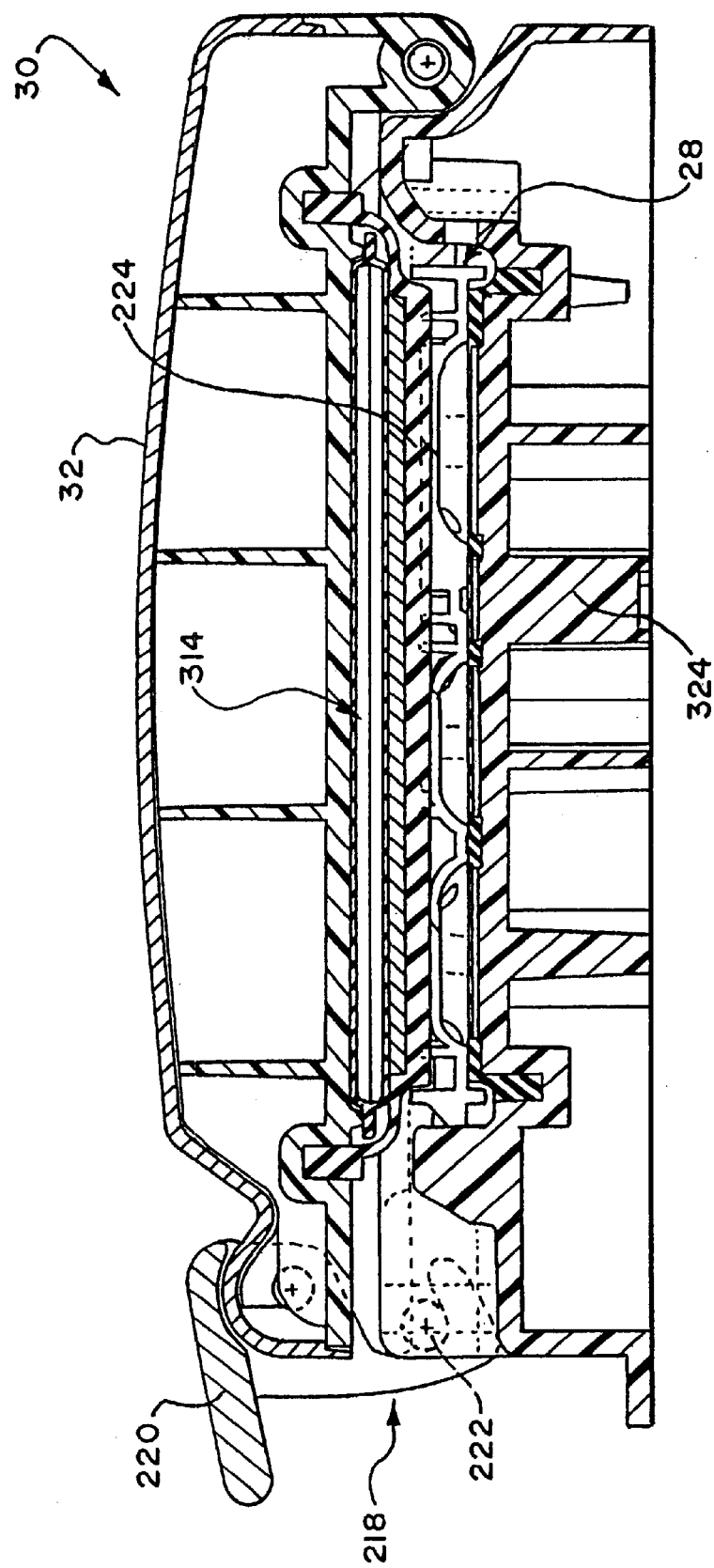
FIG. 11 is a top section view of the pump and valve station in which the cassette as shown in FIG. 6 is carried for use.

As FIG. 11 shows, the inside face of the door 32 carries an elastomeric gasket 224. The gasket 224 contacts the back side 192 of the cassette 28 when the door 32 is closed. An inflatable bladder 314 underlies the gasket 224.

With the door 32 opened (see FIG. 2), the operator can place the cassette 28 into the cassette holder 216. Closing the door 32 and securing the latch 218 brings the gasket 224 into facing contact with the diaphragm 196 on the back side 192 of the cassette 28. Inflating the bladder 314 presses the gasket 224 into intimate, sealing engagement against the diaphragm 196. The cassette 28 is thereby secured in a tight, sealing fit within the cassette holder 216.

The inflation of the bladder 314 also fully loads the over center latch 218 against the latch pin 222 with a force that cannot be overcome by normal manual force against the latch handle 220. The door 32 is securely locked and cannot be opened when the bladder 314 is inflated. In this construction, there is no need for an auxiliary lock-out device or sensor to assure against opening of the door 32 during blood processing.

The pump and valve station 30 also includes a manifold assembly 226 located in the cassette holder 216. The manifold assembly 226 comprises a molded or machined plastic or metal body. The front side 194 of the diaphragm is held in intimate engagement against the manifold assembly 226 when the door 32 is closed and bladder 314 inflated.

The manifold assembly 226 is coupled to a pneumatic pressure source 234, which supplies positive and negative air pressure. The pneumatic pressure source 234 is carried inside the lid 40 behind the manifold assembly 226.

Figure 12:
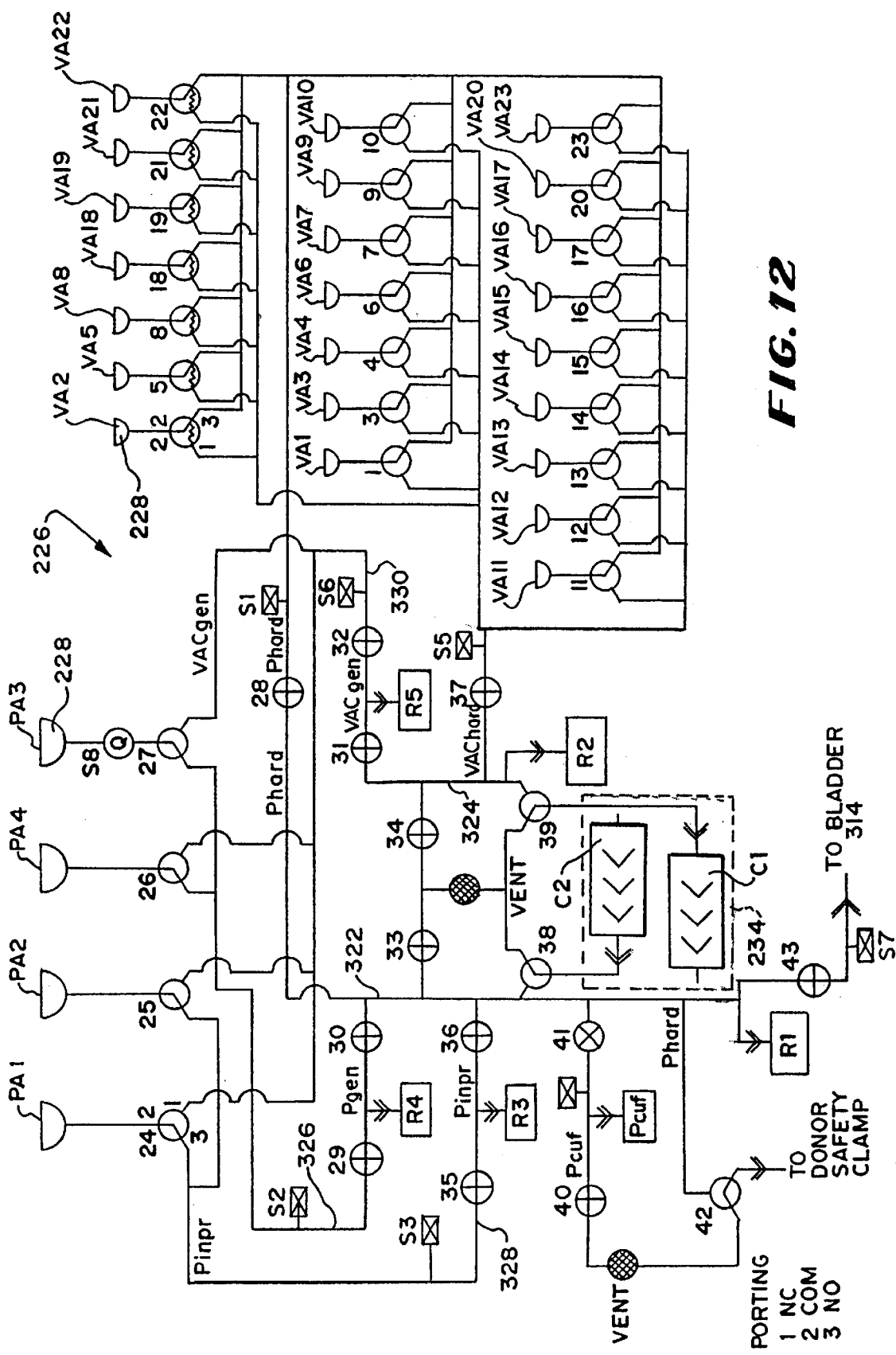
FIG. 12 is a schematic view of a pneumatic manifold assembly, which is part of the pump and valve station shown in FIG. 6, and which supplies positive and negative pneumatic pressures to convey fluid through the cassette shown in FIGS. 7 and 9.

In the illustrated embodiment, the pressure source 234 comprises two compressors C1 and C2. However, one or several dual-head compressors could be used as well. As FIG. 12 shows, one compressor C1 supplies negative pressure through the manifold 226 to the cassette 28. The other compressor C2 supplies positive pressure through the manifold 226 to the cassette 28.

As FIG. 12 shows, the manifold 226 contains four pump actuators PA1 to PA4 and twenty-three valve actuators VA1 to VA23. The pump actuators PA1 to PA4 and the valve actuators VA1 to VA23 are mutually oriented to form a mirror image of the pump stations PP1 to PP4 and valve stations V1 to V23 on the front side 190 of the cassette 28.

Figure 22:
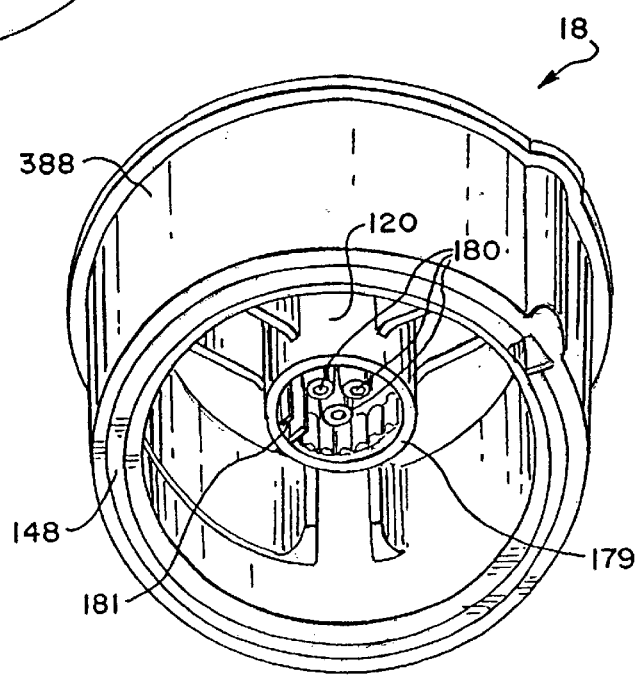
FIG. 22 is a bottom perspective view of the molded processing container shown in FIG. 21.

As FIG. 22 also shows, each actuator PA1 to PA4 and VA1 to VA23 includes a port 228. The ports 228 convey positive or negative pneumatic pressures from the source in a sequence governed by the controller 16. These positive and negative pressure pulses flex the front diaphragm 194 to operate the pump chambers PP1 to PP4 and valve stations V1 to V23 in the cassette 28. This, in turn, moves blood and processing liquid through the cassette 28.

The cassette holder 216 preferably includes an integral elastomeric membrane 232 (see FIG. 6) stretched across the manifold assembly 226. The membrane 232 serves as the interface between the piston element 226 and the diaphragm 194 of the cassette 28, when fitted into the holder 216. The membrane 232 may include one or more small through holes (not shown) in the regions overlying the pump and valve actuators PA1 to PA4 and V1 to V23. The holes are sized to convey pneumatic fluid pressure from the manifold assembly 226 to the cassette diaphragm 194. Still, the holes are small enough to retard the passage of liquid. The membrane 232 forms a flexible splash guard across the exposed face of the manifold assembly 226.

The splash guard membrane 232 keeps liquid out of the pump and valve actuators PA1 to PA4 and VA1 to VA23, should the cassette diaphragm 194 leak. The splash guard membrane 232 also serves as a filter to keep particulate matter out of the pump and valve actuators of the manifold assembly 226. The splash guard membrane 232 can be periodically wiped clean when cassettes 28 are exchanged. The manifold assembly 226 includes an array of solenoid actuated pneumatic valves, which are coupled in-line with the pump and valve actuators PA1 to PA4 and VA1 to VA23. The manifold assembly 226, under the control of the controller 16, selectively distributes the different pressure and vacuum levels to the pump and valve actuators PA(N) and VA(N). These levels of pressure and vacuum are systematically applied to the cassette 28, to route blood and processing liquids.

Under the control of a controller 16, the manifold assembly 226 also distributes pressure levels to the door bladder 314 (already described), as well as to a donor pressure cuff (not shown) and to a donor line occluder 320.

As FIG. 1 shows, the donor line occluder 320 is located in the case 36, immediately below the pump and valve station 30, in alignment with the ports P8 and P9 of the cassette 28. The donor line 266, coupled to the port P8, passes through the occluder 320. The anticoagulant line 270, coupled to the port P9, also passes through the occluder 320. The occluder 320 is a spring loaded, normally closed pinch valve, between which the lines 266 and 270 pass. Pneumatic pressure from the manifold assembly 234 is supplied to a bladder (not shown) through a solenoid valve. The bladder, when expanded with pneumatic pressure, opens the pinch valve, to thereby open the lines 266 and 270. In the absence of pneumatic pressure, the solenoid valve closes and the bladder vents to atmosphere. The spring loaded pinch valve of the occluder 320 closes, thereby closing the lines 266 and 270.

The manifold assembly 226 maintains several different pressure and vacuum conditions, under the control of the controller 16. In the illustrated embodiment, the following multiple pressure and vacuum conditions are maintained:

(i) Phard, or Hard Pressure, and Pinpr, or In-Process Pressure are the highest pressures maintained in the manifold assembly 226. Phard is applied for closing cassette valves V1 to V23. Pinpr is applied to drive the expression of liquid from the in-process pump PP1 and the plasma pump PP2. A typical pressure level for Phard and Pinpr in the context of the preferred embodiment is 500 mmHg.

(ii) Pgen, or General Pressure, is applied to drive the expression of liquid from the donor interface pump PP3 and the anticoagulant pump PP4. A typical pressure level for Pgen in the context of the preferred embodiment is 150 mmHg.

(iii) Pcuff, or Cuff Pressure, is supplied to the donor pressure cuff. A typical pressure level for Pcuff in the context of the preferred embodiment is 80 mmHg.

(iv) Vhard, or Hard Vacuum, is the deepest vacuum applied in the manifold assembly 226. Vhard is applied to open cassette valves V1 to V23. A typical vacuum level for Vhard in the context of the preferred embodiment is −350 mmHg.

(vi) Vgen, or General Vacuum, is applied to drive the draw function of each of the four pumps PP1 to PP4. A typical pressure level for Vgen in the context of the preferred embodiment is −300 mmHg. (vii) Pdoor, or Door Pressure, is applied to the bladder 314 to seal the cassette 28 into the holder 216. A typical pressure level for Pdoor in the context of the preferred embodiment is 700 mmHg.

For each pressure and vacuum level, a variation of plus or minus 20 mmHg is tolerated.

Pinpr is used to operate the in process pump PP1, to pump blood into the processing chamber 18. The magnitude of Pinpr must be sufficient to overcome a minimum pressure of approximately 300 mm Hg, which is typically present within the processing chamber 18.

Similarly, Pinpr is used for the plasma pump PP2, since it must have similar pressure capabilities in the event that plasma needs to be pumped backwards into the processing chamber 18, e.g., during a spill condition, as will be described later.

Pinpr and Phard are operated at the highest pressure to ensure that upstream and downstream valves used in conjunction with pumping are not forced opened by the pressures applied to operate the pumps. The cascaded, interconnectable design of the fluid paths F1 to F38 through the cassette 28 requires Pinpr-Phard to be the highest pressure applied. By the same token, Vgen is required to be less extreme than Vhard, to ensure that pumps PP1 to PP4 do not overwhelm upstream and downstream cassette valves V1 to V23.

Pgen is used to drive the donor interface pump PP3 and can be maintained at a lower pressure, as can the AC pump PP4.

A main hard pressure line 322 and a main vacuum line 324 distribute Phard and Vhard in the manifold assembly 324. The pressure and vacuum sources 234 run continuously to supply Phard to the hard pressure line 322 and Vhard to the hard vacuum line 324.

A pressure sensor S1 monitors Phard in the hard pressure line 322. The sensor S1 controls a solenoid 38. The solenoid 38 is normally closed. The sensor S1 opens the solenoid 38 to build Phard up to its maximum set value. Solenoid 38 is closed as long as Phard is within its specified pressure range and is opened when Phard falls below its minimum acceptable value.

Similarly, a pressure sensor S5 in the hard vacuum line 324 monitors Vhard. The sensor S5 controls a solenoid 39. The solenoid 39 is normally closed. The sensor S5 opens the solenoid 39 to build Vhard up to its maximum value. Solenoid 39 is closed as long as Vhard is within its specified pressure range and is opened when Vhard falls outside its specified range.

A general pressure line 326 branches from the hard pressure line 322. A sensor S2 in the general pressure line 326 monitors Pgen. The sensor 32 controls a solenoid 30. The solenoid 30 is normally closed. The sensor S2 opens the solenoid 30 to refresh Pgen from the hard pressure line 322, up to the maximum value of Pgen. Solenoid 30 is closed as long as Pgen is within its specified pressure range and is opened when Pgen falls outside its specified range.

An in process pressure line 328 also branches from the hard pressure line 322. A sensor S3 in the in process pressure line 328 monitors Pinpr. The sensor S3 controls a solenoid 36. The solenoid 36 is normally closed. The sensor S3 opens the solenoid 36 to refresh Pinpr from the hard pressure line 322, up to the maximum value of Pinpr. Solenoid 36 is closed as long as Pinpr is within its specified pressure range and is opened when Pinpr falls outside its specified range.

A general vacuum line 330 branches from the hard vacuum line 324. A sensor S6 monitors Vgen in the general vacuum line 330. The sensor S6 controls a solenoid 31. The solenoid 31 is normally closed. The sensor S6 opens the solenoid 31 to refresh Vgen from the hard vacuum line 324, up to the maximum value of Vgen. The solenoid 31 is closed as long as Vgen is within its specified range and is opened when Vgen falls outside its specified range.

In-line reservoirs R1 to R5 are provided in the hard pressure line 322, the in process pressure line 328, the general pressure line 326, the hard vacuum line 324, and the general vacuum line 330. The reservoirs R1 to R5 assure that the constant pressure and vacuum adjustments as above described are smooth and predictable.

The solenoids 33 and 34 provide a vent for the pressures and vacuums, respectively, upon procedure completion. Since pumping and valving will continually consume pressure and vacuum, the solenoids 33 and 34 are normally closed. The solenoids 33 and 34 are opened to vent the manifold assembly upon the completion of a blood processing procedure.

The solenoids 28, 29, 35, 37 and 32 provide the capability to isolate the reservoirs R1 to R5 from the air lines that supply vacuum and pressure to the manifold assembly 226. This provides for much quicker pressure/vacuum decay feedback, so that testing of cassette/manifold assembly seal integrity can be accomplished. These solenoids 28, 29, 35, 37, and 32 are normally opened, so that pressure cannot be built in the assembly 226 without a command to close the solenoids 28, 29, 35, 37, and 32, and, further, so that the system pressures and vacuums can vent in an error mode or with loss of power.

The solenoids 1 to 23 provide Phard or Vhard to drive the valve actuators VA1 to V23. In the unpowered state, these solenoids are normally opened to keep all cassette valves V1 to V23 closed.

The solenoids 24 and 25 provide Pinpr and Vgen to drive the in-process and plasma pumps PP1 and PP2. In the unpowered state, these solenoids are opened to keep both pumps PP1 and PP2 closed.

The solenoids 26 and 27 provide Pgen and Vgen to drive the donor interface and AC pumps PP3 and PP4. In the unpowered state, these solenoids are opened to keep both pumps PP3 and PP4 closed.

The solenoid 43 provides isolation of the door bladder 314 from the hard pressure line 322 during the procedure. The solenoid 43 is normally opened and is closed when Pdoor is reached. A sensor S7 monitors Pdoor and signals when the bladder pressure falls below Pdoor. The solenoid 43 is opened in the unpowered state to ensure bladder 314 venting, as the cassette 28 cannot be removed from the holder while the door bladder 314 is pressurized.

The solenoid 42 provides Phard to open the safety occluder valve 320. Any error modes that might endanger the donor will relax (vent) the solenoid 42 to close the occluder 320 and isolate the donor. Similarly, any loss of power will relax the solenoid 42 and isolate the donor.

The sensor S4 monitors Pcuff and communicates with solenoids 41 (for increases in pressure) and solenoid 40 (for venting) to maintain the donor cuff within its specified ranges during the procedure. The solenoid 40 is normally open so that the cuff line will vent in the event of system error or loss of power. The solenoid 41 is normally closed to isolate the donor from any Phard in the event of power loss or system error.

FIG. 12 shows a sensor S8 in the pneumatic line serving the donor interface pump actuator PA3. The sensor S8 is a bi-directional mass air flow sensor, which can monitor air flow to the donor interface pump actuator PA3 to detect occlusions in the donor line. Alternatively, as will be described in greater detail later, electrical field variations can be sensed by an electrode carried within the donor interface pump chamber PP3, or any or all other pump chambers PP1, PP2, or PP4, to detect occlusions, as well as to permit calculation of flow rates and the detection of air.

Various alternative embodiments are possible. For example, the pressure and vacuum available to the four pumping chambers could be modified to include more or less distinct levels or different groupings of "shared" pressure and vacuum levels. As another example, Vhard could be removed from access to the solenoids 2, 5, 8, 18, 19, 21, 22 since the restoring springs will return the cassette valves to a closed position upon removal of a vacuum. Furthermore, the vents shown as grouped together could be isolated or joined in numerous combinations.

It should also be appreciated that any of the solenoids used in "normally open" mode could be re-routed pneumatically to be realized as "normally closed". Similarly, any of the "normally closed" solenoids could be realized as "normally open".

As another example of an alternative embodiment, the hard pressure reservoir R1 could be removed if Pdoor and Phard were set to identical magnitudes. In this arrangement, the door bladder 314 could serve as the hard pressure reservoir. The pressure sensor S7 and the solenoid 43 would also be removed in this arrangement.

III. Other Process Control Components of the System

Figure 13:
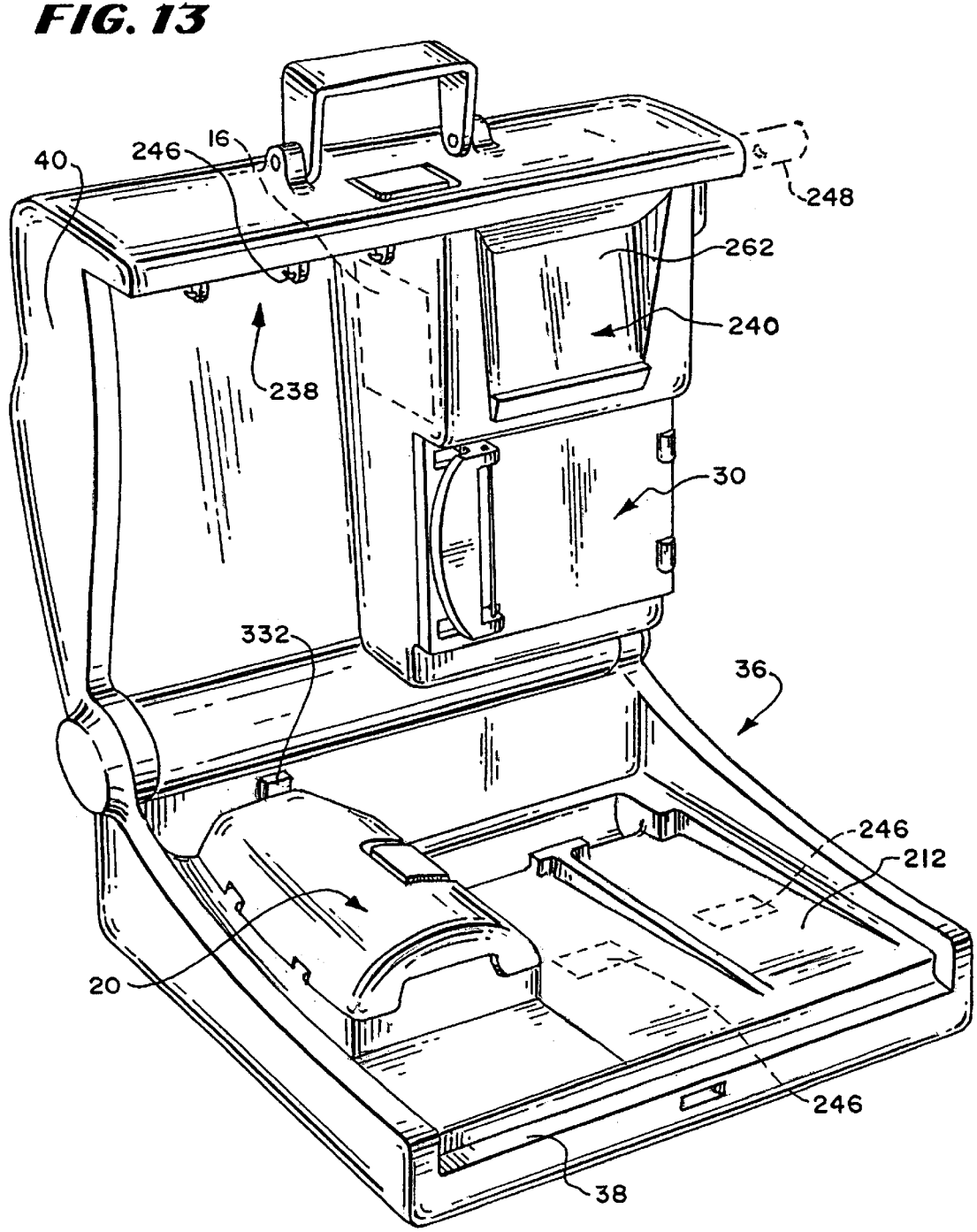
FIG. 13 is a perspective front view of the case that houses the processing device, with the lid open for use of the device, and showing the location of various processing elements housed within the case.

As FIG. 13 best shows, the case 36 contains other components compactly arranged to aid blood processing. In addition to the centrifuge station 20 and pump and valve station 30, already described, the case 36 includes a weigh station 238, an operator interface station 240, and one or more trays 212 or hangers 248 for containers. The arrangement of these components in the case 36 can vary. In the illustrated embodiment, the weigh station 238, the controller 16, and the user interface station 240, like the pump and valve station 30, are located in the lid 40 of the case 36. The holding trays 212 are located in base 38 of the case 36, adjacent the centrifuge station 20.

A. Container Support Components

The weigh station 238 comprises a series of container hangers/weigh sensors 246 arranged along the top of the lid 40. In use (see FIG. 2), containers 304, 308, 312 are suspended on the hangers/weigh sensors 246.

The containers receive blood components separated during processing, as will be described in greater detail later. The weigh sensors 246 provide output reflecting weight changes over time. This output is conveyed to the controller 16. The controller 16 processes the incremental weight changes to derive fluid processing volumes and flow rates. The controller generates signals to control processing events based, in part, upon the derived processing volumes. Further details of the operation of the controller to control processing events will be provided later.

The holding trays 212 comprise molded recesses in the base 38. The trays 212 accommodate the containers 276 and 280 (see FIG. 2). In the illustrated embodiment, an additional swing-out hanger 248 is also provided on the side of the lid 40. The hanger 248 (see FIG. 2) supports the container 288 during processing. In the illustrated embodiment, the trays 212 and hanger 248 also include weigh sensors 246.

Figure 40:
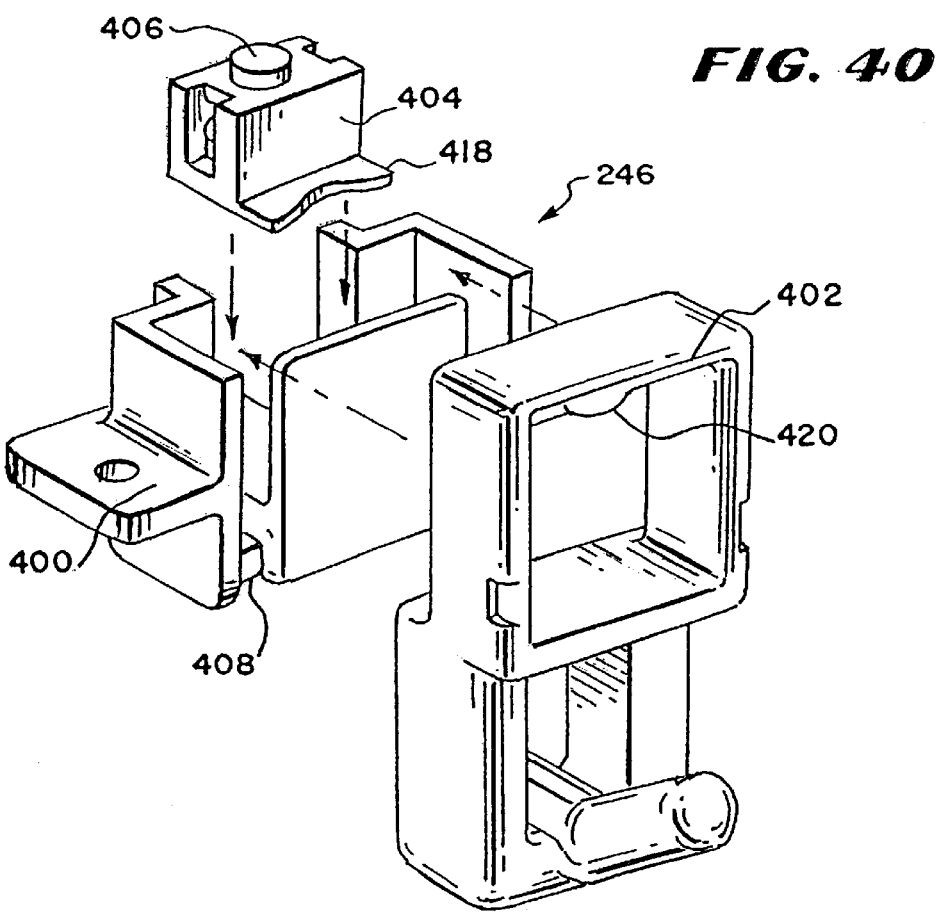
FIG. 40 is a representative embodiment of a weigh scale suited for use in association with the device shown in FIG. 1.

The weigh sensors 246 can be variously constructed. In the embodiment shown in FIG. 40, the scale includes a force sensor 404 incorporated into a housing 400, to which a hanger 402 is attached. The top surface 420 of hanger 402 engages a spring 406 on the sensor 404. Another spring 418 is compressed as a load, carried by the hanger 402, is applied. The spring 418 resists load movement of the hanger 402, until the load exceeds a predetermined weight (e.g., 2 kg.). At that time, the hanger 402 bottoms out on mechanical stops 408 in the housing 400, thereby providing over load protection.

Figure 41:
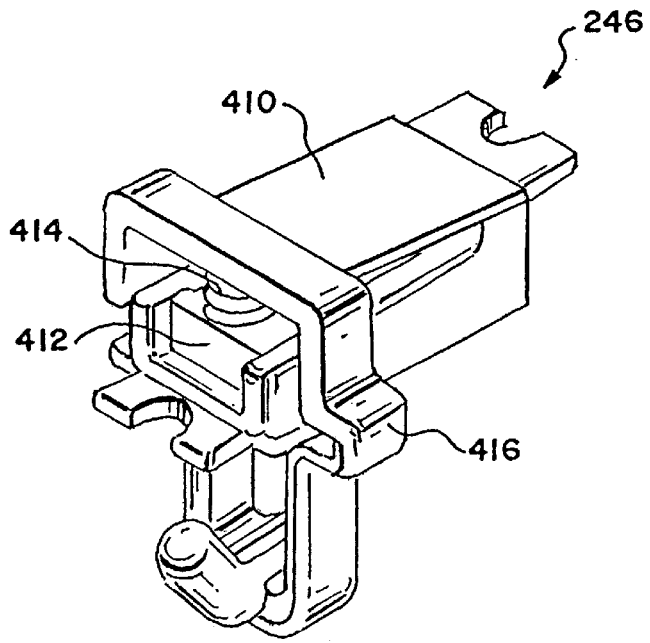
FIG. 41 is a representative embodiment of another weigh suited for use in association with the device shown in FIG. 1.

In the embodiment shown in FIG. 41, a supported beam 410 transfers force applied by a hanger 416 to a force sensor 412 through a spring 414. This design virtually eliminates friction from the weight sensing system. The magnitude of the load carried by the beam is linear in behavior, and the weight sensing system can be readily calibrated to ascertain an actual load applied to the hanger 416.

B. The Controller and Operator Interface Station

Figure 14:
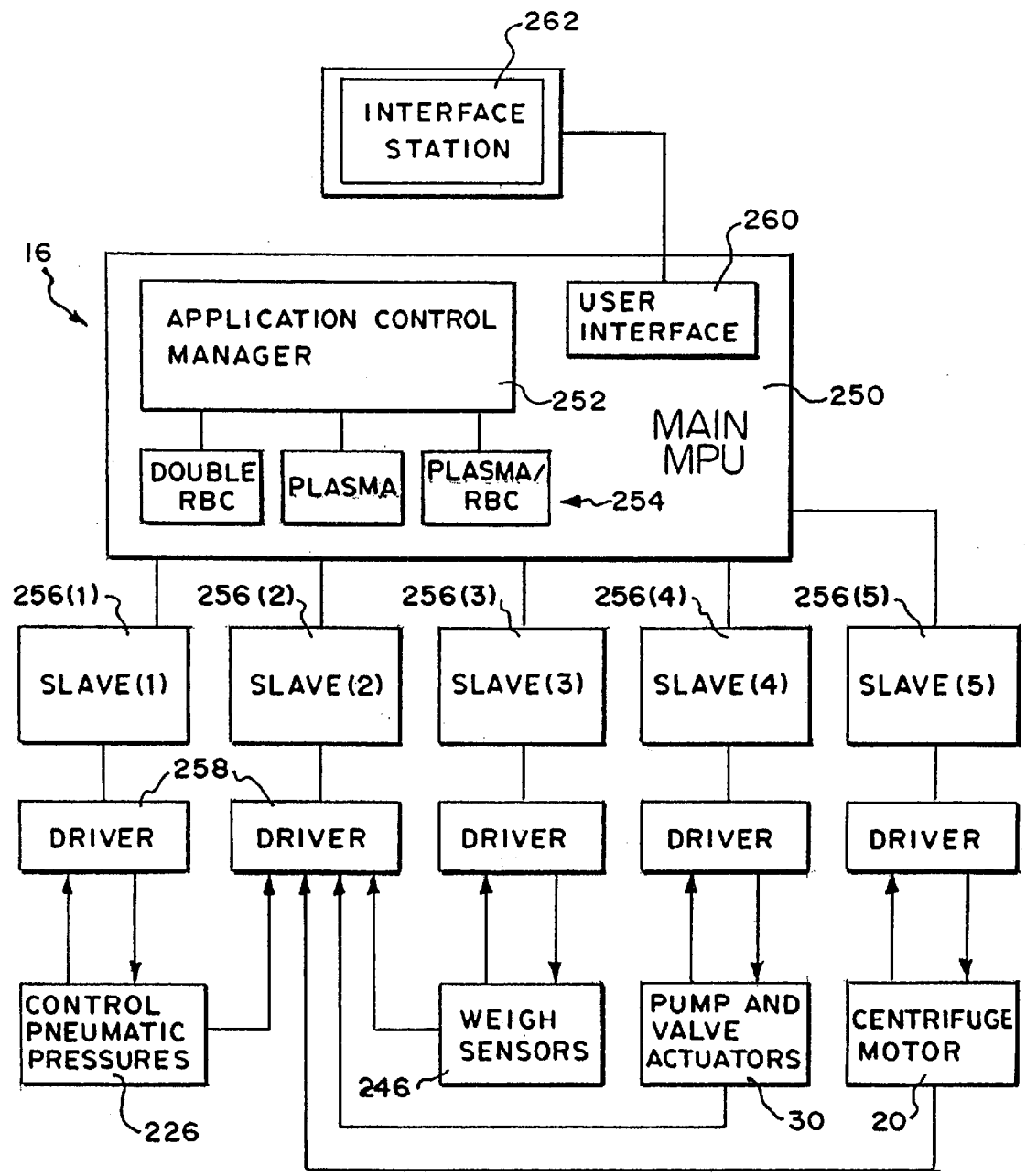
FIG. 14 is a schematic view of the controller that carries out the process control and monitoring functions of the device shown in FIG. 1.

The controller 16 carries out process control and monitoring functions for the system 10. As FIG. 14 shows schematically, the controller 16 comprises a main processing unit (MPU) 250, which can comprise, e.g., a Pentium™ type microprocessor made by Intel Corporation, although other types of conventional microprocessors can be used. The MPU 250 is mounted inside the lid 40 of the case 36 (as FIG. 13 shows).

In the preferred embodiment, the MPU 250 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is scheduled.

As FIG. 14 shows, the MPU 250 includes an application control manager 252. The application control manager 252 administers the activation of a library of at least one control application 254. Each control application 254 prescribes procedures for carrying out given functional tasks using the centrifuge station 20 and the pump and valve station 30 in a predetermined way. In the illustrated embodiment, the applications 254 reside as process software in EPROM's in the MPU 250.

The number of applications 254 can vary. In the illustrated embodiment, the applications 254 includes at least one clinical procedure application. The procedure application contains the steps to carry out one prescribed clinical processing procedure. For the sake of example in the illustrated embodiment, the application 254 includes three procedure applications: (1) a double unit red blood cell collection procedure; (2) a plasma collection procedure; and (3) a plasma/red blood cell collection procedure. The details of these procedures will be described later. Of course, additional procedure applications can be included.

As FIG. 14 shows, several slave processing units communicate with the application control manager 252. While the number of slave processing units can vary, the illustrated embodiment shows five units 256(1) to 256 (5). The slave processing units 256 (1) to 256 (5), in turn, communicates with low level peripheral controllers 258 for controlling the pneumatic pressures within the manifold assembly 226, the weigh sensors 246, the pump and valve actuators PA1 to PA4 and VA1 to VA23 in the pump and valve station 30, the motor for the centrifuge station 20, the interface sensing station 332, and other functional hardware of the system.

The MPU 250 contains in EPROM's the commands for the peripheral controllers 258, which are downloaded to the appropriate slave processing unit 256(1) to 256(5) at start-up. The application control manager 252 also downloads to the appropriate slave processing unit 256(1) to 256(5) the operating parameters prescribed by the activated application 254.

With this downloaded information, the slave processing units 256(1) to 256(5) proceed to generate device commands for the peripheral controllers 258, causing the hardware to operate in a specified way to carry out the procedure. The peripheral controllers 258 return current hardware status information to the appropriate slave processing unit 256(1) to 256(5), which, in turn, generate the commands necessary to maintain the operating parameters ordered by the application control manager 252.

In the illustrated embodiment, one slave processing unit 256(2) performs the function of an environmental manager. The unit 256(2) receives redundant current hardware status information and reports to the MPU 250 should a slave unit malfunction and fail to maintain the desired operating conditions.

As FIG. 14 shows, the MPU 250 also includes an interactive user interface 260, which allows the operator to view and comprehend information regarding the operation of the system 10. The interface 260 is coupled to the interface station 240. The interface 260 allows the operator to use the interface station 240 to select applications 254 residing in the application control manager 252, as well as to change certain functions and performance criteria of the system 10.

As FIG. 13 shows, the interface station 240 includes an interface screen 262 carried in the lid 40. The interface screen 262 displays information for viewing by the operator in alpha-numeric format and as graphical images. In the illustrated and preferred embodiment, the interface screen 262 also serves as an input device. It receives input from the operator by conventional touch activation.

C. On-Line Monitoring of Pump Flows

1. Gravimetric Monitoring

Using the weigh scales 246, either upstream or downstream of the pumps, the controller 16 can continuously determine the actual volume of fluid that is moved per pump stroke and correct for any deviations from commanded flow. The controller 16 can also diagnose exceptional situations, such as leaks and obstructions in the fluid path. This measure of monitoring and control is desirable in an automated apheresis application, where anticoagulant has to be accurately metered with the whole blood as it is drawn from the donor, and where product quality (e.g., hematocrit, plasma purity) is influenced by the accuracy of the pump flow rates.

The pumps PP1 to PP4 in the cassette 28 each provides a relatively-constant nominal stroke volume, or SV. The flow rate for a given pump can therefore be expressed as follows:

$$Q = \frac{SV}{(T_{Pump} + T_{Fill} + T_{Idle})} \quad (1)$$

where:

Q is the flow rate of the pump.

SV is the stroke volume, or volume moved per pump cycle.

$T_{Pump}$ is the time the fluid is moved out of the pump chamber.

$T_{Fill}$ is the time the pump is filled with fluid, and $T_{Idle}$ is the time when the pump is idle, that is, when no fluid movement occurs.

The SV can be affected by the interaction of the pump with attached downstream and upstream fluid circuits. This is analogous, in electrical circuit theory, to the interaction of a non-ideal current source with the input impedance of the load it sees. Because of this, the actual SV can be different than the nominal SV.

The actual fluid flow in volume per unit of time $Q_{Actual}$ can therefore be expressed as follows:

$$Q_{Actual} = k \times \frac{SV_{Ideal}}{T_{Pump} + T_{Fill} + T_{Idle}} \quad (2)$$

where:

$Q_{Actual}$ is the actual fluid flow in volume per unit of time.

$SV_{Ideal}$ is the theoretical stroke volume, based upon the geometry of the pump chamber. k is a correction factor that accounts for the interactions between the pump and the upstream and downstream pressures.

The actual flow rate can be ascertained gravimetrically, using the upstream or downstream weigh scales 246, based upon the following relationship:

$$Q_{Actual} = \frac{\Delta Wt}{\rho \times \Delta T} \quad (3)$$

where:

$\Delta Wt$ is the change in weight of fluid as detected by the upstream or downstream weigh scale 246 during the time period $\Delta T$, $\rho$ is the density of fluid.

$\Delta T$ is the time period where the change in weight $\Delta Wt$ is detected in the weigh scale 246.

The following expression is derived by combining Equations (2) and (3):

$$k = (T_{Pump} + T_{Fill} + T_{Idle}) \times \frac{\Delta Wt}{(SV_{Ideal} \times \rho \times \Delta T)} \quad (4)$$

The controller 16 computes k according to Equation (4) and then adjusts $T_{Idle}$ so that the desired flow rate is achieved, as follows:

$$T_{Idle} = \left(k \times \frac{SV_{Ideal}}{Q_{Desired}}\right) - T_{Pump} - T_{Fill} \quad (5)$$

The controller 16 updates the values for k and $T_{Idle}$ frequently to adjust the flow rates.

Alternatively, the controller 16 can change $T_{Pump}$ and/or $T_{Fill}$ and/or $T_{Idle}$ to adjust the flow rates.

In this arrangement, one or more of the time interval components $T_{Pump}$, or $T_{Fill}$, or $T_{Idle}$ is adjusted to a new magnitude to achieve $Q_{Desired}$, according to the following relationship:

$$T_{n(Adjusted)} = k\left(\frac{SV_{Ideal}}{Q_{Desired}}\right) - T_{n(NotAdjusted)}$$

where:

$T_{n(Adjusted)}$ is the magnitude of the time interval component or components after adjustment to achieve the desired flow rate $Q_{Desired}$.

$T_{n(NotAdjusted)}$ is the magnitude of the value of the other time interval component or components of $T_{Stroke}$ that are not adjusted. The adjusted stroke interval after adjustment to achieve the desired flow rate $Q_{Desired}$ is the sum of $T_{n(Adjusted)}$ and $T_{n(NotAdjusted)}$.

The controller 16 also applies the correction factor k as a diagnostics tool to determine abnormal operating conditions. For example, if k differs significantly from its nominal value, the fluid path may have either a leak or an obstruction. Similarly, if computed value of k is of a polarity different from what was expected, then the direction of the pump may be reversed.

With the weigh scales 246, the controller 16 can perform on-line diagnostics even if the pumps are not moving fluid. For example, if the weigh scales 246 detect changes in weight when no flow is expected, then a leaky valve or a leak in the set 264 may be present.

In computing k and $T_{idle}$ and/or $T_{Pump}$ and/or $T_{Fill}$, the controller 16 may rely upon multiple measurements of $\Delta Wt$ and/or $\Delta T$. A variety of averaging or recursive techniques (e.g., recursive least means squares, Kalman filtering, etc.) may be used to decrease the error associated with the estimation schemes.

The above described monitoring technique is applicable for use for other constant stroke volume pumps, i.e. peristaltic pumps, etc.

2. Electrical Monitoring

Figure 42:
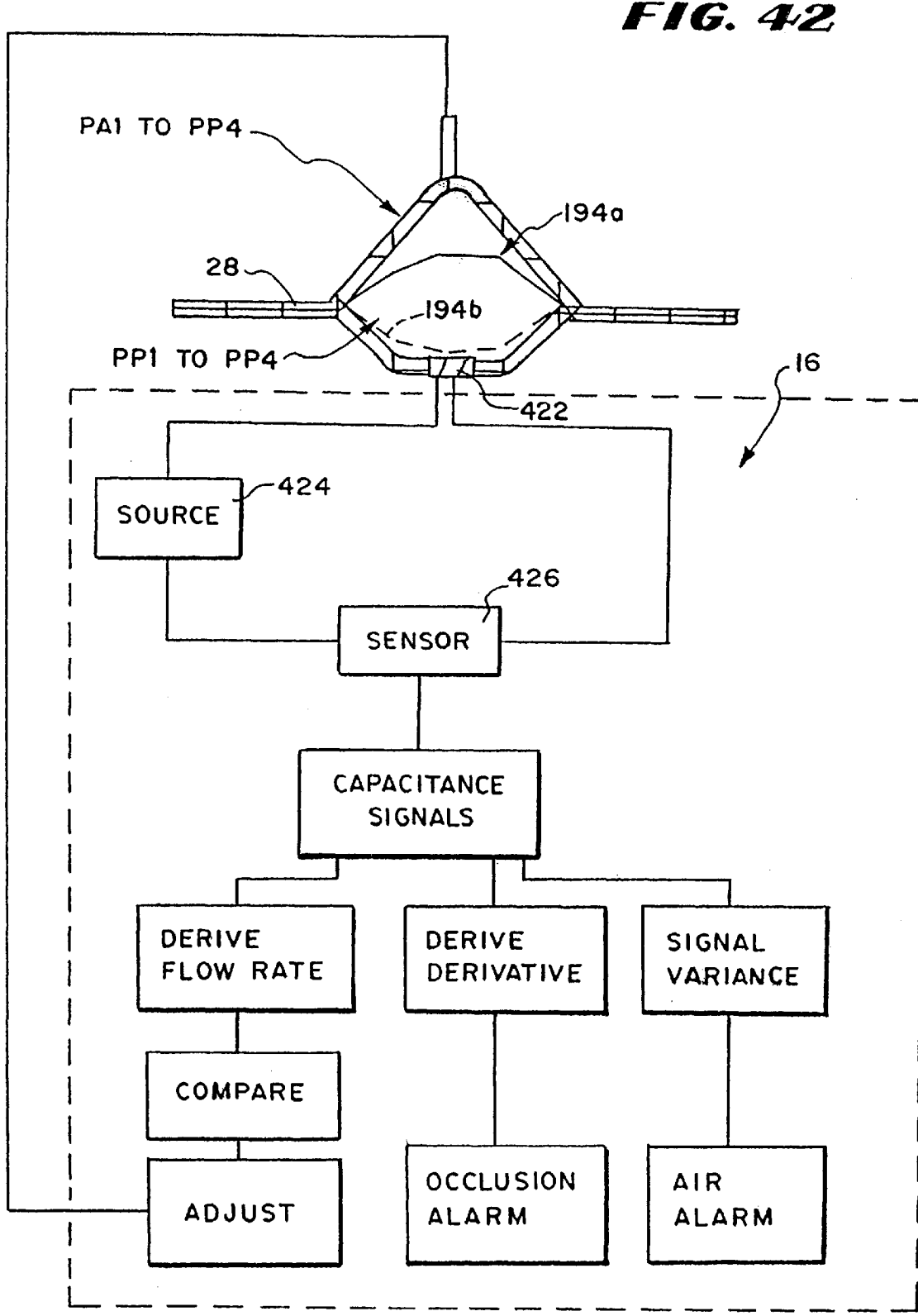
FIG. 42 is a schematic view of flow rate sensing and control system for a pneumatic pump chamber employing an electrode to create an electrical field inside the pump chamber.

In an alternative arrangement (see FIG. 42), the controller 16 includes a metal electrode 422 located in the chamber of each pump station PP1 to PP4 on the cassette 28. The electrodes 422 are coupled to a current source 424. The passage of current through each electrode 422 creates an electrical field within the respective pump chamber PP1 to PP4.

Cyclic deflection of the diaphragm 194 to draw fluid into and expel fluid from the pump chamber PP1 to PP4 changes the electrical field, resulting in a change in total capacitance of the circuit through the electrode 422. Capacitance increases as fluid is draw into the pump chamber PP1 to PP4, and capacitance decreases as fluid is expelled from pump chamber PP1 to PP4.

The controller 16 includes a capacitive sensor 426 (e.g., a Qprox E2S)coupled to each electrode 422. The capacitive sensor 426 registers changes in capacitance for the electrode 422 in each pump chamber PP1 to PP4. The capacitance signal for a given electrode 422 has a high signal magnitude when the pump chamber is filled with liquid (diaphragm position 194a), has a low signal magnitude signal when the pump chamber is empty of fluid (diaphragm position 194b), and has a range of intermediate signal magnitudes when the diaphragm occupies positions between position 194a and 194b.

At the outset of a blood processing procedure, the controller 16 calibrates the difference between the high and low signal magnitudes for each sensor to the maximum stroke volume SV of the respective pump chamber. The controller 16 then relates the difference between sensed maximum and minimum signal values during subsequent draw and expel cycles to fluid volume drawn and expelled through the pump chamber. The controller 16 sums the fluid volumes pumped over a sample time period to yield an actual flow rate.

The controller 16 compares the actual flow rate to a desired flow rate. If a deviance exists, the controller 16 varies pneumatic pressure pulses delivered to the actuator PA1 to PA4, to adjust $T_{Idle}$ and/or $T_{Pump}$ and/or $T_{Fill}$ to minimize the deviance.

The controller 16 also operates to detect abnormal operating conditions based upon the variations in the electric field and to generate an alarm output. In the illustrated embodiment, the controller 16 monitors for an increase in the magnitude of the low signal magnitude over time. The increase in magnitude reflects the presence of air inside a pump chamber.

In the illustrated embodiment, the controller 16 also generates a derivative of the signal output of the sensor 426. Changes in the derivative, or the absence of a derivative, reflects a partial or complete occlusion of flow through the pump chamber PP1 to PP4. The derivative itself also varies in a distinct fashion depending upon whether the occlusion occurs at the inlet or outlet of the pump chamber PP1 to PP4.

IV. The Blood Processing Procedures

A. Double RBC Collection Procedure (No Plasma Collection)

During this procedure, whole blood from a donor is centrifugally processed to yield up to two units (approximately 500 ml) of red blood cells for collection. All plasma constituent is returned to the donor. This procedure will, in shorthand, be called the double red blood cell collection procedure.

Prior to undertaking the double red blood cell collection procedure, as well as any blood collection procedure, the controller 16 operates the manifold assembly 226 to conduct an appropriate integrity check of the cassette 28, to determine whether there are any leaks in the cassette 28. Once the cassette integrity check is complete and no leaks are found, the controller 16 begins the desired blood collection procedure.

The double red blood cell collection procedure includes a pre-collection cycle, a collection cycle, a post-collection cycle, and a storage preparation cycle. During the pre-collection cycle, the set 264 is primed to vent air prior to venipuncture. During the collection cycle, whole blood drawn from the donor is processed to collect two units of red blood cells, while returning plasma to the donor. During the post-collection cycle, excess plasma is returned to the donor, and the set is flushed with saline. During the storage preparation cycle, a red blood cell storage solution is added.

1. The Pre-Collection Cycle a. Anticoagulant Prime

In a first phase of the pre-collection cycle (AC Prime 1), tube 300 leading to the phlebotomy needle 268 is clamped closed (see FIG. 10). The blood processing circuit 46 is programmed (through the selective application of pressure to the valves and pump stations of the cassette) to operate the donor interface pump PP3, drawing anticoagulant through the anticoagulant tube 270 and up the donor tube 266 through the y-connector 272 (i.e., in through valve V13 and out through valve V11). The circuit is further programmed to convey air residing in the anticoagulant tube 270, the donor tube 266, and the cassette and into the in-process container 312. This phase continues until an air detector 298 along the donor tube 266 detects liquid, confirming the pumping function of the donor interface pump PP3.

In a second phase of the pre-collection cycle (AC Prime 2), the circuit is programmed to operate the anticoagulant pump PP4 to convey anticoagulant into the in-process container 312. Weight changes in the in-process container 312. AC Prime 2 is terminated when the anticoagulant pump PP4 conveys a predetermined volume of anticoagulant (e.g., 10 g) into the in-process container 312, confirming is pumping function.

b. Saline Prime

In a third phase of the pre-collection cycle (Saline Prime 1), the processing chamber 46 remains stationary. The circuit is programmed to operate the in-process pump station PP1 to draw saline from the saline container 288 through the in-process pump PP1. This creates a reverse flow of saline through the stationary processing chamber 46 toward the in-process container 312. In this sequence saline is drawn through the processing chamber 46 from the saline container 288 into the in-process pump PP1 through valve V14. The saline is expelled from the pump station PP1 toward the in-process container 312 through valve 9. Weight changes in the saline container 288 are monitored. This phase is terminated upon registering a predetermined weight change in the saline container 288, which indicates conveyance of a saline volume sufficient to initially fill about one half of the processing chamber 46 (e.g., about 60 g).

With the processing chamber 46 about half full of priming saline, a fourth phase of the pre-collection cycle (Saline Prime 2). The processing chamber 46 is rotated at a low rate (e.g., about 300 RPM), while the circuit continues to operate in the same fashion as in Saline Prime 3. Additional saline is drawn into the pump station PP1 through valve V14 and expelled out of the pump station PP1 through valve V9 and into the in-process container 312. Weight changes in the in-process container 312 are monitored. This phase is terminated upon registering a predetermined weight change in the in-process container 312, which indicates the conveyance of an additional volume of saline sufficient to substantially fill the processing chamber 46 (e.g., about 80 g).

In a fifth phase of the pre-collection cycle (Saline Prime 3), the circuit is programmed to first operate the in-process pump station PP1 to convey saline from the in-process container 312 through all outlet ports of the separation device and back into the saline container 288 through the plasma pump station PP2. This completes the priming of the processing chamber 46 and the in-process pump station PP1 (pumping in through valve V9 and out through valve V14), as well as primes the plasma pump station PP2, with the valves V7, V6, V10, and V12 opened to allow passive flow of saline. During this time, the rate at which the processing chamber 46 is rotated is successively ramped between zero and 300 RPM. Weight changes in the in process container 312 are monitored. When a predetermined initial volume of saline is conveyed in this manner, the circuit is programmed to close valve V7, open valves V9 and V14, and to commence pumping saline to the saline container 288 through the plasma pump PP2, in through valve V12 and out through valve V10, allowing saline to passively flow through the in-process pump PP1. Saline in returned in this manner from the in-process container 312 to the saline container 288 until weight sensing indicated that a preestablished minimum volume of saline occupies the in-process container 312.

In a sixth phase of the pre-collection cycle (Vent Donor Line), the circuit is programmed to purge air from the venepuncture needle, prior to venipuncture, by operating the donor interface pump PP3 to pump anticoagulant through anticoagulant pump PP4 and into the in process container 312.

In a seventh phase of the pre-collection cycle (Venipuncture), the circuit is programmed to close all valves V1 to V23, so that venipuncture can be accomplished.

The programming of the circuit during the phases of the pre-collection cycle is summarized in the following table.

TABLE

Programming of Blood Processing Circuit During Pre-Collection Cycle
(Double Red Blood Cell Collection Procedure)

| Phase | AC Prime 1 | AC Prime 2 | Saline Prime 1 | Saline Prime 2 | Saline Prime 3 | Vent Donor Line | Veni-puncture |
|---|---|---|---|---|---|---|---|
| V1 | ● | ● | ● | ● | ● | ● | ● |
| V2 | ● | ● | ● | ● | ● | ● | ● |
| V3 | ○ | ○ | ● | ● | ● | ○ | ● |
| V4 | ● | ● | ○ | ● | ● | ● | ● |
| V5 | ● | ● | ● | ● | ● | ● | ● |
| V6 | ● | ● | ● | ● | ○ | ● | ● |
| V7 | ● | ● | ● | ● | ○ | ● | ● |
| V8 | ● | ● | ● | ● | ● | ● | ● |
| V9 | ● | ● | ○/● Pump Out | ○/● Pump Out | ○/● Pump In (Stage 1) ○ (Stage 2) | ● | ● |
| V10 | ● | ● | ● | ● | ○ (Stage 1) ○/● Pump Out (Stage 2) | ● | ● |
| V11 | ○/● Pump Out | ○ | ● | ● | ● | ○/● Pump In | ● |
| V12 | ● | ● | ● | ● | ○ (Stage 1) ○/● Pump In (Stage 2) | ● | ● |
| V13 | ○/● Pump In | ○ | ● | ● | ● | ○/● Pump Out | ● |
| V14 | ● | ● | ○/● Pump In | ○/● Pump In | ○/● Pump Out (Stage 1) ○ (Stage 2) | ● | ● |
| V15 | ○ | ○/● Pump In Pump Out | ● | ● | ● | ○ | ● |
| V16 | ● | ● | ● | ● | ● | ● | ● |
| V17 | ● | ● | ● | ● | ● | ● | ● |
| V18 | ○ | ○ | ● | ● | ● | ○ | ● |
| V19 | ○ | ○ | ● | ● | ● | ○ | ● |
| V20 | ○ | ○/● Pump Out Pump In | ● | ● | ● | ○ | ● |
| V21 | ● | ● | ● | ● | ● | ● | ● |
| V22 | ● | ● | ○ | ○ | ○ | ● | ● |
| V23 | ● | ● | ○ | ○ | ○ | ● | ● |
| PP1 | ■ | ■ | □ | □ | □ (Stage 1) | ■ | ■ |
| PP2 | ■ | ■ | ■ | ■ | □ (Stage 2) | ■ | ■ |

TABLE-continued

Programming of Blood Processing Circuit During Pre-Collection Cycle
(Double Red Blood Cell Collection Procedure)

| Phase | AC Prime 1 | AC Prime 2 | Saline Prime 1 | Saline Prime 2 | Saline Prime 3 | Vent Donor Line | Veni-puncture |
|---|---|---|---|---|---|---|---|
| PP3 | □ | ● | ● | ● | ● | ○ | ● |
| PP4 | ● | □ | ● | ● | ● | ● | ● |

Caption:
○ denotes an open valve;
● denotes a closed valve;
○/● denotes a valve opening and closing during a pumping sequence;
■ denotes an idle pump station (not in use); and
□ denotes a pump station in use.

c. The Collection Cycle
i. Blood Prime

With venipuncture, tube 300 leading to the phlebotomy needle 268 is opened. In a first phase of the collection cycle (Blood Prime 1), the blood processing circuit 46 is programmed (through the selective application of pressure to the valves and pump stations of the cassette) to operate the donor interface pump PP3 (i.e., in through valve V13 and out through valve V11) and the anticoagulant pump PP4 (i.e., in through valve V20 and out through valve V15) to draw anticoagulated blood through the donor tube 270 into the in process container 312. This phase continues until an incremental volume of anticoagulated whole blood enters the in process container 312, as monitored by the weigh sensor.

In a next phase (Blood Prime 'n2), the blood processing circuit 46 is programmed to operate the in-process pump station PP1 to draw anticoagulated blood from the in-process container 312 through the separation device. During this phase, saline displaced by the blood is returned to the donor. This phase primes the separation device with anticoagulated whole blood. This phase continues until an incremental volume of anticoagulated whole blood leaves the in process container 312, as monitored by the weigh sensor.

B. Blood Separation While Drawing Whole Blood or Without Drawing Whole Blood

In a next phase of the blood collection cycle (Blood Separation While Drawing Whole Blood), the blood processing circuit 46 is programmed to operate the donor interface pump station PP3 (i.e., in through valve V13 and out through valve V11); the anticoagulant pump PP4 (i.e., in through valve V20 and out through valve V15); the in-process pump PP1 (i.e., in through valve V9 and out through valve V14); and the plasma pump PP2 (i.e., in through valve V12 and out through valve V10). This arrangement draws anticoagulated blood into the in-process container 312, while conveying the blood from the in-process container 312 into the processing chamber for separation. This arrangement also removes plasma from the processing chamber into the plasma container 304, while removing red blood cells from the processing chamber into the red blood cell container 308. This phase continues until an incremental volume of plasma is collected in the plasma collection container 304 (as monitored by the weigh sensor) or until a targeted volume of red blood cells is collected in the red blood cell collection container (as monitored by the weigh sensor).

If the volume of whole blood in the in-process container 312 reaches a predetermined maximum threshold before the targeted volume of either plasma or red blood cells is collected, the circuit is programmed for another phase (Blood Separation Without Drawing Whole Blood), to terminate operation of the donor interface pump station PP3 (while also closing valves V13, V11, V18, and V13) to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the circuit is programmed to return to the Blood Separation While Drawing Whole Blood Phase, to thereby allow whole blood to enter the in-process container 312. The circuit is programmed to toggle between the Blood Separation While Drawing Whole Blood Phase and the Blood Separation Without Drawing Whole Blood Phase according to the high and low volume thresholds for the in-process container 312, until the requisite volume of plasma has been collected, or until the target volume of red blood cells has been collected, whichever occurs first.

C. Return Plasma and Saline

If the targeted volume of red blood cells has not been collected, the next phase of the blood collection cycle (Return Plasma With Separation) programs the blood processing circuit 46 to operate the donor interface pump station PP3 (i.e., in through valve V11 and out through valve V13); the in-process pump PP1 (i.e., in through valve V9 and out through valve V14); and the plasma pump PP2 (i.e., in through valve V12 and out through valve V10). This arrangement conveys anticoagulated whole blood from the in-process container 312 into the processing chamber for separation, while removing plasma into the plasma container 304 and red blood cells into the red blood cell container 308. This arrangement also conveys plasma from the plasma container 304 to the donor, while also mixing saline from the container 288 in line with the returned plasma. The in line mixing of saline with plasma raises the saline temperature and improves donor comfort. This phase continues until the plasma container 304 is empty, as monitored by the weigh sensor.

If the volume of whole blood in the in-process container 312 reaches a specified low threshold before the plasma container 304 empties, the circuit is programmed to enter another phase (Return Plasma Without Separation), to terminate operation of the in-process pump station PP1 (while also closing valves V9, V10, V12, and V14) to terminate blood separation. The phase continues until the plasma container 304 empties.

Upon emptying the plasma container 304, the circuit is programmed to enter a phase (Fill Donor Line), to operate the donor interface pump station PP3 (i.e., in through valve V11 and out through valve V13) to draw whole blood from the in process container 312 to fill the donor tube 266, thereby purge plasma (mixed with saline) in preparation for another draw whole blood cycle.

The circuit is then programmed to conduct another Blood Separation While Drawing Whole Blood Phase, to refill the in process container 312. The circuit is programmed in successive Blood Separation and Return Plasma Phases until the weigh sensor indicates that a desired volume of red blood cells have been collected in the red blood cell collection container 308. When the targeted volume of red blood cells has not been collected, the post-collection cycle commences.

The programming of the circuit during the phases of the collection cycle is summarized in the following table.

D. The Post-Collection Cycle

Once the targeted volume of red blood cells has been collected (as monitored by the weigh sensor), the circuit is programmed to carry out the phases of the post-collection cycle.

1. Return Excess Plasma

In a first phase of the post-collection cycle (Excess Plasma Return), the circuit is programmed to terminate the supply and removal of blood to and from the processing chamber, while operating the donor interface pump station PP3 (i.e., in through valve V11 and out through valve V13) to convey plasma remaining in the plasma container 304 to the donor. The circuit is also programmed in this phase to

TABLE

Programming of Blood Processing Circuit During The Collection Cycle
(Double Red Blood Cell Collection Procedure)

| Phase | Blood Prime 1 | Blood Prime 2 | Blood Separation While Drawing Whole Blood (Without Drawing Whole Blood) | Return Plasma/ with Separation (Without Separation) | Fill Donor Line |
|---|---|---|---|---|---|
| V1 | ● | ● | ● | ● | ○ |
| V2 | ● | ● | ○ | ○ (●) | ● |
| V3 | ○ | ● | ○ (●) | ● | ● |
| V4 | ● | ● | ● | ● | ● |
| V5 | ● | ● | ○ | ○ | ● |
| V6 | ● | ● | ● | ○/● Alternates with V23 | ● |
| V7 | ● | ○ | ● | ● | ○ |
| V8 | ● | ● | ● | ● | ● |
| V9 | ● | ○/● Pump In | ○/● Pump In | ○/● Pump In (●) | ● |
| V10 | ● | ● | ○/● Pump Out | ○/● Pump Out (●) | ● |
| V11 | ○/● Pump Out | ○ | ○/● Pump Out (●) | ○/● Pump In | ○/● Pump In |
| V12 | ● | ● | ○/● Pump In | ○/● Pump In (●) | ● |
| V13 | ○/● Pump In | ○ | ○/● Pump In (●) | ○/● Pump Out | ○/● Pump Out |
| V14 | ● | ○/● Pump Out | ○/● Pump Out | ○/● Pump Out (●) | ● |
| V15 | ○/● Pump Out | ● | ○/● Pump Out (●) | ● | ● |
| V16 | ● | ● | ● | ● | ● |
| V17 | ● | ● | ● | ● | ● |
| V18 | ○ | ○ | ○ (●) | ○ | ○ |
| V19 | ○ | ● | ○ (●) | ● | ● |
| V20 | ○/● Pump Out | ● | ○/● Pump In (●) | ● | ● |
| V21 | ● | ● | ● | ● | ● |
| V22 | ● | ● | ● | ○ | ● |
| V23 | ● | ● | ● | ○/● Alternates with V6 | ● |
| PP1 | ■ | □ | □ | □ (■) | ■ |
| PP2 | ■ | ■ | □ | □ (■) | ■ |
| PP3 | □ | ■ | □ (■) | □ | □ |
| PP4 | □ | ■ | □ (■) | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

mix saline from the container 288 in line with the returned plasma. This phase continues until the plasma container 304 is empty, as monitored by the weigh sensor.

2. Saline Purge

In the next phase of the post-collection cycle (Saline Purge), the circuit is programmed to operate the donor interface pump station PP3 (i.e., in through valve V11 and out through valve V11) to convey saline from the container 288 through the separation device, to displace the blood contents of the separation device into the in-process container 312, in preparation for their return to the donor. This phase reduces the loss of donor blood. This phase continues until a predetermined volume of saline is pumped through the separation device, as monitored by the weigh sensor.

3. Final Return to Donor

In the next phase of the post-collection cycle (Final Return), the circuit is programmed to operate the donor interface pump station PP3 (i.e., in through valve V11 and out through valve V13) to convey the blood contents of the in-process container 312 to the donor. Saline is intermittently mixed with the blood contents. This phase continues until the in-process container 312 is empty, as monitored by the weigh sensor.

In the next phase (Fluid Replacement), the circuit is programmed to operate the donor interface pump station PP3 (i.e., in through valve V11 and out through valve V13) to convey the saline to the donor. This phase continues until a prescribed replacement volume amount is infused, as monitored by the weigh sensor.

In the next phase of the post-collection cycle (Empty In Process Container), the circuit is programmed to operate the donor interface pump station PP3 (i.e., in through valve V11 and out through valve V13) to convey all remaining contents of the in-process container 312 to the donor, in preparation of splitting the contents of the red blood cell container 308 for storage in both containers 308 and 312. This phase continues until a zero volume reading for the in-process container 312 occurs, as monitored by the weigh sensor, and air is detected at the air detector.

At this phase, the circuit is programmed to close all valves and idle all pump stations, so that the phlebotomy needle 268 can be removed from the donor.

The programming of the circuit during the phases of the post-collection cycle is summarized in the following table.

TABLE

Programming of Blood Processing Circuit During The Post-Collection Cycle (Double Red Blood Cell Collection Procedure)

| Phase | Excess Plasma Return | Saline Purge | Final Return | Fluid Replacement | Empty In Process Container |
|---|---|---|---|---|---|
| V1 | ● | ● | ○ | ● | ○ |
| V2 | ● | ● | ● | ● | ● |
| V3 | ● | ● | ● | ● | ● |
| V4 | ● | ○ | ● | ● | ● |
| V5 | ○ | ● | ● | ● | ● |
| V6 | ○/● Alternates with V23 | ● | ● | ● | ● |
| V7 | ● | ● | ○/● Alternates with V23 | ● | ○ |
| V8 | ● | ● | ● | ● | ● |
| V9 | ○ | ○ | ● | ● | ● |
| V10 | ● | ● | ● | ● | ● |

TABLE-continued

Programming of Blood Processing Circuit During The Post-Collection Cycle (Double Red Blood Cell Collection Procedure)

| Phase | Excess Plasma Return | Saline Purge | Final Return | Fluid Replacement | Empty In Process Container |
|---|---|---|---|---|---|
| V11 | ○/● Pump In | ○/● Pump In/Pump Out | ○/● Pump In | ○/● Pump In | ○/● Pump In |
| V12 | ● | ● | ● | ● | ● |
| V13 | ○/● Pump Out | ● | ○/● Pump Out | ○/● Pump Out | ○/● Pump Out |
| V14 | ● | ○ | ● | ● | ● |
| V15 | ● | ● | ● | ● | ● |
| V16 | ● | ● | ● | ● | ● |
| V17 | ● | ● | ● | ● | ● |
| V18 | ○ | ● | ○ | ○ | ○ |
| V19 | ● | ● | ● | ● | ● |
| V20 | ● | ● | ● | ● | ● |
| V21 | ● | ● | ● | ● | ● |
| V22 | ○ | ○ | ○ | ○ | ● |
| V23 | ○/● Alternates with V6 | ○ | ○/● Alternates with V7 | ○ | ● |
| PP1 | ■ | ■ | ■ | ■ | ■ |
| PP2 | ■ | ■ | ■ | ■ | ■ |
| PP3 | □ | □ | □ | □ | □ |
| PP4 | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

E. The Storage Preparation Cycle

1. Split RBC

In the first phase of the storage preparation cycle (Split RBC), the circuit is programmed to operate the donor interface pump station PP3 to transfer half of the contents of the red blood cell collection container 308 into the in-process container 312. The volume pumped is monitored by the weigh sensors for the containers 308 and 312.

2. Add RBC Preservative

In the next phases of the storage preparation cycle (Add Storage Solution to the In Process Container and Add Storage Solution to the Red Blood Cell Collection Container), the circuit is programmed to operate the donor interface pump station PP3 to transfer a desired volume of red blood cell storage solution from the container 280 first into the in-process container 312 and then into the red blood cell collection container 308. The transfer of the desired volume is monitored by the weigh scale.

In the next and final phase (End Procedure), the circuit is programmed to close all valves and idle all pump stations, so that the red blood cell containers 308 and 312 can be separated and removed for storage. The remainder of the disposable set can now be removed and discarded.

The programming of the circuit during the phases of the storage preparation cycle is summarized in the following table.

TABLE

Programming of Blood Processing Circuit During The Storage Preparation Cycle
(Double Red Blood Cell Collection Procedure)

| Phase | Split RBC Between RBC Collection and In Process Containers | Add Storage Solution to In Process Container | Add Storage Solution to RBC Collection Container | End Procedure (Remove Venipuncture) |
|---|---|---|---|---|
| V1 | ● | ● | ● | ● |
| V2 | ○ | ● | ○ | ● |
| V3 | ○/● Alternates with V11 and V4 | ○ | ● | ● |
| V4 | ○/● Alternates with V11 and V4 | ● | ○ | ● |
| V5 | ● | ● | ● | ● |
| V6 | ● | ● | ● | ● |
| V7 | ● | ● | ● | ● |
| V8 | ● | ●● | ● | ● |
| V9 | ● | ● | ● | ● |
| V10 | ● | ●● | ● | ● |
| V11 | ○/● Pump In/ Pump Out | ○/● Pump In/ Pump Out | ○/● Pump In/ Pump Out | ● |
| V12 | ● | ● | ● | ● |
| V13 | ● | ● | ● | ● |
| V14 | ● | ● | ● | ● |
| V15 | ● | ● | ● | ● |
| V16 | ● | ○ | ○ | ● |
| V17 | ● | ● | ● | ● |
| V18 | ● | ● | ● | ● |
| V19 | ● | ● | ● | ● |
| V20 | ● | ● | ● | ● |
| V21 | ● | ○ | ○ | ● |
| V22 | ● | ● | ● | ● |
| V23 | ● | ● | ● | ● |
| PP1 | ■ | ■ | ■ | ■ |
| PP2 | ■ | ■ | ■ | ■ |
| PP3 | □ | □ | □ | ■ |
| PP4 | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

F. Plasma Collection (No Red Blood Cell Collection)

During this procedure, whole blood from a donor is centrifugally processed to yield up to 880 ml of plasma for collection. All red blood cells are returned to the donor. This procedure will, in shorthand, be called the plasma collection procedure.

Programming of the blood processing circuit 46(through the selective application of pressure to the valves and pump stations of the cassette) makes it possible to use the same universal set 264 as in the double red blood cell collection procedure.

The procedure includes a pre-collection cycle, a collection cycle, and a post-collection cycle.

During the pre-collection cycle, the set 264 is primed to vent air prior to venipuncture. During the collection cycle, whole blood drawn from the donor is processed to collect plasma, while returning red blood cells to the donor. During the post-collection cycle, excess plasma is returned to the donor, and the set is flushed with saline.

1. The Pre-Collection Cycle a. Anticoagulant Prime

In the pre-collection cycle for the plasma collection (no red blood cells) procedure, the cassette is programmed to carry out AC Prime 1 and AC Prime 2 Phases that are identical to the AC Prime 1 and AC Prime 2 Phases of the double red blood cell collection procedure.

b. Saline Prime

In the pre-collection cycle for the plasma collection (no red blood cell) procedure, the cassette is programmed to carry out Saline Prime 1, Saline Prime 2, Saline Prime 3, Vent Donor Line, and Venipuncture Phases that are identical to the Saline Prime 1, Saline Prime 2, Saline Prime 3, Vent Donor Line, and Venipuncture Phases of the double red blood cell collection procedure.

The programming of the circuit during the phases of the pre-collection cycle is summarized in the following table.

TABLE

Programming of Blood Processing Circuit During Pre-Collection Phase
(Plasma Collection Procedure)

| Phase | AC Prime 1 | AC Prime 2 | Saline Prime 1 | Saline Prime 2 | Saline Prime 3 | Vent Donor Line | Venipuncture |
|---|---|---|---|---|---|---|---|
| V1 | ● | ● | ● | ● | ● | ● | ● |
| V2 | ● | ● | ● | ● | ● | ● | ● |
| V3 | ○ | ○ | ● | ● | ● | ○ | ● |
| V4 | ● | ● | ○ | ● | ● | ● | ● |
| V5 | ● | ● | ● | ● | ● | ● | ● |
| V6 | ● | ● | ● | ● | ○ | ● | ● |
| V7 | ● | ● | ● | ● | ○ | ● | ● |
| V8 | ● | ● | ● | ● | ● | ● | ● |
| V9 | ● | ● | ○/● Pump Out | ○/● Pump Out | ○/● Pump In (Stage 1) ○ (Stage 2) | ● | ● |

TABLE-continued

Programming of Blood Processing Circuit During Pre-Collection Phase
(Plasma Collection Procedure)

| Phase | AC Prime 1 | AC Prime 2 | Saline Prime 1 | Saline Prime 2 | Saline Prime 3 | Vent Donor Line | Veni-puncture |
|---|---|---|---|---|---|---|---|
| V10 | ● | ● | ● | ● | ○ (Stage 1) ○/● Pump Out (Stage 2) | ● | ● |
| V11 | ○/● Pump Out | ○ | ● | ● | ● | ○/● Pump In | ● |
| V12 | ● | ● | ● | ● | ○ (Stage 1) ○/● Pump In (Stage 2) | ● | ● |
| V13 | ○/● Pump In | ○ | ● | ● | ● | ○/● Pump Out | ● |
| V14 | ● | ● | ○/● Pump In | ○/● Pump In | ○/● Pump Out (Stage 1) ○ (Stage 2) | ● | ● |
| V15 | ○ | ○/● Pump In Pump Out | ● | ● | ● | ○ | ● |
| V16 | ● | ● | ● | ● | ● | ● | ● |
| V17 | ● | ● | ● | ● | ● | ● | ● |
| V18 | ○ | ○ | ● | ● | ● | ○ | ● |
| V19 | ○ | ○ | ● | ● | ● | ○ | ● |
| V20 | ○ | ○/● Pump Out Pump In | ● | ● | ● | ○ | ● |
| V21 | ● | ● | ● | ● | ● | ● | ● |
| V22 | ● | ● | ○ | ○ | ○ | ● | ● |
| V23 | ● | ● | ○ | ○ | ○ | ● | ● |
| PP1 | ■ | ■ | □ | □ | □ (Stage 1) | ■ | ■ |
| PP2 | ■ | ■ | ■ | ■ | □ (Stage 2) | ■ | ■ |
| PP3 | □ | ■ | ■ | ■ | ■ | □ | ■ |
| PP4 | ■ | □ | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

2. The Collection Cycle a. Blood Prime

With venipuncture, tube 300 leading to the phlebotomy needle 268 is opened. In a first phase of the collection cycle (Blood Prime 1), the blood processing circuit 46 is programmed to operate the donor interface pump PP3 (i.e., in through valve V13 and out through valve V11) and the anticoagulant pump PP4 (i.e., in through valve V20 and out through valve V15) to draw anticoagulated blood through the donor tube 270 into the in process container 312, in the same fashion as the Blood Prime 1 Phase of the the double red blood cell collection procedure, as already described.

In a next phase (Blood Prime 2), the blood processing circuit 46 is programmed to operate the in-process pump station PP1 to draw anticoagulated blood from the in-process container 312 through the separation device, in the same fashion as the Blood Prime 2 Phase for the double red blood cell collection procedure, as already described. During this phase, saline displaced by the blood is returned to the donor.

b. Blood Separation While Drawing Whole Blood or Without Drawing Whole Blood

In a next phase of the blood collection cycle (Blood Separation While Drawing Whole Blood), the blood processing circuit 46 is programmed to operate the donor interface pump station PP3 (i.e., in through valve V13 and out through valve V11); the anticoagulant pump PP4 (i.e., in through valve V20 and out through valve V15); the in-process pump PP1 (i.e., in through valve V9 and out through valve V14); and the plasma pump PP2 (i.e., in through valve V12 and out through valve V10), in the same fashion as the Blood Separation While Drawing Whole Blood Phase for the double red blood cell collection procedure, as already described. This arrangement draws anticoagulated blood into the in-process container 312, while conveying the blood from the in-process container 312 into the processing chamber for separation. This arrangement also removes plasma from the processing chamber into the plasma container 304, while removing red blood cells from the processing chamber into the red blood cell container 308. This phase continues until the targeted volume of plasma is collected in the plasma collection container 304

(as monitored by the weigh sensor) or until a targeted volume of red blood cells is collected in the red blood cell collection container (as monitored by the weigh sensor).

As in the double red blood cell collection procedure, if the volume of whole blood in the in-process container 312 reaches a predetermined maximum threshold before the targeted volume of either plasma or red blood cells is collected, the circuit is programmed to enter another phase (Blood Separation Without Drawing Whole Blood), to terminate operation of the donor interface pump station PP3 (while also closing valves V13, V11, V18, and V13) to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the circuit is programmed to return to the Blood Separation While Drawing Whole Blood Phase, to thereby refill the in-process container 312. The circuit is programmed to toggle between the Blood Separation Phases while drawing whole blood and without drawing whole blood, according to the high and low volume thresholds for the in- process container 312, until the requisite volume of plasma has been collected, or until the target volume of red blood cells has been collected, whichever occurs first.

C. Return Red Blood Cells /Saline

If the targeted volume of plasma has not been collected, the next phase of the blood collection cycle (Return Red Blood Cells With Separation) programs the blood processing circuit 46 to operate the donor interface pump station PP3 (i.e., in through valve V11 and out through valve V13); the in-process pump PP1 (i.e., in through valve V9 and out through valve V14); and the plasma pump PP2 (i.e., in through valve V12 and out through valve V10). This arrangement conveys anticoagulated whole blood from the in-process container 312 into the processing chamber for separation, while removing plasma into the plasma container 304 and red blood cells into the red blood cell container 308.

This arrangement also conveys red blood cells from the red blood cell container 308 to the donor, while also mixing saline from the container 288 in line with the returned red blood cells. The in line mixing of saline with the red blood cells raises the saline temperature and improves donor comfort. The in line mixing of saline with the red blood cells also lowers the hematocrit of the red blood cells being returned to the donor, thereby allowing a larger gauge (i.e., smaller diameter) phlebotomy needle to be used, to further improve donor comfort. This phase continues until the red blood cell container 308 is empty, as monitored by the weigh sensor.

If the volume of whole blood in the in-process container 312 reaches a specified low threshold before the red blood cell container 308 empties, the circuit is programmed to enter another phase (Red Blood Cell Return Without Separation), to terminate operation of the in-process pump station PP1 (while also closing valves V9, V10, V12, and V14) to terminate blood separation. The phase continues until the red blood cell container 308 empties.

Upon emptying the red blood cell container 308, the circuit is programmed to enter another phase (Fill Donor Line), to operate the donor interface pump station PP3 (i.e., in through valve V11 and out through valve V13) to draw whole blood from the in process container 312 to fill the donor tube 266, thereby purge red blood cells (mixed with saline) in preparation for another draw whole blood cycle.

The circuit is then programmed to conduct another Blood Separation While Drawing Whole Blood Phase, to refill the in process container 312. The circuit is programmed to conduct successive draw whole blood and return red blood cells/saline cycles, as described, until the weigh sensor indicates that a desired volume of plasma has been collected in the plasma collection container 304. When the targeted volume of plasma has been collected, the post-collection cycle commences.

The programming of the circuit during the phases of the collection cycle is summarized in the following table.

TABLE

Programming of Blood Processing Circuit During The Collection Cycle
(Plasma Collection Procedure)

| Phase | Blood Prime 1 | Blood Prime 2 | Blood Separation While Drawing Whole Blood (Without Drawing Whole Blood) | Return Red Blood Cells/Saline with Separation (Without Separation) | Fill Donor Line |
|---|---|---|---|---|---|
| V1 | ● | ● | ● | ● | ○ |
| V2 | ● | ● | ○ | ○ | ● |
| V3 | ○ | ● | ○ (●) | ● | ● |
| V4 | ● | ● | ● | ● | ● |
| V5 | ● | ● | ○ | ○ (●) | ● |
| V6 | ● | ● | ● | ● | ● |
| V7 | ● | ○ | ● | ○/● Alternates with V23 | ○ |
| V8 | ● | ● | ● | ● | ● |
| V9 | ● | ○/● Pump In | ○/● Pump In | ○/● Pump In (●) | ● |
| V10 | ● | ● | ○/● Pump Out | ○/● Pump Out (●) | ● |
| V11 | ○/● Pump Out | ○ | ○/● Pump Out (●) | ○/● Pump In | ○/● Pump In |
| V12 | ● | ● | ○/● Pump In | ○/● Pump In (●) | ● |

TABLE-continued

Programming of Blood Processing Circuit During The Collection Cycle
(Plasma Collection Procedure)

| Phase | Blood Prime 1 | Blood Prime 2 | Blood Separation While Drawing Whole Blood (Without Drawing Whole Blood) | Return Red Blood Cells/Saline with Separation (Without Separation) | Fill Donor Line |
|---|---|---|---|---|---|
| V13 | o/● Pump In | o | o/● Pump In (●) | o/● Pump Out | o/● Pump Out |
| V14 | ● | o/● Pump Out | o/● Pump Out | o/● Pump Out (●) | ● |
| V15 | o/● Pump Out | ● | o/● Pump Out (●) | ● | ● |
| V16 | ● | ● | ● | ● | ● |
| V17 | ● | ● | ● | ● | ● |
| V18 | o | o | o (●) | o | o |
| V19 | o | ● | o (●) | ● | ● |
| V20 | o/● Pump Out | ● | o/● Pump In (●) | ● | ● |
| V21 | ● | ● | ● | ● | ● |
| V22 | ● | ● | ● | o | ● |
| V23 | ● | ● | ● | o/● Alternates with V7 | ● |
| PP1 | ■ | □ | □ | □ (■) | ■ |
| PP2 | ■ | ■ | □ | □ (■) | ■ |
| PP3 | □ | ■ | □ (■) | □ | □ |
| PP4 | □ | ■ | □ (■) | ■ | ■ |

Caption:
o denotes an open valve;
● denotes a closed valve;
o/● denotes a valve opening and closing during a pumping sequence;
■ denotes an idle pump station (not in use); and
□ denotes a pump station in use.

d. The Post-Collection Cycle

Once the targeted volume of plasma has been collected (as monitored by the weigh sensor), the circuit is programmed to carry out the phases of the post-collection cycle.

3. Return Excess Red Blood Cells

In a first phase of the post-collection cycle (Remove Plasma Collection Container), the circuit is programmed to close all valves and disable all pump stations to allow separation of the plasma collection container 304 from the set 264.

In the second phase of the post-collection cycle (Return Red Blood Cells), the circuit is programmed to operate the donor interface pump station PP3 (i.e., in through valve V11 and out through valve V13) to convey red blood cells remaining in the red blood cell collection container 308 to the donor. The circuit is also programmed in this phase to mix saline from the container 288 in line with the returned red blood cells. This phase continues until the red blood cell container 308 is empty, as monitored by the weigh sensor.

4. Saline Purge

In the next phase of the post-collection cycle (Saline Purge), the circuit is programmed to operate the donor interface pump station PP3 (i.e., in through valve V11 and out through valve V11) to convey saline from the container 288 through the separation device, to displace the blood contents of the separation device into the in-process container 312, in preparation for their return to the donor. This phase reduces the loss of donor blood. This phase continues until a predetermined volume of saline in pumped through the separation device, as monitored by the weigh sensor.

5. Final Return to Donor

In the next phase of the post-collection cycle (Final Return), the circuit is programmed to operate the donor interface pump station PP3 (i.e., in through valve V11 and out through valve V13) to convey the blood contents of the in-process container 312 to the donor. Saline is intermittently mixed with the blood contents. This phase continues until the in-process container 312 is empty, as monitored by the weigh sensor.

In the next phase (Fluid Replacement), the circuit is programmed to operate the donor interface pump station PP3 (i.e., in through valve V11 and out through valve V13) to convey the saline to the donor. This phase continues until a prescribed replacement volume amount is infused, as monitored by the weigh sensor.

In the final phase (End Procedure), the circuit is programmed to close all valves and idle all pump stations, so that venipuncture can be terminated, and the plasma container can be separated and removed for storage. The remaining parts of the disposable set can be removed and discarded.

The programming of the circuit during the phases of the post-collection cycle is summarized in the following table.

TABLE

Programming of Blood Processing Circuit During The Post-Collection Cycle (Plasma Collection Procedure)

| Phase | Remove Plasma Collection Container | Return RBC | Saline Purge | Final Return | Fluid Replacement | End Procedure |
|---|---|---|---|---|---|---|
| V1 | ● | ● | ● | ○ | ● | ● |
| V2 | ● | ○ | ● | ● | ● | ● |
| V3 | ● | ● | ● | ● | ● | ● |
| V4 | ● | ● | ○ | ● | ● | ● |
| V5 | ● | ● | ● | ● | ● | ● |
| V6 | ● | ● | ● | ● | ● | ● |
| V7 | ● | ○/● Alternates with V23 | ● | ○/● Alternates with V23 | ● | ● |
| V8 | ● | ● | ● | ● | ● | ● |
| V9 | ● | ○ | ○ | ● | ● | ● |
| V10 | ● | ● | ● | ● | ● | ● |
| V11 | ● | ○/● Pump In | ○/● Pump In/Pump Out | ○/● Pump In | ○/● Pump In | ● |
| V12 | ● | ● | ● | ● | ● | ● |
| V13 | ● | ○/● Pump Out | ● | ○/● Pump Out | ○/● Pump Out | ● |
| V14 | ● | ● | ○ | ● | ● | ● |
| V15 | ● | ● | ● | ● | ● | ● |
| V16 | ● | ● | ● | ● | ● | ● |
| V17 | ● | ● | ● | ● | ● | ● |
| V18 | ● | | ● | ○ | ○ | ● |
| V19 | ● | ● | ● | ● | ● | ● |
| V20 | ● | ● | ● | ● | ● | ● |
| V21 | ● | ● | ● | ● | ● | ● |
| V22 | ● | ○ | ○ | ○ | ○ | ● |
| V23 | ● | ○/● Alternates with V6 | ○ | ○/● Alternates with V7 | ○ | ● |
| PP1 | ■ | ■ | ■ | ■ | ■ | ■ |
| PP2 | ■ | ■ | ■ | ■ | ■ | ■ |
| PP3 | ■ | □ | □ | □ | □ | |
| PP4 | ■ | ■ | ■ | ■ | ■ | |

Caption:
○ denotes an open valve;
● denotes a closed valve;
○/● denotes a valve opening and closing during a pumping sequence;
■ denotes an idle pump station (not in use); and
□ denotes a pump station in use.

G. Red Blood Cell and Plasma Collection

During this procedure, whole blood from a donor is centrifugally processed to collect up to about 550 ml of plasma and up to about 250 ml of red blood cells. This procedure will, in shorthand, be called the red blood cell/plasma collection procedure.

The portion of the red blood cells not retained for collection are periodically returned to the donor during blood separation. Plasma collected in excess of the 550 ml target and red blood cells collected in excess of the 250 ml target are also returned to the donor at the end of the procedure.

Programming of the blood processing circuit 46 (through the selective application of pressure to the valves and pump stations of the cassette) makes it possible to use the same universal set 264 used to carry out the double red blood cell collection or the plasma collection procedure.

The procedure includes a pre-collection cycle, a collection cycle, and a post-collection cycle, and a storage preparation cycle.

During the pre-collection cycle, the set 264 is primed to vent air prior to venipuncture. During the collection cycle, whole blood drawn from the donor is processed to collect plasma and red blood cells, while returning a portion of the red blood cells to the donor. During the post-collection cycle, excess plasma and red blood cells are returned to the donor, and the set is flushed with saline. During the storage preparation cycle, a red blood cell storage solution added to the collected red blood cells.

(1) The Pre-Collection Cycle a. Anticoagulant Prime

In the pre-collection cycle for the red blood cell/plasma collection procedure, the cassette is programmed to carry out AC Prime 1 and AC Prime 2 Phases that are identical to the AC Prime 1 and AC Prime 2 Phases of the double red blood cell collection procedure.

b. Saline Prime

In the pre-collection cycle for the red blood cell/plasma collection procedure, the cassette is programmed to carry out Saline Prime 1, Saline Prime 2, Saline Prime 3, Vent Donor Line, and Venipuncture Phases that are identical to the Saline Prime 1, Saline Prime 2, Saline Prime 3, Vent Donor Line, and Venipuncture Phases of the double red blood cell collection procedure.

The programming of the circuit during the phases of the pre-collection cycle is summarized in the following table.

TABLE

Programming of Blood Processing Circuit During Pre-Collection Cycle
(Red Blood Cell/Plasma Collection Procedure)

| Phase | AC Prime 1 | AC Prime 2 | Saline Prime 1 | Saline Prime 2 | Saline Prime 3 | Vent Donor Line | Veni-puncture |
|---|---|---|---|---|---|---|---|
| V1 | ● | ● | ● | ● | ● | ● | ● |
| V2 | ● | ● | ● | ● | ● | ● | ● |
| V3 | ○ | ○ | ● | ● | ● | ○ | ● |
| V4 | ● | ● | ○ | ● | ● | ● | ● |
| V5 | ● | ● | ● | ● | ● | ● | ● |
| V6 | ● | ● | ● | ● | ○ | ● | ● |
| V7 | ● | ● | ● | ● | ○ | ● | ● |
| V8 | ● | ● | ● | ● | ● | ● | ● |
| V9 | ● | ● | ○/● Pump Out | ○/● Pump Out | ○/● Pump In (Stage 1) ○ (Stage 2) | ● | ● |
| V10 | ● | ● | ● | ● | ○ (Stage 1) ○/● Pump Out (Stage 2) | ● | ● |
| V11 | ○/● Pump Out | ○ | ● | ● | ● | ○/● Pump In | ● |
| V12 | ● | ● | ● | ● | ○ (Stage 1) ○/● Pump In (Stage 2) | ● | ● |
| V13 | ○/● Pump In | ○ | ● | ● | ● | ○/● Pump Out | ● |
| V14 | ● | ● | ○/● Pump In | ○/● Pump In | ○/● Pump Out (Stage 1) ○ (Stage 2) | ● | ● |
| V15 | ○ | ○/● Pump In Pump Out | ● | ● | ● | ○ | ● |
| V16 | ● | ● | ● | ● | ● | ● | ● |
| V17 | ● | ● | ● | ● | ● | ● | ● |
| V18 | ○ | ○ | ● | ● | ● | ○ | ● |
| V19 | ○ | ○ | ● | ● | ● | ○ | ● |
| V20 | ○ | ○/● Pump Out Pump In | ● | ● | ● | ○ | ● |
| V21 | ● | ● | ● | ● | ● | ● | ● |
| V22 | ● | ● | ○ | ○ | ○ | ● | ● |
| V23 | ● | ● | ○ | ○ | ○ | ● | ● |
| PP1 | ■ | ■ | □ | □ | □ (Stage 1) | ■ | ■ |
| PP2 | ■ | ■ | ■ | ■ | □ (Stage 2) | ■ | ■ |
| PP3 | □ | ■ | ■ | ■ | ■ | □ | ■ |
| PP4 | ■ | □ | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

2. The Collection Cycle a. Blood Prime

With venipuncture, tube 300 leading to the phlebotomy needle 268 is opened. The collection cycle of the red blood cell/plasma collection procedure programs the circuit to carry out Blood Prime 1 and Blood Prime 2 Phases that are identical to the Blood Prime 1 and Blood Prime 2 Phases of the Double Red Blood Cell Collection Procedure, already described.

b. Blood Separation While Drawing Whole Blood or Without Drawing Whole Blood In the blood collection cycle for the red blood cell/plasma collection procedure, the circuit is programmed to conduct a Blood Separation While Drawing Whole Blood Phase, in the same fashion that the Blood Separation While Drawing Whole Blood Phase is conducted for the double red blood cell collection procedure. This arrangement draws anticoagulated blood into the in-process container 312, while conveying the blood from the in-process container 312 into the processing chamber for separation. This arrangement also removes plasma from the processing chamber into the plasma container 304, while removing red blood cells from the processing chamber into the red blood cell container 308. This phase continues until the desired maximum volumes of plasma and red blood cells have been collected in the plasma and red blood cell collection containers 304 and 308 (as monitored by the weigh sensor).

As in the double red blood cell collection procedure and the plasma collection procedure, if the volume of whole blood in the in-process container 312 reaches a predetermined maximum threshold before the targeted volume of either plasma or red blood cells is collected, the circuit is programmed to enter a phase (Blood Separation Without Whole Blood Draw) to terminate operation of the donor interface pump station PP3 (while also closing valves V13, V11, V18, and V13) to terminate collection of whole blood in the in-process container 312, while still continuing blood separation. If the volume of whole blood reaches a predetermined minimum threshold in the in-process container 312 during blood separation, but before the targeted volume of either plasma or red blood cells is collected, the circuit is programmed to return to the Blood Separation With Whole Blood Draw, to thereby refill the in-process container 312. The circuit is programmed to toggle between the Blood Separation cycle with whole blood draw and without whole blood draw according to the high and low volume thresholds for the in-process container 312, until the requisite maximum volumes of plasma and red blood cells have been collected.

C. Return Red Blood Cells and Saline

If the targeted volume of plasma has not been collected, and red blood cells collected in the red blood cell container 308 exceed a predetermined maximum threshold, the next phase of the blood collection cycle (Return Red Blood Cells With Separation) programs the blood processing circuit 46 to operate the donor interface pump station PP3 (i.e., in through valve V11 and out through valve V13); the in-process pump PP1 (i.e., in through valve V9 and out through valve V14); and the plasma pump PP2 (i.e., in through valve V12 and out through valve V10). This arrangement continues to convey anticoagulated whole blood from the in-process container 312 into the processing chamber for separation, while removing plasma into the plasma container 304 and red blood cells into the red blood cell container 308. This arrangement also conveys all or a portion of the red blood cells collected in the red blood cell container 308 to the donor. This arrangement also mixes saline from the container 288 in line with the returned red blood cells. The in line mixing of saline with the red blood cells raises the saline temperature and improves donor comfort. The in line mixing of saline with the red blood cells also lowers the hematocrit of the red blood cells being returned to the donor, thereby allowing a larger gauge (i.e., smaller diameter) phlebotomy needle to be used, to further improve donor comfort.

This phase can continue until the red blood cell container 308 is empty, as monitored by the weigh sensor, thereby corresponding to the Return Red Blood Cells With Separation Phase of the plasma collection procedure. Preferably, however, the processor determines how much additional plasma needs to be collected to meet the plasma target volume. From this, the processor derives the incremental red blood cell volume associated with the incremental plasma volume. In this arrangement, the processor returns a partial volume of red blood cells to the donor, so that, upon collection of the next incremental red blood cell volume, the total volume of red blood cells in the container 308 will be at or slightly over the targeted red blood cell collection volume.

If the volume of whole blood in the in-process container 312 reaches a specified low threshold before return of the desired volume of red blood cells, the circuit is programmed to enter a phase (Return Red Blood Cells Without Separation), to terminate operation of the in-process pump station PP1 (while also closing valves V9, V10, V12, and V14) to terminate blood separation. This phase corresponds to the Return Red Blood Cells Without Separation Phase of the plasma collection procedure.

Upon returning the desired volume of red blood cells from the container 308, the circuit is programmed to enter a phase (Fill Donor Line), to operate the donor interface pump station PP3 (i.e., in through valve V11 and out through valve V13) to draw whole blood from the in process container 312 to fill the donor tube 266, thereby purge red blood cells (mixed with saline) in preparation for another draw whole blood cycle.

The circuit is then programmed to conduct another Blood Separation While Drawing Whole Blood Phase, to refill the in process container 312. If required, the circuit is capable of performing successive draw whole blood and return red blood cells cycles, until the weigh sensors indicate that volumes of red blood cells and plasma collected in the containers 304 and 308 are at or somewhat greater than the targeted values. The post-collection cycle then commences.

The programming of the circuit during the phases of the collection cycle is summarized in the following table.

TABLE

Programming of Blood Processing Circuit During The Collection Cycle
(Red Blood Cell/Plasma Collection Procedure)

| Phase | Blood Prime 1 | Blood Prime 2 | Blood Separation While Drawing Whole Blood (Without Drawing Whole Blood) | Return Red Blood Cells/Saline with Separation (Without Separation) | Fill Donor Line |
|---|---|---|---|---|---|
| V1 | ● | ● | ● | ● | ○ |
| V2 | ● | ● | ○ | ○ | ● |
| V3 | ○ | ● | ○ (●) | ● | ● |
| V4 | ● | ● | ● | ● | ● |
| V5 | ● | ● | ○ | ○ (●) | ● |
| V6 | ● | ● | ● | ● | ● |
| V7 | ● | ○ | ● | ○/● Alternates with V23 | ○ |
| V8 | ● | ● | ● | ● | ● |

TABLE-continued

Programming of Blood Processing Circuit During The Collection Cycle
(Red Blood Cell/Plasma Collection Procedure)

| Phase | Blood Prime 1 | Blood Prime 2 | Blood Separation While Drawing Whole Blood (Without Drawing Whole Blood) | Return Red Blood Cells/Saline with Separation (Without Separation) | Fill Donor Line |
|---|---|---|---|---|---|
| V9 | ● | ○/● Pump In | ○/● Pump In | ○/● Pump In (●) | ● |
| V10 | ● | ● | ○/● Pump Out | ○/● Pump Out (●) | ● |
| V11 | ○/● Pump Out | ○ | ○/● Pump Out (●) | ○/● Pump In | ○/● Pump In |
| V12 | ● | ● | ○/● Pump In | ○/● Pump In (●) | ● |
| V13 | ○/● Pump In | ○ | ○/● Pump In (●) | ○/● Pump Out | ○/● Pump Out |
| V14 | ● | ○/● Pump Out | ○/● Pump Out | ○/● Pump Out (●) | ● |
| V15 | ○/● Pump Out | ● | ○/● Pump Out (●) | ● | ● |
| V16 | ● | ● | ● | ● | ● |
| V17 | ● | ● | ● | ● | ● |
| V18 | ○ | ○ | ○ (●) | ○ | ○ |
| V19 | ○ | ● | ○ (●) | ● | ● |
| V20 | ○/● Pump Out | ● | ○/● Pump In (●) | ● | ● |
| V21 | ● | ● | ● | ● | ● |
| V22 | ● | ● | ● | ○ | ● |
| V23 | ● | ● | ● | ○/● Alternates with V7 | ● |
| PP1 | ■ | □ | □ | □ (■) | ■ |
| PP2 | ■ | ■ | □ | □ (■) | ■ |
| PP3 | □ | ■ | □ (■) | □ | □ |
| PP4 | □ | ■ | □ (■) | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

d. The Post-Collection Cycle

Once the targeted maximum volumes of plasma and red blood cells have been collected (as monitored by the weigh sensor), the circuit is programmed to carry out the phases of the post-collection cycle.

i. Return Excess Plasma

If the volume of plasma collected in the plasma collection container 304 is over the targeted volume, a phase of the post-collection cycle (Excess Plasma Return) is entered, during which the circuit is programmed to terminate the supply and removal of blood to and from the processing chamber, while operating the donor interface pump station PP3 (i.e., in through valve V11 and out through valve V13) to convey plasma in the plasma container 304 to the donor. The circuit is also programmed in this phase to mix saline from the container 288 in line with the returned plasma. This phase continues until the volume of plasma in the plasma collection container 304 is at the targeted value, as monitored by the weigh sensor.

ii. Return Excess Red Blood Cells

If the volume of red blood cells collected in the red blood cell collection container 308 is also over the targeted volume, a phase of the post-collection cycle (Excess RBC Return) is entered, during which the circuit is programmed to operate the donor interface pump station PP3 (i.e., in through valve V11 and out through valve V13) to convey red blood cells remaining in the red blood cell collection container 308 to the donor. The circuit is also programmed in this phase to mix saline from the container 288 in line with the returned red blood cells. This phase continues until the volume of red blood cells in the container 308 equals the targeted value, as monitored by the weigh sensor.

iii. Saline Purge

When the volumes of red blood cells and plasma collected in the containers 308 and 304 equal the targeted values, the next phase of the post-collection cycle (Saline Purge) is entered, during which the circuit is programmed to operate the donor interface pump station PP3 (i.e., in through valve V11 and out through valve V11) to convey saline from the container 288 through the separation device, to displace the blood contents of the separation device into the in-process container 312, in preparation for their return to the donor. This phase reduces the loss of donor blood. This phase continues until a predetermined volume of saline in pumped through the separation device, as monitored by the weigh sensor.

iv. Final Return to Donor

In the next phase of the post-collection cycle (Final Return), the circuit is programmed to operate the donor interface pump station PP3 (i.e., in through valve V11 and out through valve V13) to convey the blood contents of the in-process container 312 to the donor. Saline is intermittently mixed with the blood contents. This phase continues until the in-process container 312 is empty, as monitored by the weigh sensor.

In the next phase (Fluid Replacement), the circuit is programmed to operate the donor interface pump station PP3 (i.e., in through valve V11 and out through valve V13) to convey the saline to the donor. This phase continues until a prescribed replacement volume amount is infused, as monitored by the weigh sensor.

In the next phase (End Venipuncture), the circuit is programmed to close all valves and idle all pump stations, so that venipuncture can be terminated.

The programming of the circuit during the phases of the post-collection cycle is summarized in the following table.

e. The Storage Preparation Cycle i. RBC Preservative Prime

In the first phase of the storage preparation cycle (Prime Storage Solution), the circuit is programmed to operate the donor interface pump station PP3 to transfer a desired volume of red blood cell storage solution from the container 280 into the in-process container 312. The transfer of the desired volume is monitored by the weigh scale.

In the next phase (Transfer Storage Solution), the circuit is programmed to operate the donor interface pump station PP3 to transfer a desired volume of red blood cell storage solution from the in-process container 312 into the red blood cell collection container 308. The transfer of the desired volume is monitored by the weigh scale.

In the next and final phase (End Procedure), the circuit is programmed to close all valves and idle all pump stations, so that the plasma and red blood cell storage containers 304 and 308 can be separated and removed for storage. The remainder of the disposable set can now be removed and discarded.

TABLE

Programming of Blood Processing Circuit During The Post-Collection Cycle
(Red Blood Cell/Plasma Collection Procedure)

| Phase | Excess Plasma Return | Excess RBC Return | Saline Purge | Final Return | Fluid Replacement | End Venipuncture |
|---|---|---|---|---|---|---|
| V1 | ● | ● | ● | ○ | ● | ● |
| V2 | ● | ○ | ● | ● | ● | ● |
| V3 | ● | ● | ● | ● | ● | ● |
| V4 | ● | ● | ○ | ● | ● | ● |
| V5 | ○ | ● | ● | ● | ● | ● |
| V6 | ○/● Alternates with V23 | ● | ● | ● | ● | ● |
| V7 | ● | ○/● Alternates with V23 | ● | ○/● Alternates with V23 | ● | ● |
| V8 | ● | ● | ● | ● | ● | ● |
| V9 | ○ | ○ | ○ | ● | ● | ● |
| V10 | ● | ● | ● | ● | ● | ● |
| V11 | ○/● Pump In | ○/● Pump In | ○/● Pump In/Pump Out | ○/● Pump In | ○/● Pump In | ● |
| V12 | ● | ● | ● | ● | ● | ● |
| V13 | ○/● Pump Out | ○/● Pump Out | ● | ○/● Pump Out | ○/● Pump Out | ● |
| V14 | ● | ● | ○ | ● | ● | ● |
| V15 | ● | ● | ● | ● | ● | ● |
| V16 | ● | ● | ● | ● | ● | ● |
| V17 | ● | ● | ● | ● | ● | ● |
| V18 | ○ | ● | ● | ○ | ○ | ● |
| V19 | ● | ● | ● | ● | ● | ● |
| V20 | ● | ● | ● | ● | ● | ● |
| V21 | ● | ● | ● | ● | ● | ● |
| V22 | ○ | ○ | ○ | ○ | ○ | ● |
| V23 | ○/● Alternates with V6 | ○/● Alternates with V6 | ○ | ○/● Alternates with V7 | ○ | ● |
| PP1 | ■ | ■ | ■ | ■ | ■ | ■ |
| PP2 | ■ | ■ | ■ | ■ | ■ | ■ |
| PP3 | □ | □ | □ | □ | □ | ■ |
| PP4 | ■ | ■ | ■ | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

The programming of the circuit during the phases of the storage preparation cycle is summarized in the following table.

TABLE

Programming of Blood Processing Circuit During The Storage Preparation Cycle
(Red Blood Cell/Plasma Collection Procedure)

| Phase | Prime Storage Solution | Transfer Storage Solution | End Procedure |
|---|---|---|---|
| V1 | ● | ● | ● |
| V2 | ● | ○ | ● |
| V3 | ○ | ● | ● |
| V4 | ● | ○ | ● |
| V5 | ● | ● | ● |
| V6 | ● | ● | ● |
| V7 | ● | ● | ● |
| V8 | ● | ● | ● |
| V9 | ● | ● | ● |
| V10 | ● | ● | ● |
| V11 | ○/● Pump In/ Pump Out | ○/● Pump In/ Pump Out | ● |
| V12 | ● | ● | ● |
| V13 | ● | ● | ● |
| V14 | ● | ● | ● |
| V15 | ● | ● | ● |
| V16 | ○ | ○ | ● |
| V17 | ● | ● | ● |
| V18 | ● | ● | ● |
| V19 | ● | ● | ● |
| V20 | ● | ● | ● |
| V21 | ○ | ○ | ● |
| V22 | ● | ● | ● |
| V23 | ● | ● | ● |
| PP1 | ■ | ■ | ■ |
| PP2 | ■ | ■ | ■ |
| PP3 | □ | □ | ■ |
| PP4 | ■ | ■ | ■ |

Caption:
○ denotes an open valve;
● denotes a closed valve;
○/● denotes a valve opening and closing during a pumping sequence;
■ denotes an idle pump station (not in use); and
□ denotes a pump station in use.

V. Interface Control

A. Underspill and Overspill Detection

Figure 15A:
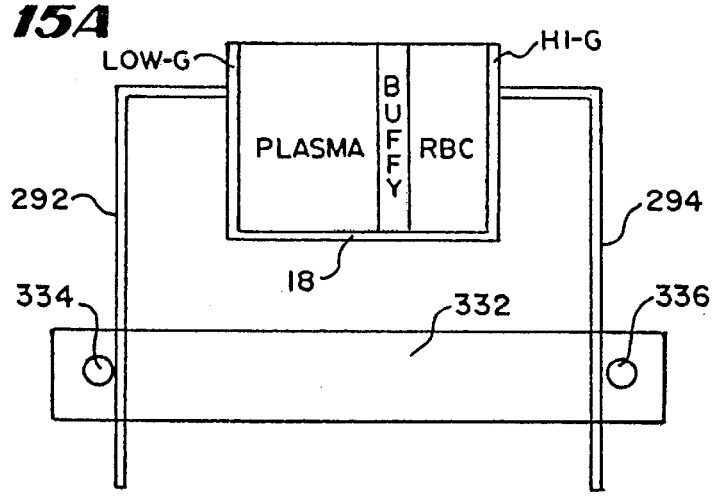
FIG. 15A, 15B, and 15C are schematic side view of the blood separation chamber that the device shown in FIG. 1 incorporates, showing the plasma and red blood cell collection tubes and the associated two in-line sensors, which detect a normal operating condition (FIG. 15A), an over spill condition (FIG. 15B), and an under spill condition (FIG. 15C)

In any of the above-described procedures, the 30 centrifugal forces present within the processing chamber 18 separate whole blood into a region of packed red blood cells and a region of plasma (see FIG. 15A). The centrifugal forces cause the region of packed red blood cells to congregate along the outside or high-G wall of the chamber, while the region of plasma is transported to the inside or low-G wall of the chamber.

An intermediate region forms an interface between the red blood cell region and the plasma region. Intermediate density cellular blood species like platelets and leukocytes populate the interface, arranged according to density, with the platelets closer to the plasma layer than the leukocytes. The interface is also called the "buffy coat," because of its cloudy color, compared to the straw color of the plasma region and the red color of the red blood cell region.

It is desirable to monitor the location of the buffy coat, either to keep the buffy coat materials out of the plasma or out of the red blood cells, depending on the procedure, or to collect the cellular contents of the buffy coat. The system includes a sensing station 332 comprising two optical sensors 334 and 336 for this purpose.

In the illustrated and preferred embodiment (see FIG. 13), the sensing station 332 is located a short distance outside the centrifuge station 20. This arrangement minimizes the fluid volume of components leaving the chamber before monitoring by the sensing station 332.

The first sensor 334 in the station 332 optically monitors the passage of blood components through the plasma collection tube 292. The second sensor 336 in the station 332 optically monitors the passage of blood components through the red blood cell collection tube 294.

The tubes 292 and 294 are made from plastic (e.g. polyvinylchloride) material that is transparent to the optical energy used for sensing, at least in the region where the tubes 292 and 294 are to be placed into association with the sensing station 332.

In the illustrated embodiment, the set 264 includes a fixture 338 (see FIGS. 16 to 18) to hold the tubes 292 and 294 in viewing alignment with its respective sensor 334 and 336. The fixture 338 gathers the tubes 292 and 294 in a compact, organized, side-by-side array, to be placed and removed as a group in association with the sensors 334 and 336, which are also arranged in a compact, side-by-side relationship within the station 332.

In the illustrated embodiment, the fixture 338 also holds the tube 290, which conveys whole blood into the centrifuge station 20, even though no associated sensor is provided. The fixture 338 serves to gather and hold all tubes 290, 292, and 294 that are coupled to the umbilicus 296 in a compact and easily handled bundle.

The fixture 338 can be an integral part of the umbilicus 296, formed, e.g., by over molding. Alternatively, the fixture 338 can be a separately fabricated part, which snap fits about the tubes 290, 292, and 294 for use.

In the illustrated embodiment (as FIG. 2 shows), the containers 304, 308, and 312 coupled to the cassette 28 are suspended during use above the centrifugation station 20. In this arrangement, the fixture 338 directs the tubes 290, 292, and 294 through an abrupt, ninety degree bend immediately beyond the end of the umbilicus 296 to the cassette 28. The bend imposed by the fixture 338 directs the tubes 290, 292, and 294 in tandem away from the area immediately beneath the containers 304, 308, and 312, thereby preventing clutter in this area. The presence of the fixture 338 to support and guide the tubes 290, 292, and 294 through the bend also reduces the risk of kinking or entanglement.

The first sensor 334 is capable of detecting the presence of optically targeted cellular species or components in the plasma collection tube 292. The components that are optically targeted for detection vary depending upon the procedure.

For a plasma collection procedure, the first sensor 334 detects the presence of platelets in the plasma collection tube 292, so that control measures can be initiated to move the interface between the plasma and platelet cell layer back into the processing chamber. This provides a plasma product that can be essentially platelet-free or at least in which the number of platelets is minimized.

For a red blood cell-only collection procedure, the first sensor 334 detects the interface between the buffy coat and the red blood cell layer, so that control measures can be initiated to move this interface back into the processing chamber. This maximizes the red blood cell yield.

For a buffy coat collection procedure (which will be described later), the first sensor 334 detects when the leading edge of the buffy coat (i.e., the plasma/platelet interface) begins to exit the processing chamber, as well as detects when the trailing edge of the buffy coat (i.e., the buffy coat/red blood cell interface) has completely exited the processing chamber.

Figure 15B:
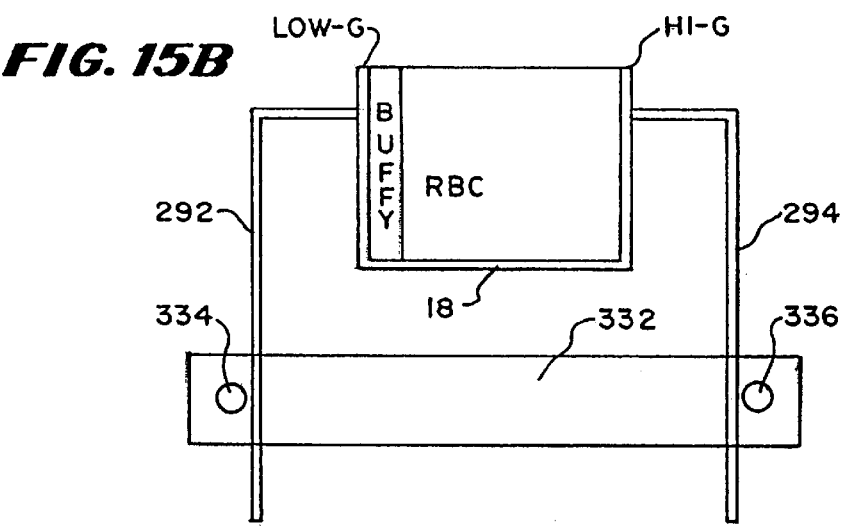

The presence of these cellular components in the plasma, as detected by the first sensor 334, indicates that the interface is close enough to the low-G wall of the processing chamber to allow all or some of these components to be swept into the plasma collection line (see FIG. 15B) This condition will also be called an "over spill."

Figure 15C:
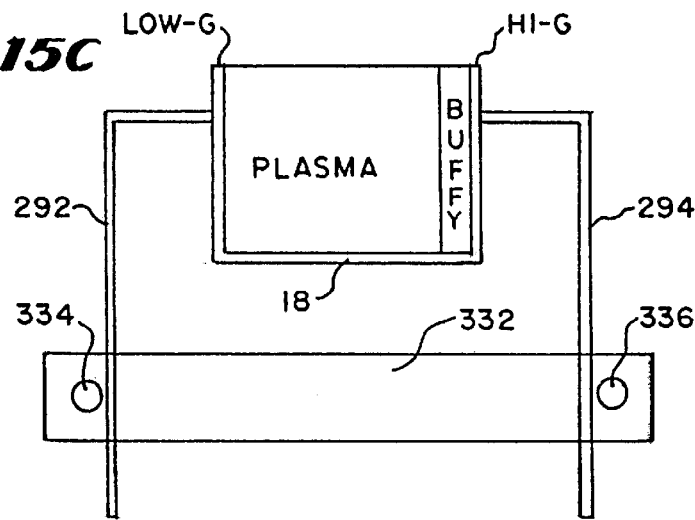

The second sensor 336 is capable of detecting the hematocrit of the red blood cells in the red blood cell collection tube 294. The decrease of red blood hematocrit below a set minimum level during processing that the interface is close enough to the high-G wall of the processing chamber to allow plasma to enter the red blood cell collection tube 294 (see FIG. 15C). This condition will also be called an "under spill."

B. The Sensing Circuit

Figure 19:
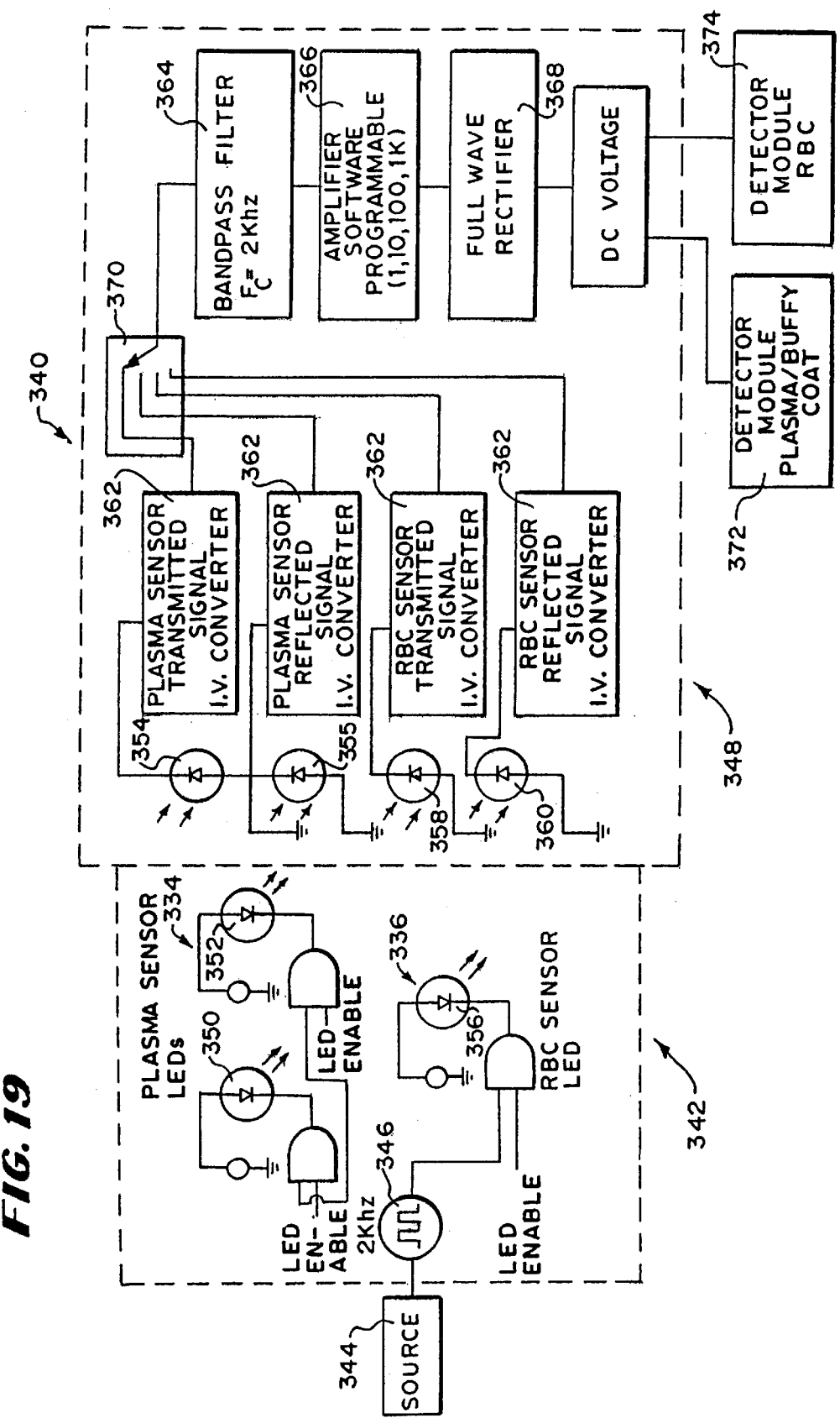
FIG. 19 is a schematic view of the sensing station, of which the first and second sensors shown in FIGS. 15A, 15B, and 15C form a part.

The sensing station 332 includes a sensing circuit 340 (see FIG. 19), of which the first sensor 334 and second sensor 336 form a part.

The first sensor 334 includes one green light emitting diode (LED) 350, one red LED 352, and two photodiodes 354 and 355. The photodiode 354 measures transmitted light, and the photodiode 355 measures reflected light.

The second sensor 336 includes one red LED 356 and two photodiodes 358 and 360. The photodiode 358 measures transmitted light, and the photodiode 360 measures reflected light.

The sensing circuit 340 further includes an LED driver component 342. The driver component 342 includes a constant current source 344, coupled to the LED's 350, 352, and 356 of the sensors 334 and 336. The constant current source 344 supplies a constant current to each LED 350, 352, and 356, independent of temperature and the power supply voltage levels. The constant current source 344 thereby provides a constant output intensity for each LED 350, 352, and 356.

The LED drive component 342 includes a modulator 346. The modulator 346 modulates the constant current at a prescribed frequency. The modulation 346 removes the effects of ambient light and electromagnetic interference (EMI) from the optically sensed reading, as will be described in greater detail later.

The sensing circuit 340 also includes a receiver circuit 348 coupled to the photodiodes 354, 355, 358, and 360. The receiver circuit 348 includes, for each photodiode 354, 355, 358, and 360, a dedicated current-to-voltage (I-V) converter 362. The remainder of the receiver circuit 348 includes a bandpass filter 364, a programmable amplifier 366, and a full wave rectifier 368. These components 364, 366, and 368 are shared, e.g., using a multiplexer.

Ambient light typically contains frequency components less than 1000 Hz, and EMI typically contains frequency components above 2 Khz. With this in mind, the modulator 346 modulates the current at a frequency below the EMI frequency components, e.g., at about 2 Khz. The bandpass filter 364 has a center frequency of about the same value, i.e., about 2 Khz. The sensor circuit 340 eliminates frequency components above and below the ambient light source and EMI components from the sensed measurement. In this way, the sensing circuit 340 is not sensitive to ambient lighting conditions and EMI.

More particularly, transmitted or reflected light from the tube 292 or 294 containing the fluid to be measured is incident on photodiodes 354 and 355 (for the tube 292) or photodiodes 358 and 360 (for tube 294). Each photodiode produces a photocurrent proportional to the received light intensity. This current is converted to a voltage. The voltage is fed, via the multiplexer 370, to the bandpass filter 364. The bandpass filter 364 has a center frequency at the carrier frequency of the modulated source light (i.e., 2 Khz in the illustrated embodiment).

The sinusoidal output of the bandpass filter 364 is sent to the variable gain amplifier 366. The gain of the amplifier is preprogrammed in preestablished steps, e.g., X1, X10, X100, and X1000. This provides the amplifier with the capability to respond to a large dynamic range.

The sinusoidal output of the amplifier 366 is sent to the full wave rectifier 368, which transforms the sinusoidal output to a DC output voltage proportional to the transmitted light energy.

The controller 16 generates timing pulses for the sensor circuit 340. The timing pulses comprise, for each LED, (i) a modulation square wave at the desired modulation frequency (i.e., 2 Khz in the illustrated embodiment), (ii) an enable signal, (iii) two sensor select bits (which select the sensor output to feed to the bandpass filter 364), and (iv) two bits for the receiver circuit gain selection (for the amplifier 366).

The controller 16 conditions the driver circuit 342 to operate each LED in an ON state and an OFF state.

In the ON state, the LED enable is set HIGH, and the LED is illuminated for a set time interval, e.g., 100 ms. During the first 83.3 ms of the ON state, the finite rise time for the incident photodiode and receiver circuit 348 are allowed to stabilize. During the final 16.7 ms of the ON state, the output of the circuit 340 is sampled at twice the modulation rate (i.e., 4 Khz in the illustrated embodiment). The sampling interval is selected to comprises one complete cycle of 60 Hz, allowing the main frequency to be filtered from the measurement. The 4 Khz sampling frequency allows the 2 Khz ripple to be captured for later removal from the measurement.

During the OFF state, the LED is left dark for 100 ms. The LED baseline due to ambient light and electromagnetic interference is recorded during the final 16.7 ms.

1. The First Sensor: Platelet/RBC Differentiation

In general, cell free ("free") plasma has a straw color. As the concentration of platelets in the plasma increases, the clarity of the plasma decreases. The plasma looks "cloudy." As the concentration of red blood cells in the plasma increases, the plasma color turns from straw to red.

The sensor circuit 340 includes a detection/differentiation module 372, which analyses sensed attenuations of light at two different wavelengths from the first sensor 334 (using the transmitted light sensing photodiode 354). The different wavelengths are selected to possess generally the same optical attenuation for platelets, but significantly different optical attentuations for red blood cells.

In the illustrated embodiment, the first sensor 334 includes an emitter 350 of light at a first wavelength ($\lambda_1$), which, in the illustrated embodiment, is green light (570 nm and 571 nm). The first sensor 334 also includes an emitter 352 of light at a second wavelength ($\lambda_2$), which, in the illustrated embodiment, is red light (645 nm to 660 nm).

The optical attenuation for platelets at the first wavelength ($\epsilon_{platelets}^{\lambda_1}$) and the optical attenuation for platelets at the second wavelength ($\epsilon_{platelets}^{\lambda_2}$) are generally the same. Thus, changes in attenuation over time, as affected by increases or decreases in platelet concentration, will be similar.

However, the optical attenuation for hemoglobin at the first wavelength ($\epsilon_{Hb}^{\lambda_1}$) is about ten times greater than the optical attenuation for hemoglobin at the second wavelength ($\epsilon_{Hb}^{\lambda_2}$). Thus, changes in attenuation over time, as affected by the presence of red blood cells, will not be similar.

The tube 294, through which plasma to be sensed, is transparent to light at the first and second wavelengths. The tube 294 conveys the plasma flow past the first and second emitters 350 and 352.

The light detector 354 receives light emitted by the first and second emitters 350 and 352 through the tube 294. The detector 354 generates signals proportional to intensities of received light. The intensities vary with optical attenuation caused by the presence of platelets and/or red blood cells.

The module 372 is coupled to the light detector 354 to analyze the signals to derive intensities of the received light at the first and second wavelengths. The module 372 compares changes of the intensities of the first and second wavelengths over time. When the intensities of the first and second wavelengths change over time in substantially the same manner, the module 372 generates an output representing presence of platelets in the plasma flow. When the intensities of the first and second wavelengths change over time in a substantially different manner, the module 372 generates an output representing presence of red blood cells in the plasma flow. The outputs therefore differentiate between changes in intensity attributable to changes in platelet concentration in the plasma flow and changes in intensity attributable to changes in red blood cell concentration in the plasma flow.

There are various ways to implement the module 372. In a preferred embodiment, the detection/differentiation module 372 considers that the attenuation of a beam of monochromatic light of wavelength $\lambda$ by a plasma solution can be described by the modified Lambert-Beer law, as follows:

$$I = I_o e^{-[(\varepsilon^\lambda_{Hb} c_{Hb} H + \varepsilon^\lambda_{platelets} c_{platelets})d + G^\lambda_{platelets} + G^\lambda_{RBC}]} \quad (1)$$

where:

I is transmitted light intensity.

$I_0$ is incident light intensity.

$\varepsilon_{Hb}^\lambda$ is the optical attenuation of hemoglobin (Hb) (gm/dl) at the applied wavelength.

$\varepsilon_{platelets}^\lambda$ is the optical attenuation of platelets at the applied wavelength.

$C_{Hb}$ is the concentration of hemoglobin in a red blood cell, taken to be 34 gm/dl.

$C_{platelets}$ is the concentration of platelets in the sample. d is thickness of the plasma stream through the tube 294.

$G^\lambda$ is the path length factor at the applied wavelength, which accounts for additional photon path length in the plasma sample due to light scattering.

H is whole blood hematocrit, which is percentage of red blood cells in the sample.

$G_{RBC}^\lambda$ and $G_{platelets}^\lambda$ are a function of the concentration and scattering coefficients of, respectively, red blood cells and platelets at the applied wavelengths, as well as the measurement geometry.

For wavelengths in the visible and near infrared spectrum, $\varepsilon_{platelets}^\lambda \approx 26$, therefore:

$$\text{Ln}\left(\frac{I^\lambda}{I_o^\lambda}\right) = \text{Ln}(T^\lambda) \approx -[(\varepsilon^\lambda_{Hb} C_{Hb} H)d + G^\lambda_{platelets} + G^\lambda_{RBC}] \quad (2)$$

In an over spill condition (shown in FIG. 15B), the first cellular component to be detected by the first sensor 334 in the plasma collection line 294 will be platelets. Therefore, for the detection of platelets, $\text{Ln}(T^\lambda) \approx G_{platelets}^\lambda$.

To detect the buffy coat interface between the platelet layer and the red blood cell layer, the two wavelengths ($\lambda_1$ and $\lambda_2$) are chosen based upon the criteria that (i) $\lambda_1$ and $\lambda_2$ have approximately the same path length factor ($G^\lambda$), and (ii) one wavelength $\lambda_1$ or $\lambda_2$ has a much greater optical attenuation for hemoglobin than the other wavelength.

Assuming the wavelengths $\lambda_1$ and $\lambda_2$ have the same $G^\lambda$, Equation (2) reduces to:

$$\text{Ln}(T^{\lambda_1}) - \text{Ln}(T^{\lambda_2}) \approx H d c_{Hb} (\varepsilon_{Hb}^{\lambda_2} - \varepsilon_{Hb}^{\lambda_1}) \quad (3)$$

In the preferred embodiment, $\lambda_1$ 660 nm (green) and $\lambda_2$=571 nm (red). The path length factor ($G^\lambda$) for 571 nm light is greater than for 660 nm light. Therefore the path length factors have to be modified by coefficients $\alpha$ and $\beta$, as follows:

$$G_{RBC}^{\lambda_1} = \alpha G_{RBC}^{\lambda_2}$$

$$G_{platelets}^{\lambda_1} = \beta G_{platelets}^{\lambda_2}$$

Therefore, Equation (3) can be reexpressed as follows:

$$\text{Ln}(T^{\lambda_1}) - \text{Ln}(T^{\lambda_2}) \approx H d c_{Hb}(\varepsilon_{Hb}^{\lambda_2} - \varepsilon_{Hb}^{\lambda_1}) + (\alpha - 1) G_{RBC}^{\lambda_1} + (\beta - 1) G_{platelets}^{\lambda_2} \quad (4)$$

In the absence of red blood cells, Equation (3) causes a false red blood cell detect with increasing platelet concentrations, as Equation (5) demonstrates:

$$\text{Ln}(T^{\lambda_1}) - \text{Ln}(T^{\lambda_2}) = (\beta - 1) G_{platelets}^{\lambda_1} \quad (5)$$

For the detection of platelets and the interface between the platelet/red blood cell layer, Equation (4) provides a better resolution. The module 372 therefore applies Equation (4). The coefficient ($\beta-1$) can be determined by empirically measuring $G^{\lambda_1}_{platelets}{}^{\lambda_1}$ and $G^{\lambda_2}_{platelets}{}^{\lambda_2}$ in the desired measurement geometry for different known concentrations of platelets in prepared platelet-spiked plasma.

The detection/differentiation module 372 also differentiates between intensity changes due to the presence of red blood cells in the plasma or the presence of free hemoglobin in the plasma due to hemolysis. Both circumstances will cause a decrease in the output of the transmitted light sensing photodiode 354. However, the output of the reflected light sensing photodiode 355 increases in the presence of red blood cells and decreases in the presence of free hemoglobin. The detection/differentiation module 372 thus senses the undesired occurrence of hemolysis during blood processing, so that the operator can be alerted and corrective action can be taken.

2. The Second Sensor: Packed Red Blood Cell Measurement

In an under spill condition (shown in FIG. 15C), the hematocrit of red blood cells exiting the processing chamber 18 will dramatically decrease, e.g., from a targeted hematocrit of about 80 to a hematocrit of about 50, as plasma (and the buffy coat) mixes with the red blood cells. An under spill condition is desirable during a plasma collection procedure, as it allows the return of the buffy coat to the donor with the red blood cells. An under spill condition is not desired during a red blood cell-only collection procedure, as it jeopardizes the yield and quality of red blood cells that are collected for storage.

In either situation, the ability to sense when an under spill condition exists is desireable.

Photon wavelengths in the near infrared spectrum (NIR) (approximately 540 nm to 1000 nm) are suitable for sensing red blood cells, as their intensity can be measured after transmission through many millimeters of blood.

The sensor circuit 340 includes a red blood cell detection module 374. The detection module 374 analyses sensed optical transmissions of the second sensor 336 to discern the hematocrit and changes in the hematocrit of red blood cells exiting the processing chamber 18.

The detection module 374 considers that the attenuation of a beam of monochromatic light of wavelength λ by blood may be described by the modified Lambert-Beer law, as follows:

$$I = I_o e^{-[(\varepsilon_{Hb}^\lambda C_{Hb} H)d + G_{RBC}^\lambda]} \quad (6)$$

where:
- I is transmitted light intensity.
- $I_0$ is incident light intensity.
- $\varepsilon_{Hb}^\lambda$ is the extinction coefficient of hemoglobin (Hb) (gm/dl) at the applied wavelength.
- $C_{Hb}$ is the concentration of hemoglobin in a red blood cell, taken to be 34 gm/dl.
- d is the distance between the light source and light detector.
- $G^\lambda$ is the path length factor at the applied wavelength, which accounts for additional photon path length in the media due to light scattering.
- H is whole blood hematocrit, which is percentage of red blood cells in the sample.
- $G_{RBC}^\lambda$ is a function of the hematocrit and scattering coefficients of red blood cells at the applied wavelengths, as well as the measurement geometry.

Given Equation (6), the optical density O.D. of the sample can be expressed as follows:

$$\text{Ln}\left(\frac{I^\lambda}{I_o^\lambda}\right) = O.D. \approx -[(\varepsilon_{Hb}^\lambda C_{Hb} H)d + G_{RBC}^\lambda] \quad (7)$$

The optical density of the sample can further be expressed as follows:

$$O.D. = O.D._{Absorption} + O.D._{Scattering} \quad (8)$$

where:

$O.D._{Absorption}$ is the optical density due to absorption by red blood cells, expressed as follows:

$$O.D._{Absorption} = -(\varepsilon_{Hb}^\lambda C_{Hb} H)d \quad (9)$$

$O.D._{Scattering}$ is the optical density due to scattering of red blood cells, expressed as follows:

$$O.D._{Scattering} = G_{RBC}^\lambda \quad (10)$$

From Equation (9), $O.D._{Absorption}$ increases linearly with hematocrit (H). For transmittance measurements in the red and NIR spectrum, $G_{RBC}^\lambda$ is generally parabolic, reaching a maximum at a hematocrit of between 50 and 75 (depending on illumination wavelength and measurement geometry) and is zero at hematocrits of 0 and 100 (see, e.g., Steinke et al., "Diffusion Model of the Optical Absorbance of Whole Blood," *J. Opt. Soc. Am.*, Vol 5, No. 6, June 1988). Therefore, for light transmission measurements, the measured optical density is a nonlinear function of hematocrit.

Nevertheless, it has been discovered that $G_{RBC}^\lambda$ for reflected light measured at a predetermined radial distance from the incident light source is observed to remain linear for the hematocrit range of at least 10 to 90. Thus, with the second sensor 336 so configured, the detection module can treat the optical density of the sample for the reflected light to be a linear function of hematocrit. The same relationship exists for the first sensor 334 with respect to the detection of red blood cells in plasma.

This arrangement relies upon maintaining straightforward measurement geometries. No mirrors or focusing lenses are required. The LED or photodiode need not be positioned at an exact angle with respect to the blood flow tube. No special optical cuvettes are required. The second sensor 336 can interface directly with the transparent plastic tubing 294. Similarly, the first sensor 334 can interface directly with the transparent tubing 292.

In the illustrated embodiment, the wavelength 805 nm is selected, as it is an isobestic wavelength for red blood cells, meaning that light absorption by the red blood cells at this wavelength is independent of oxygen saturation. Still, other wavelengths can be selected within the NIR spectrum.

In the illustrated embodiment, for a wavelength of 805 nm, the preferred set distance is 7.5 mm from the light source. The fixture 338, above described (see FIG. 18), facilitates the placement of the tube 294 in the desired relation to the light source and the reflected light detector of the second sensor 336. The fixture 338 also facilitates the placement of the tube 292 in the desired relation to the light source and the reflected light detector of the first sensor 334.

Measurements at a distance greater than 7.5 mm can be made and will show a greater sensitivity to changes in the red blood cell hematocrit. However a lower signal to noise ratio will be encountered at these greater distances. Likewise, measurements at a distance closer to the light source will show a greater signal to noise ratio, but will be less sensitive to changes in the red blood cell hematocrit. The optimal distance for a given wavelength in which a linear relationship between hematocrit and sensed intensity exists for a given hematocrit range can be empirically determined.

Figure 20:
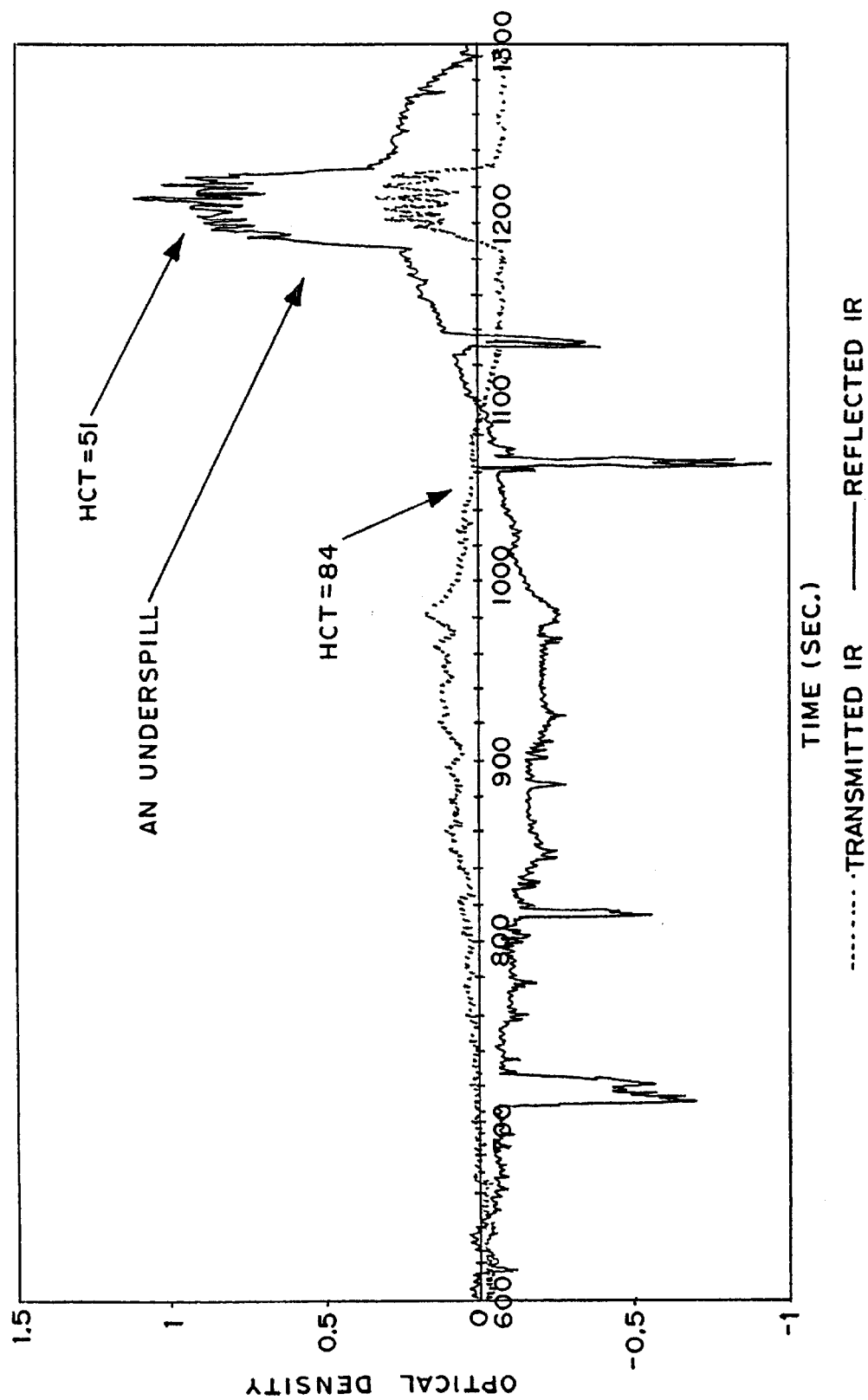
FIG. 20 is a graph of optical densities as sensed by the first and second sensors plotted over time, showing an under spill condition.

The second sensor 336 detects absolute differences in the mean transmitted light intensity of the signal transmitted through the red blood cells in the red blood cell collection line. The detection module analyzes these measured absolute differences in intensities, along with increases in the standard deviation of the measured intensities, to reliably signal an under spill condition, as FIG. 20 shows.

At a given absolute hematocrit, $G_{RBC}^\lambda$ varies slightly from donor to donor, due to variations in the mean red blood cell volume and/or the refractive index difference between the plasma and red blood cells. Still, by measuring the reflected light from a sample of a given donor's blood having a known hematocrit, $G_{RBC}^\lambda$ may be calibrated to yield, for that donor, an absolute measurement of the hematocrit of red blood cells exiting the processing chamber.

C. Pre-Processing Calibration of the Sensors

The first and second sensors 334 and 336 are calibrated during the saline and blood prime phases of a given blood collection procedure, the details of which have already described.

During the saline prime stage, saline is conveyed into the blood processing chamber 18 and out through the plasma collection line 292. During this time, the blood processing chamber 18 is rotated in cycles between 0 RPM and 200 RPM, until air is purged from the chamber 18. The speed of rotation of the processing chamber 18 is then increased to full operational speed.

The blood prime stage follows, during which whole blood is introduced into the processing chamber 18 at the desired whole blood flow rate ($Q_{WB}$). The flow rate of plasma from the processing chamber through the plasma collection line 292 is set at a fraction (e.g., 80%) of the desired plasma flow rate ($Q_P$) from the processing chamber 18, to purge saline from the chamber 18. The purge of saline continues under these conditions until the first sensor 334 optically senses the presence of saline in the plasma collection line 292.

1. For Plasma Collection Procedures (Induced Under Spill)

If the procedure to be performed collects plasma for storage (e.g., the Plasma Collection Procedure or the Red Blood Cell/Plasma Collection Procedure), an under spill condition is induced during calibration. The under spill condition is created by decreasing or stopping the flow of plasma through the plasma collection line 292. This forces the buffy coat away from the low-G side of the chamber 18 (as FIG. 15C) to assure that a flow of "clean" plasma exists in the plasma collection line 292, free or essentially free of platelets and leukocytes. The induced under spill allows the first sensor 334 to be calibrated and normalized with respect to the physiologic color of the donor's plasma, taking into account the donor's background lipid level, but without the presence of platelets or leukocytes. The first sensor 334 thereby possesses maximum sensitivity to changes brought about by the presence of platelets or leukocytes in the buffy coat, should an over spill subsequently occur during processing.

Forcing an under spill condition also positions the interface close to the high-G wall at the outset of blood processing. This creates an initial offset condition on the high-G side of the chamber, to prolong the ultimate development of an over spill condition as blood processing proceeds.

2. Red Blood Cell Collection Procedures

If a procedure is to be performed in which no plasma is to be collected (e.g., the Double Unit Red Blood Cell Collection Procedure), an under spill condition is not induced during the blood purge phase. This is because, in a red blood cell only collection procedure, the first sensor 334 need only detect, during an over spill, the presence of red blood cells in the plasma. The first sensor 334 does not need to be further sensitized to detect platelets. Furthermore, in a red blood cell only collection procedure, it may be desirable to keep the interface as near the low-G wall as possible. The desired condition allows the buffy coat to be returned to the donor with the plasma and maximizes the hematocrit of the red blood cells collected.

D. Blood Cell Collection

1. Plasma Collection Procedures

In procedures where plasma is collected (e.g., the Plasma Collection Procedure or the Red Blood Cell/Plasma Collection Procedure), $Q_P$ is set at $Q_{P(Ideal)}$, which is an empirically determined plasma flow rate that allows the system to maintain a steady state collection condition, with no underspills and no overspills.

$Q_{P(Ideal)}$ (in grams/ml) is a function of the anticogulated whole blood inlet flow rate $Q_{WB}$, the anticoagulant whole blood inlet hematocrit $HCT_{WB}$, and the red blood cell exit hematocrit $HCT_{RBC}$ (as estimated or measured), expressed as follows:

$$Q_{P(Ideal)} = (\rho_{Plasma} Q_{WB} * \frac{(1 - HCT_{WB}) - \left[\frac{\rho_{WB}}{\rho_{RBC}}(1 - HCT_{RBC})\right]}{\left(1 - \frac{\rho_{Plasma}}{\rho_{RBC}}\right)(1 - HCT_{RBC})}$$

where:

$\rho_{Plasma}$ is the density of plasma (in g/ml)=1.03

$\rho_{WB}$ is the density of whole blood (in g/ml)=1.05

$\rho_{RBC}$ is the density of red blood cells=1.08

$Q_{WB}$ is set to the desired whole blood inlet flow rate for plasma collection, which, for a plasma only collection procedure, is generally about 70 ml/min. For a red blood cell/plasma collection procedure, $Q_{WB}$ is set at about 50 ml/min, thereby providing packed red blood cells with a higher hematocrit than in a traditional plasma collection procedure.

The system controller 16 maintains the pump settings until the desired plasma collection volume is achieved, unless an under spill condition or an over spill condition is detected.

If set $Q_P$ is too high for the actual blood separation conditions, or, if due to the physiology of the donor, the buffy coat volume is larger (i.e., "thicker") than expected, the first sensor 334 will detect the presence of platelets or leukocytes, or both in the plasma, indicating an over spill condition.

In response to an over spill condition caused by a high $Q_P$, the system controller 16 terminates operation of the plasma collection pump PP2, while keeping set $Q_{WB}$, unchanged. In response to an over spill condition caused by a high volume buffy coat, the system controller 16 terminates operation of the plasma collection pump PP2, until an under spill condition is detected by the red blood cell sensor 336. This serves to expel the buffy coat layer from the separation chamber through the red blood cell tube 294.

To carry out the over spill response, the blood processing circuit 46 is programmed to operate the in-process pump PP1 (i.e., drawing in through the valve V9 and expelling out of the valve V14), to draw whole blood from the in-process container 312 into the processing chamber 18 at the set $Q_{WB}$. Red blood cells exit the chamber 18 through the tube 294 for collection in the collection container 308. The flow rate of red blood cells directly depends upon the magnitude of $Q_{WB}$.

During this time, the blood processing circuit 46 is also programmed to cease operation of the plasma pump PP2 for a preestablished time period (e.g., 20 seconds). This forces the interface back toward the middle of the separation chamber. After the preestablished time period, the operation of the plasma pump PP2 is resumed, but at a low flow rate (e.g., 10 ml/min) for a short time period (e.g., 10 seconds). If the spill has been corrected, clean plasma will be detected by the first sensor 334, and normal operation of the blood processing circuit 46 is resumed. If clean plasma is not sensed, indicating that the over spill has not been corrected, the blood processing circuit 46 repeats the above-described sequence.

The programming of the circuit to relieve an over spill condition is summarized in the following table.

TABLE

Programming of Blood Processing Circuit To Relive an Over Spill Condition
(Plasma Collection Procedures)

| | |
|---|---|
| V1 | ● |
| V2 | ○ |
| V3 | ● |
| V4 | ● |
| V5 | ○ |
| V6 | ● |
| V7 | ● |
| V8 | ● |
| V9 | ●/○ Pump In |
| V10 | ● |
| V11 | ● |
| V12 | ● |

TABLE-continued

Programming of Blood Processing Circuit To Relive an Over Spill Condition
(Plasma Collection Procedures)

| | |
|---|---|
| V13 | ● |
| V14 | ●/○ Pump Out |
| V15 | ● |
| V16 | ● |
| V17 | ● |
| V18 | ● |
| V19 | ● |
| V20 | ● |
| V21 | ● |
| V22 | ● |
| V23 | ● |
| PP1 | □ |
| PP2 | ■ |
| PP3 | ■ |
| PP4 | ■ |

Caption:
○ denotes an open valve;
● denotes a closed valve;
○/● denotes a valve opening and closing during a pumping sequence;
■ denotes an idle pump station (not in use); and
□ denotes a pump station in use.

Upon correction of an over spill condition, the controller 16 returns the blood processing circuit 46 to resume normal blood processing, but applies a percent reduction factor (%RF) to the $Q_P$ set at the time the over spill condition was initially sensed. The reduction factor (%RF) is a function of the time between over spills, i.e., %RF increases as the frequency of over spills increases, and vice versa.

If set $Q_P$ is too low, the second sensor 336 will detect a decrease in the red blood cell hematocrit below a set level, which indicates an under spill condition.

In response to an under spill condition, the system controller 16 resets $Q_P$ close to the set QWB. As processing continues, the interface will, in time, move back toward the low-G wall. The controller 16 maintains these settings until the second sensor 336 detects a red blood cell hematocrit above the desired set level. At this time, the controller 16 applies a percent enlargement factor (%EF) to the $Q_P$ set at the time the under spill condition was initially sensed. The enlargement factor (%EF) is a function of the time between under spills, i.e., %EF increases as the frequency of under spills increases.

Should the controller 16 be unable to correct a given under or over spill condition after multiple attempts (e.g. three attempts), an alarm is commanded.

2. Red Blood Cell Only Collection Procedures

In procedures where only red blood cells and no plasma is collected (e.g., the Double Unit Red Blood Cell Collection Procedure), $Q_P$ is set to no greater than $Q_{P(Ideal)}$ and $Q_{WB}$ is set to the desired whole blood inlet flow rate into the processing chamber 18 for the procedure, which is generally about 50 ml/min for a double unit red blood cell collection procedure.

It may be desired during a double unit red blood cell collection procedure that over spills occur frequently. This maximizes the hematocrit of the red blood cells for collection and returns the buffy coat to the donor with the plasma. $Q_P$ is increased over time if over spills occur at less than a set frequency. Likewise, $Q_P$ is decreased over time if over spills occur above the set frequency. However, to avoid an undesirably high hematocrit, it may be just as desirable to operate at $Q_{P(Ideal)}$.

The system controller 16 controls the pump settings in this way until the desired red blood cell collection volume is achieved, taking care of under spills or over spills as they occur.

The first sensor 334 detects an over spill by the presence of red blood cells in the plasma. In response to an over spill condition, the system controller 16 terminates operation of the plasma collection pump to draw plasma from the processing chamber, while keeping the set $Q_{WB}$ unchanged.

To implement the over spill response, the blood processing circuit 46 is programmed (through the selective application of pressure to the valves and pump stations) to operate the plasma pump PP2 and in-process pump PP1 in the manner set forth in the immediately preceding Table. The red blood cells detected in the tube 292 are thereby returned to the processing chamber 18, and are thereby prevented from entering the plasma collection container 304.

The interface will, in time, move back toward the high-G wall. The controller 16 maintains these settings until the second sensor 336 detects a decrease in the red blood cell hematocrit below a set level, which indicates an under spill condition.

In response to an under spill condition, the system controller 16 increases $Q_P$ until the second sensor 336 detects a red blood cell hematocrit above the desired set level. At this time, the controller 16 resets $Q_P$ to the value at the time the most recent overspill condition was sensed.

3. Buffy Coat Collection

If desired, an over spill condition can be periodically induced during a given plasma collection procedure to collect the buffy coat in a buffy coat collection container 376 (see FIG. 10). As FIG. 10 shows, in the illustrated embodiment, the buffy coat collection container 376 is coupled by tubing 378 to the buffy port P4 of the cassette 28. The buffy coat collection container 376 is suspended on a weigh scale 246, which provides output reflecting weight changes over time, from which the controller 16 derives the volume of buffy coat collected.

In this arrangement, when the induced over spill condition is detected, the blood processing circuit 46 is programmed (through the selective application of pressure to the valves and pump stations) to operate the plasma pump PP2 (i.e., drawing in through valve V12 and expelling out through valve V10), to draw plasma from the processing chamber 18 through the tube 378, while valves V4 and V6 are closed and valve V8 is opened. The buffy coat in the tube 378 is conveyed into the buffy coat collection container 376. The blood processing circuit 46 is also programmed during this time to operate the in-process pump PP1 (i.e., drawing in through the valve V9 and expelling out of the valve V14), to draw whole blood from the in-process container 312 into the processing chamber 18 at the set $Q_{WB}$. Red blood cells exit the chamber 18 through the tube 294 for collection in the collection container 308.

The programming of the circuit to relieve an over spill condition by collecting the buffy coat in the buffy coat collection container 376 is summarized in the following table.

TABLE

Programming of Blood Processing Circuit To Relive an Over Spill Condition by Collecting the Buffy Coat
(Plasma Collection Procedures)

| | |
|---|---|
| V1 | ● |
| V2 | ● |
| V3 | ● |
| V4 | ○ |
| V5 | ● |
| V6 | ● |
| V7 | ● |

TABLE-continued

Programming of Blood Processing Circuit To Relive an Over
Spill Condition by Collecting the Buffy Coat
(Plasma Collection Procedures)

| | |
|---|---|
| V8 | ● |
| V9 | ●/○ Pump In |
| V10 | ●/○ Pump Out |
| V11 | ● |
| V12 | ●/○ Pump In |
| V13 | ● |
| V14 | ●/○ Pump Out |
| V15 | ● |
| V16 | ● |
| V17 | ● |
| V18 | ● |
| V19 | ● |
| V20 | ● |
| V21 | ● |
| V22 | ● |
| V23 | ● |
| PP1 | □ |
| PP2 | □ |
| PP3 | ■ |
| PP4 | ■ |

Caption:
○ denotes an open valve;
● denotes a closed valve;
○/● denotes a valve opening and closing during a pumping sequence;
■ denotes an idle pump station (not in use); and
□ denotes a pump station in use.

After a prescribed volume of buffy coat is conveyed into the buffy coat collection container 376 (as monitored by the weigh scale 246), normal blood processing conditions are resumed. Over spill conditions causing the movement of the buffy coat into the tube 378 can be induced at prescribed intervals during the process period, until a desired buffy coat volume is collected in the buffy coat collection container.

VI. Another Programmable Blood Processing Circuit

A. Circuit Schematic

As previously mentioned, various configurations for the programmable blood processing circuit 46 are possible. FIG. schematically shows one representative configuration 46, the programmable features of which have been described. FIG. 34 shows another representative configuration of a blood processing circuit 46' having comparable programmable features.

Like the circuit 46, the circuit 46' includes several pump stations PP(N), which are interconnected by a pattern of fluid flow paths F(N) through an array of in line valves V(N). The circuit is coupled to the remainder of the blood processing set by ports P(N).

The circuit 46' includes a programmable network of flow paths F1 to F33. The circuit 46' includes eleven universal ports P1 to P8 and P11 to P13 and four universal pump stations PP1, PP2, PP3, and PP4. By selective operation of the in line valves V1 to V21 and V23 to V25, any universal port P1 to P8 and P11 to P13 can be placed in flow communication with any universal pump station PP1, PP2, PP3, and PP4. By selective operation of the universal valves, fluid flow can be directed through any universal pump station in a forward direction or reverse direction between two valves, or an in-out direction through a single valve.

In the illustrated embodiment, the circuit 46' also includes an isolated flow path (comprising flow paths F9, F23, F24, and F10) with two ports P9 and P10 and one in line pump station PP5. The flow path is termed "isolated," because it cannot be placed into direct flow communication with any other flow path in the circuit 46' without exterior tubing. By selective operation of the in line valves V21 and V22, fluid flow can be directed through the pump station PP5 in a forward direction or reverse direction between two valves, or an in-out direction through a single valve.

Like circuit 46, the circuit 46' can be programmed to assigned dedicated pumping functions to the various pump stations. In a preferrred embodiment, the universal pump stations PP3 and PP4 in tandem serve as a general purpose, donor interface pump, regardless of the particular blood procedure performed. The dual donor interface pump stations PP3 and PP4 in the circuit 46' work in parallel. One pump station draws fluid into its pump chamber, while the other pump station is expels fluid from its pump chamber. The pump station PP3 and PP4 alternate draw and expel functions.

In a preferred arrangement, the draw cycle for the drawing pump station is timed to be longer than the expel cycle for the expelling pump station. This provides a continuous flow of fluid on the inlet side of the pump stations and a pulsatile flow in the outlet side of the pump stations. In one representative embodiment, the draw cycle is ten seconds, and the expel cycle is one second. The expelling pump station performs its one second cycle at the beginning of the draw cycle of the drawing pump, and then rests for the remaining nine seconds of the draw cycle. The pump stations then switch draw and expel functions. This creates a continuous inlet flow and a pulsatile outlet flow. The provision of two alternating pump stations PP3 and PP4 serves to reduce overall processing time, as fluid is continuously conducted into a drawing pump station through out the procedure.

In this arrangement, the isolated pump station PP5 of the circuit 46' serves as a dedicated anticoagulant pump, like pump station PP4 in the circuit 46, to draw anticoagulant from a source through the port P10 and to meter anticoagulant into the blood through port P9.

In this arrangement, as in the circuit 46, the universal pump station PP1 serves, regardless of the particular blood processing procedure performed, as a dedicated in-process whole blood pump, to convey whole blood into the blood separator. As in the circuit 46, the dedicated function of the pump station PP1 frees the donor interface pumps PP3 and PP4 from the added function of supplying whole blood to the blood separator. Thus, the in-process whole blood pump PP1 can maintain a continuous supply of blood to the blood separator, while the donor interface pumps PP3 and PP4 operate in tandem to simultaneously draw and return blood to the donor through the single phlebotomy needle. The circuit 46' thus minimizes processing time.

In this arrangement, as in circuit 46, the universal pump station PP2 of the circuit 46' serves, regardless of the particular blood processing procedure performed, as a plasma pump, to convey plasma from the blood separator. As in the circuit 46, the ability to dedicate separate pumping functions in the circuit 46' provides a continuous flow of blood into and out of the separator, as well as to and from the donor.

The circuit 46' can be programmed to perform all the different procedures described above for the circuit 46. Depending upon the objectives of the particular blood processing procedure, the circuit 46' can be programmed to retain all or some of the plasma for storage or fractionation purposes, or to return all or some of the plasma to the donor. The circuit 46' can be further programmed, depending upon the objectives of the particular blood processing procedure, to retain all or some of the red blood cells for storage, or to return all or some of the red blood cells to the donor. The circuit 46' can also be programmed, depending upon the objectives of the particular blood processing procedure, to retain all or some of the buffy coat for storage, or to return all or some of the buffy coat to the donor.

In a preferred embodiment (see FIG. 34), the circuit 46' forms a part of a universal set 264', which is coupled to the ports P1 to P13.

More particularly, a donor tube 266', with attached phlebotomy needle 268' is coupled to the port P8 of the circuit 46'. An anticoagulant tube 270', coupled to the phlebotomy needle 268' is coupled to port P9. A container 276' holding anticoagulant is coupled via a tube 274' to the port P10.

A container 280' holding a red blood cell additive solution is coupled via a tube 278' to the port P3. A container 288' holding saline is coupled via a tube 284' to the port P12. A storage container 289' is coupled via a tube 291' to the port P13. An in-line leukocyte depletion filter 293' is carried by the tube 291' between the port P13 and the storage container 289'. The containers 276', 280', 288', and 289' can be integrally attached to the ports or can be attached at the time of use through a suitable sterile connection, to thereby maintain a sterile, closed blood processing environment.

Tubes 290', 292', and 294', extend to an umbilicus 296' which is coupled to the processing chamber 18'. The tubes 290', 292', and 294 are coupled, respectively, to the ports P5, P6, and P7. The tube 290' conveys whole blood into the processing chamber 18 under the operation of the in-process pump station PP1. The tube 292' conveys plasma from the processing chamber 18' under the operation of the plasma pump chamber PP2. The tube 294' conveys red blood cells from processing chamber 18'.

A plasma collection container 304' is coupled by a tube 302' to the port P3. The collection container 304' is intended, in use, to serve as a reservoir for plasma during processing.

A red blood cell collection container 308' is coupled by a tube 306' to the port P2. The collection container 308' is intended, in use, to receive a unit of red blood cells for storage.

A buffy coat collection container 376' is coupled by a tube 377' to the port P4. The container 376' is intended, in use, to receive a volume of buffy coat for storage.

A whole blood reservoir 312' is coupled by a tube 310' to the port P1. The collection container 312' is intended, in use, to receive whole blood during operation of the donor interface pumps PP3 and PP4, to serve as a reservoir for whole blood during processing. It can also serve to receive a second unit of red blood cells for storage.

B. The Cassette

Figure 35:
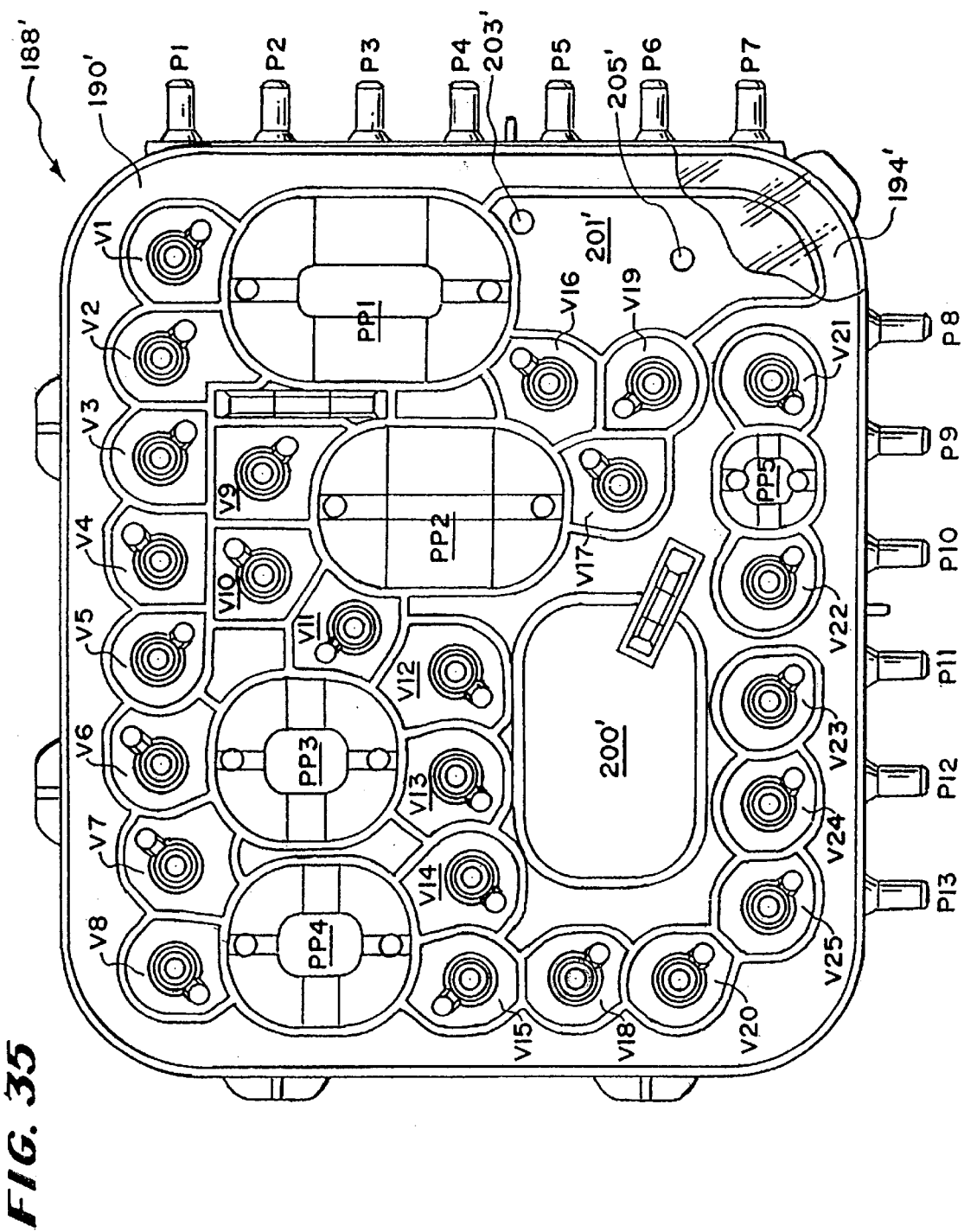
FIG. 35 is plane view of the front side of a cassette, which contains the programmable blood processing circuit shown in FIG. 34.
Figure 36:
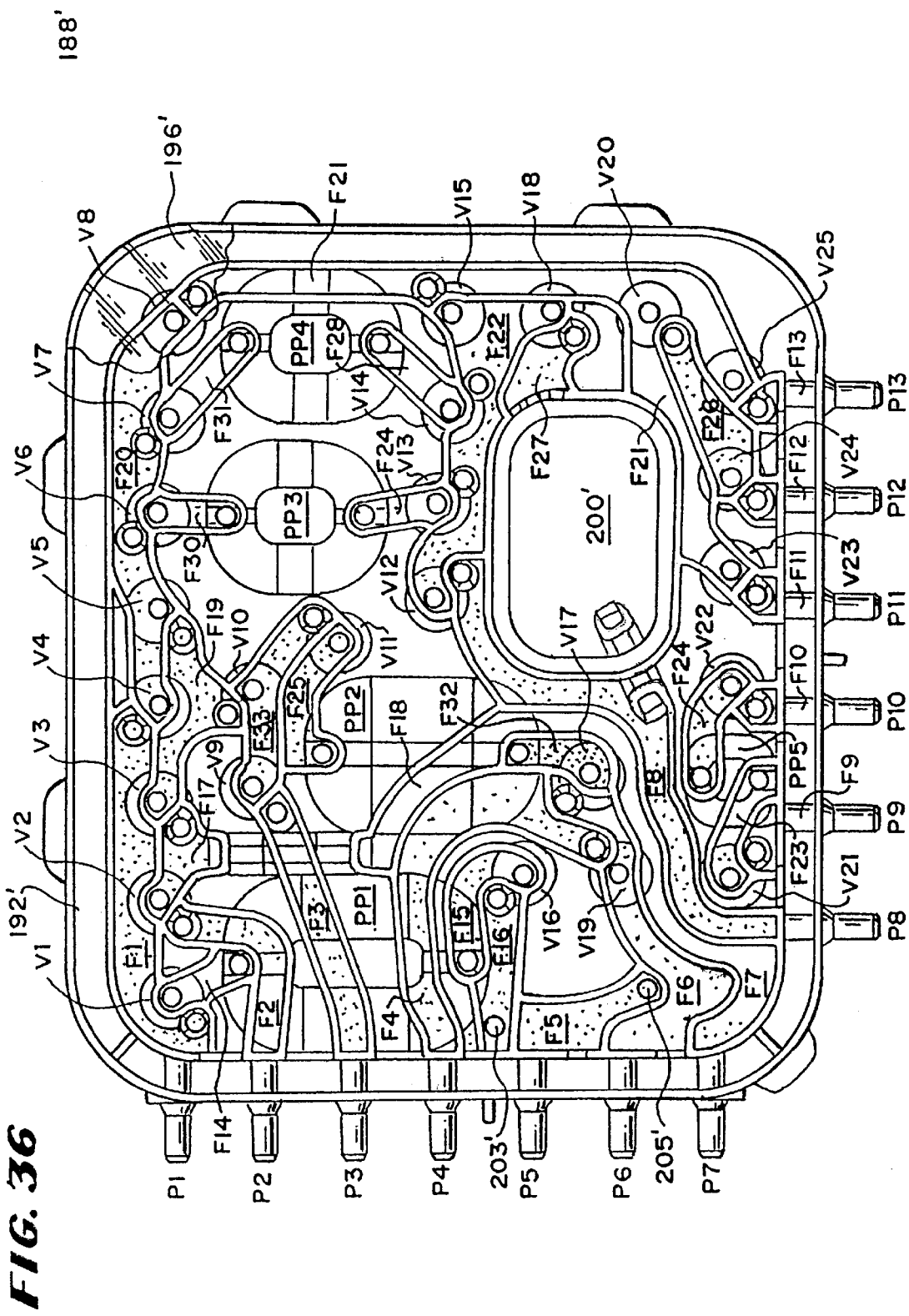
FIG. 36 is a plane view of the back side of the cassette shown in FIG. 35.

As FIGS. 35 and 36 show, the programmable fluid circuit 46' can be implemented as an injection molded, pneumatically controlled cassette 28'. The cassette 28' interacts with the pneumatic pump and valve station 30, as previously described, to provide the same centralized, programmable, integrated platform as the cassette 28.

FIG. 35 and 36 show the cassette 28' in which the fluid circuit 46' (schematically shown in FIG. 34) is implemented. As previously described for the cassette 28, an array of interior wells, cavities, and channels are formed on both the front and back sides 190' and 192' of the cassette body 188', to define the pump stations PP1 to PP5, valve stations V1 to V25, and flow paths F1 to F33 shown schematically in FIG. 34.

In FIG. 36, the flow paths F1 to F33, are shaded to facilitate their viewing. Flexible diaphragms 194' and 196' overlay the front and back sides 190' and 192' of the cassette body 188', resting against the upstanding peripheral edges surrounding the pump stations PP1 to PP5, valves V1 to V25, and flow paths F1 to F33. The pre-molded ports P1 to P13 extend out along two side edges of the cassette body 188'.

The cassette 28' is vertically mounted for use in the pump and valve station 30 in the same fashion shown in FIG. 2. In this orientation (which FIG. 36 shows), the side 192' faces outward, ports P8 to P13 face downward, and the ports P1 to P7 are vertically stacked one above the other and face inward.

As previously described, localized application by the pump and valve station 30 of positive and negative fluid pressures upon the diaphragm 194' serves to flex the diaphragm to close and open the valve stations V1 to V25 or to expel and draw liquid out of the pump stations PP1 to PP5.

An additional interior cavity 200' is provided in the back side 192' of the cassette body 188'. The cavity 200' forms a station that holds a blood filter material to remove clots and cellular aggregations that can form during blood processing. As shown schematically in FIG. 34, the cavity 200' is placed in the circuit 46' between the port P8 and the donor interface pump stations PP3 and PP4, so that blood returned to the donor passes through the filter. Return blood flow enters the cavity 200' through flow path F27 and exits the cavity 200' through flow path F8. The cavity 200' also serves to trap air in the flow path to and from the donor.

Another interior cavity 201' (see FIG. 35) is also provided in the back side 192' of the cassette body 188'. The cavity 201' is placed in the circuit 46' between the port P5 and the valve V16 of the in-process pumping station PP1. Blood enters the cavity 201' from flow path F16 through opening 203' and exits the cavity 201' into flow path F5 through opening 205' The cavity 201' serves as another air trap within the cassette body 188' in the flow path serving the separation chamber 26'. The cavity 201' also serves as a capacitor to dampen the pulsatile pump strokes of the in-process pump PP1 serving the separation chamber.

C. Associated Pneumatic Manifold Assembly

FIG. 43 shows a pneumatic manifold assembly 226' that can be used in association with the cassette 28', to supply positive and negative pneumatic pressures to convey fluid through the cassette 28'. The front side 194' of the diaphragm is held in intimate engagement against the manifold assembly 226' when the door 32 of the pump station 20 is closed and bladder 314 inflated. The manifold assembly 226', under the control of the controller 16, selectively distributes the different pressure and vacuum levels to the pump and valve actuators PA(N) and VA(N) of the cassette 28'. These levels of pressure and vacuum are systematically applied to the cassette 28', to route blood and processing liquids. Under the control of a controller 16, the manifold assembly 226 also distributes pressure levels to the door bladder 314 (already described), as well as to a donor pressure cuff (also already described) and to a donor line occluder 320 (also already described). The manifold assembly 226' for the cassette 28' shown in FIG. 43 shares many attributes with the manifold assembly 226 previously described for the cassette 28, as shown in FIG. 12.

Like the manifold assembly 226, the manifold assembly 226' is coupled to a pneumatic pressure source 234', which is carried inside the lid 40 behind the manifold assembly 226'. As in manifold assembly 226, the pressure source 234' for the manifold assembly 226 comprises two compressors C1' and C2', although one or several dual-head compressors could be used as well. Compressor C1 supplies negative pressure through the manifold 226' to the cassette 28'. The other compressor C2' supplies positive pressure through the manifold 226' to the cassette 28.

As FIG. 43 shows, the manifold 226' contains five pump actuators PA1 to PA4 and twenty-five valve actuators VA1 to VA25. The pump actuators PA1 to PA5 and the valve actuators VA1 to VA25 are mutually oriented to form a mirror image of the pump stations PP1 to PP5 and valve stations V1 to V25 on the front side 190' of the cassette 28'.

Like the manifold assembly 226, the manifold assembly 226' shown in FIG. 43 includes an array of solenoid actuated pneumatic valves, which are coupled in-line with the pump and valve actuators PA1 to PA5 and VA1 to VA25.

Like the manifold assembly 226, the manifold assembly 226' maintains several different pressure and vacuum conditions, under the control of the controller 16.

As previously described in connection with the manifold assembly 226, Phard, or Hard Pressure, and Pinpr, or In-Process Pressure are high positive pressures (e.g., +500 mmHg) maintained by the manifold assembly 226' for closing the cassette valves V1 to V25 and to drive the expression of liquid from the in-process pump PP1 and the plasma pump PP2. As before explained, the magnitude of Pinpr must be sufficient to overcome a minimum pressure of approximately 300 mm Hg, which is typically present within the processing chamber 18. Pinpr and Phard are operated at the highest pressure to ensure that upstream and downstream valves used in conjunction with pumping are not forced opened by the pressures applied to operate the pumps.

Pgen, or General Pressure (+300 mmHg), is applied to drive the expression of liquid from the donor interface pumps PP3 and PP4 and the anticoagulant pump PP5.

Vhard, or Hard Vacuum (−350 mmHg), is the deepest vacuum applied in the manifold assembly 226' to open cassette valves V1 to V25. Vgen, or General Vacuum (−300 mmHg), is applied to drive the draw function of each of the pumps PP1 to PP5. Vgen is required to be less extreme than Vhard, to ensure that pumps PP1 to PP5 do not overwhelm upstream and downstream cassette valves V1 to V25.

A main hard pressure line 322' and a main vacuum line 324' distribute Phard and Vhard in the manifold assembly 324. The pressure and vacuum sources 234' run continuously to supply Phard to the hard pressure line 322' and Vhard to the hard vacuum line 324'. A pressure sensor S2 monitors Phard in the hard pressure line 322'. The sensor S2 opens and closes the solenoid 38 to build Phard up to its maximum set value.

Similarly, a pressure sensor S6 in the hard vacuum line 324' monitors Vhard. The sensor S6 controls a solenoid 43 to maintain Vhard as its maximum value.

A general pressure line 326' branches from the hard pressure line 322'. A sensor S4 in the general pressure line 326' monitors Pgen. The sensor S2 controls a solenoid 34 to maintain Pgen within its specified pressure range.

A general vacuum line 330' branches from the hard vacuum line 324'. A sensor S5 monitors Vgen in the general vacuum line 330'. The sensor S5 controls a solenoid 45 to keep Vgen within its specified vacuum range.

In-line reservoirs R1 to R4 are provided in the hard pressure line 322, the general pressure line 326', the hard vacuum line 324', and the general vacuum line 330'. The reservoirs R1 to R4 assure that the constant pressure and vacuum adjustments as above described are smooth and predictable.

The solenoids 32 and 43 provide a vent for the pressures and vacuums, respectively, upon procedure completion.

The solenoids 41, 2, 46, and 47 provide the capability to isolate the reservoirs R1 to R4 from the air lines that supply vacuum and pressure to the pump and valve actuators. This provides for much quicker pressure/vacuum decay feedback, so that testing of cassette/manifold assembly seal integrity can be accomplished.

The solenoids 1 to 25 provide Phard or Vhard to drive the valve actuators VA1 to VA25. The solenoids 27 and 28 provide Pinpr and Vgen to drive the in-process and plasma pumps PP1 and PP2. The solenoids 30 and 31 provide Pgen and Vgen to drive the donor interface pumps actuators PA3 and PA4. The solenoid 29 provides Pgen and Vgen to drive the AC pump actuator PP5.

The solenoid 35 provides isolation of the door bladder 314 from the hard pressure line 322' during the procedure. A sensor S1 monitors Pdoor and control the solenoid 35 to keep the pressure within its specified range.

The solenoid 40 provides Phard to open the safety occluder valve 320'. Any error modes that might endanger the donor will relax (vent) the solenoid 40 to close the occluder 320' and isolate the donor. Similarly, any loss of power will relax the solenoid 40 and isolate the donor.

The sensor S3 monitors Pcuff and communicates with solenoids 36 (for increases in pressure) and solenoid 37 (for venting) to maintain the donor cuff within its specified ranges during the procedure.

As before explained, any solenoid can be operated in "normally open" mode or can be re-routed pneumatically to be operated in a "normally closed" mode, and vice versa.

D. Exemplary Pumping Functions

Based upon the foregoing description of the programming of the fluid circuit 46 implemented by the cassette 28, one can likewise program the fluid circuit 46' implemented by the cassette 28' to perform all the various blood process functions already described. Certain pumping functions for the fluid circuit 46', common to various blood processing procedures, will be described by way of example.

1. Whole Blood Flow To the In-Process Container

In a first phase of a given blood collection cycle, the blood processing circuit 46' is programmed (through the selective application of pressure to the valves and pump stations of the cassette 28') to jointly operate the donor interface pumps PP3 and PP4 to transfer anticoagulated whole blood into the in-process container 312' prior to separation.

Figure 37A:
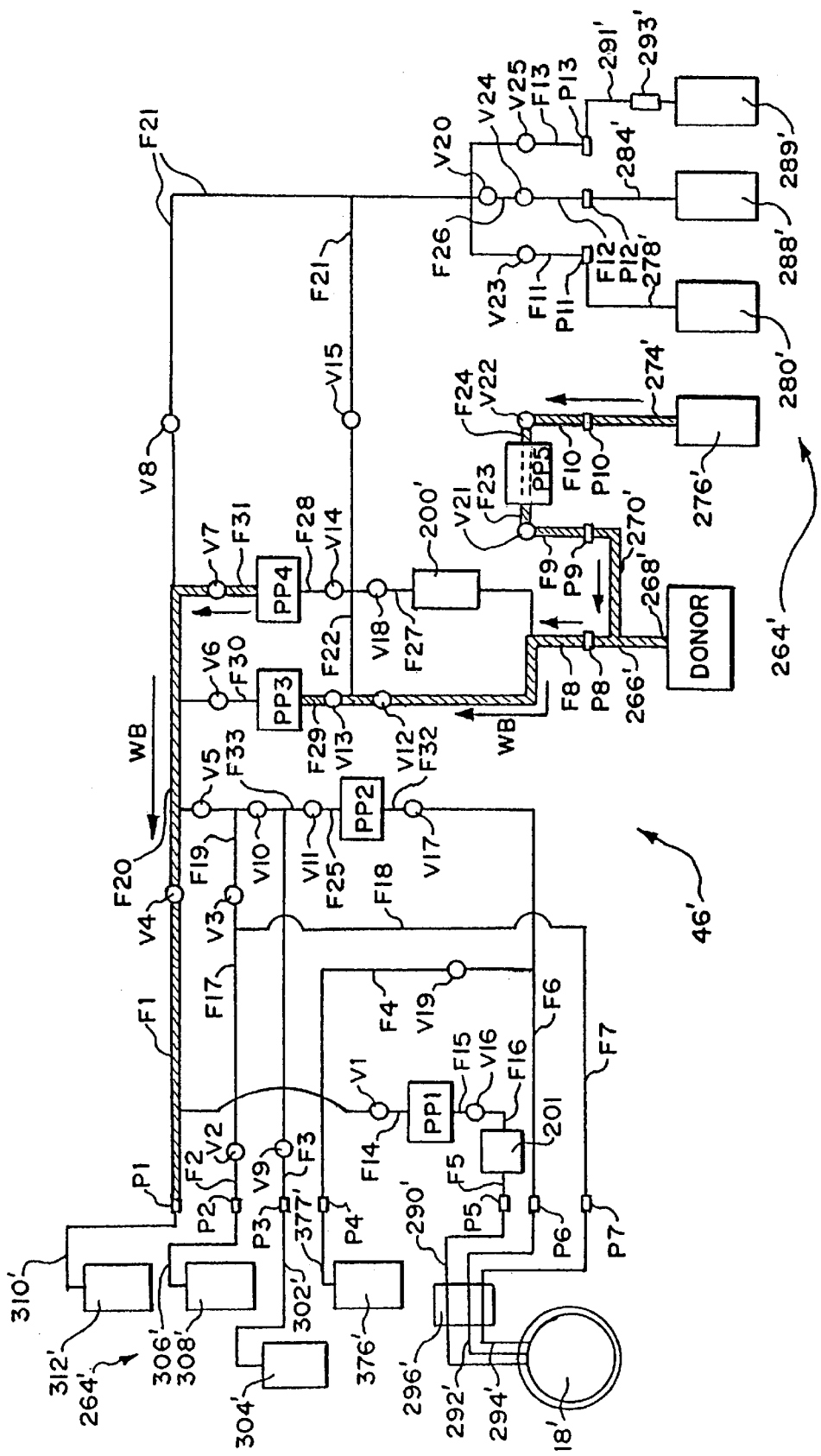
FIGS. 37A to 37E are schematic views of the blood processing circuit shown in FIG. 34, showing the programming of the cassette to carry out different fluid flow tasks in connection with processing whole blood into plasma and red blood cells.

In a first phase (see FIG. 37A), the pump PP3 is operated in a ten second draw cycle(i.e., in through valves V12 and V13, with valves V6, V14, V18, and V15 closed) in tandem with the anticoagulant pump PP5 (i.e., in through valve V22 and out through valve V21) to draw anticoagulated blood through the donor tube 270 into the pump PP3. At the same time, the donor interface pump PP4 is operated in a one second expel cycle to expel (out through valve V7) anticoagulant blood from its chamber into the process container 312' through flow paths F20 and F1 (through opened valve V4).

Figure 37B:
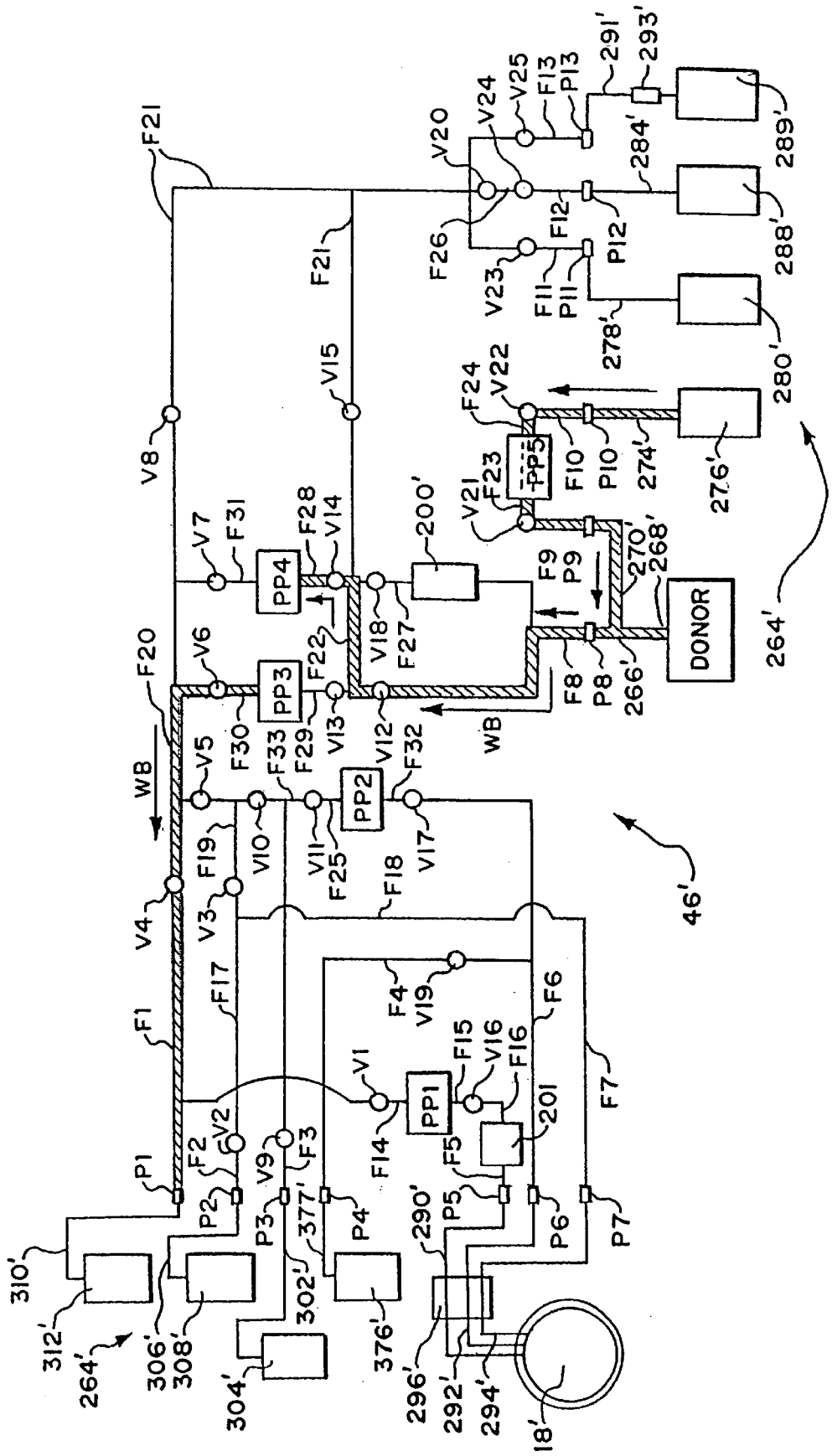

At the end of the draw cycle for pump PP3 (see FIG. 37B), the blood processing circuit 46' is programmed to operate the donor interface pump PP4 in a ten second draw cycle (i.e., in through valves V12 and V14, with valves V13, V18, and V18 closed) in tandem with the anticoagulant pump PP5 to draw anticoagulated blood through the donor tube 270 into the pump PP4. At the same time, the donor interface pump PP3 is operated in a one second expel cycle to expel (out through valve V6) anticoagulant blood from its chamber into the process container 312' through the flow paths F20 and F1 (through opened valve V4).

Figure 37C:
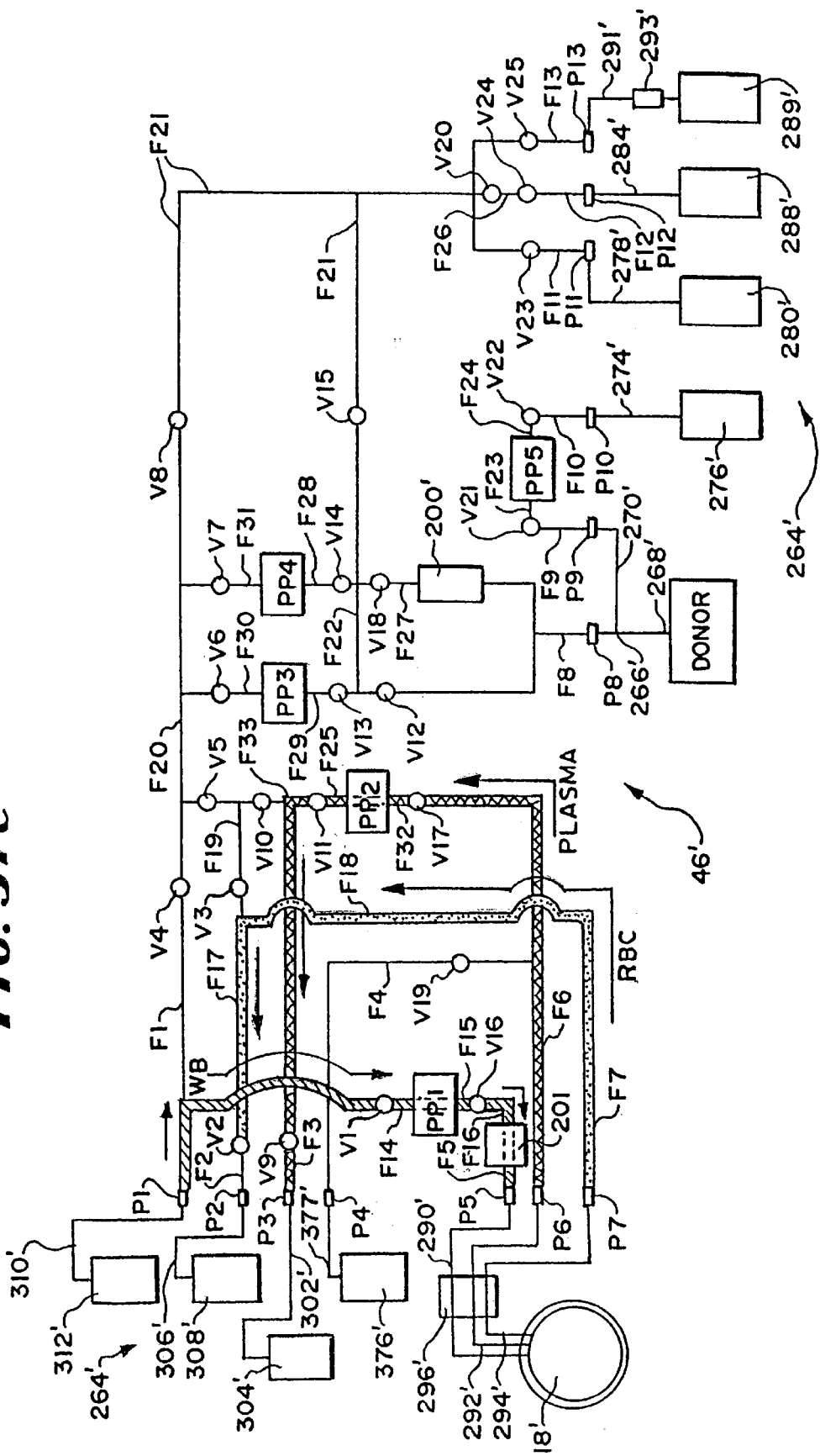

These alternating cycles continue until an incremental volume of anticoagulated whole blood enters the in process container 312', as monitored by a weigh sensor. As FIG. 37C shows, the blood processing circuit 46' is programmed to operate the in-process pump station PP1 (i.e., in through valve V1 and out through valve V16) and the plasma pump PP2 (i.e., in through valve V17 and out through valve V11, with valve V9 opened and valve V10 closed) to convey anticoagulated whole blood from the in-process container 312 into the processing chamber 18' for separation, while removing plasma into the plasma container 304 (through opened valve V9) and red blood cells into the red blood cell container 308 (through open valve V2), in the manner previously described with respect to the circuit 46. This phase continues until an incremental volume of plasma is collected in the plasma collection container 304 (as monitored by the weigh sensor) or until a targeted volume of red blood cells is collected in the red blood cell collection container (as monitored by the weigh sensor). The donor interface pumps PP3 and PP4 toggle to perform alternating draw and expel cycles as necessary to keep the volume of anticoagulated whole blood in the in-process container 312' between prescribed minimum and maximum levels, as blood processing proceeds.

2. Red Blood Cell Return with In-Line Addition of Saline

Figure 37D:
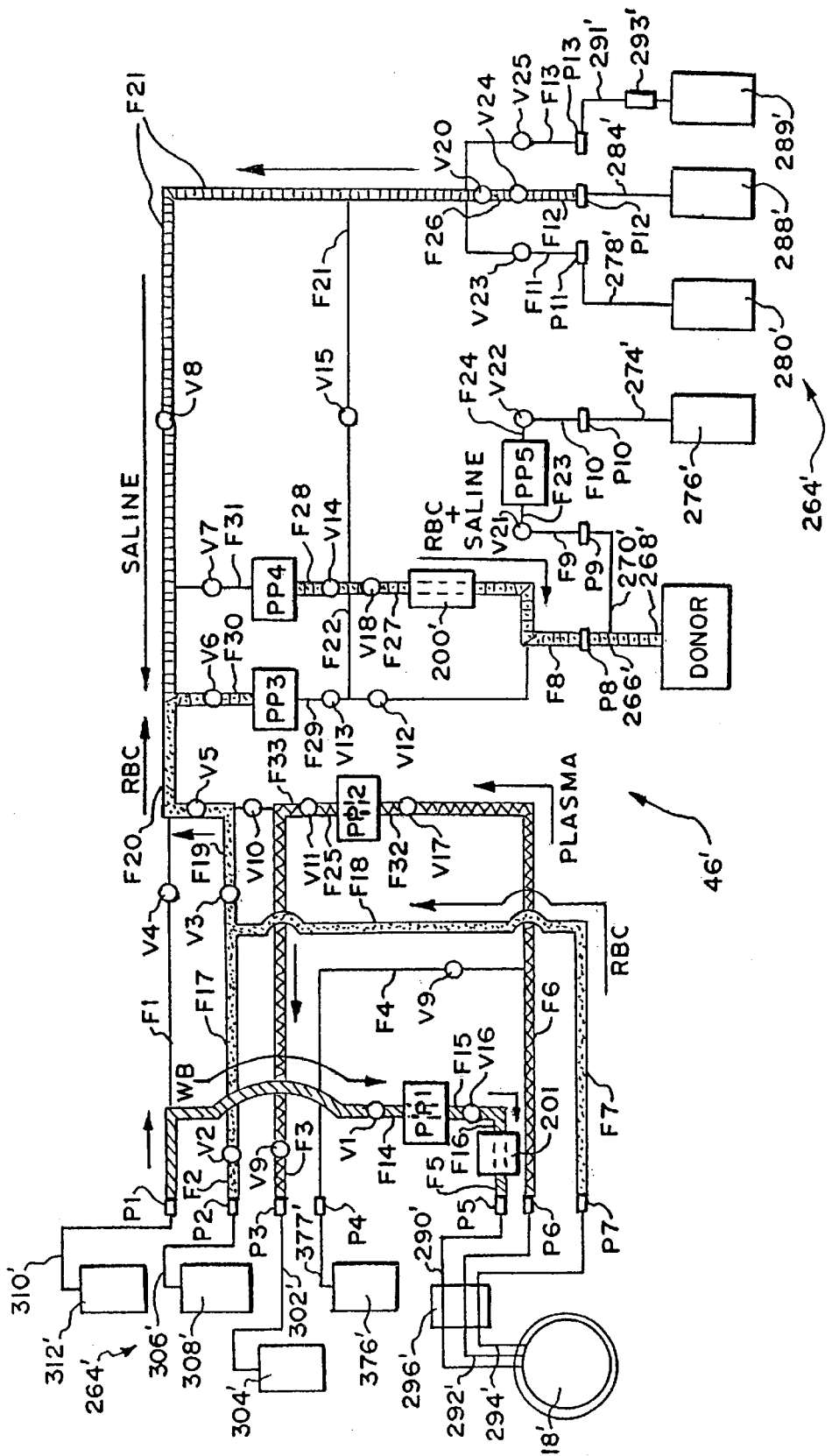

When it is desired to return red blood cells to the donor (see FIG. 37D), the blood processing circuit 46' is programmed to operate the donor interface pump station PP3 in a ten second draw cycle(i.e., in through valve V6, with valves V13 and V7 closed) to draw red blood cells from the red blood cell container 308' into the pump PP3 (through open valves V2, V3, and V5, valve V10 being closed). At the same time, the donor interface pump PP4 is operated in a one second expel cycle to expel (out through valves V14 and V18, with valves V12 and V21 closed) red blood cells from its chamber to the donor through the filter cavity 200'.

Figure 37E:
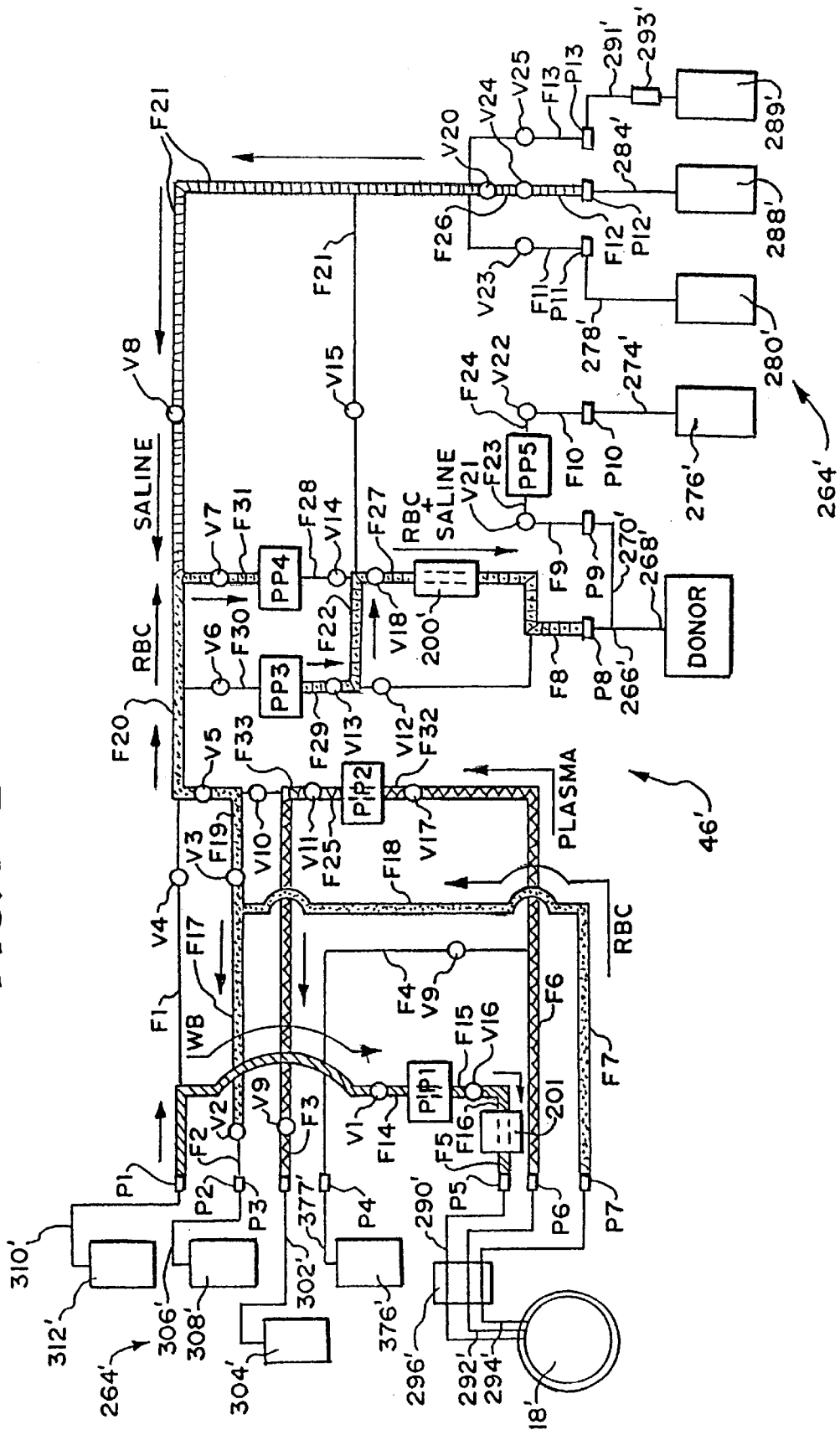

At the end of the draw cycle for pump PP3 (see FIG. 37E), the blood processing circuit 46' is programmed to operate the donor interface pump PP4 in a ten second draw cycle (i.e., in through valve V7, with valves V6 and V14 closed) to draw red blood cells from the red blood cell container 308' into the pump PP4. At the same time, the donor interface pump PP3 is operated in a one second expel cycle to expel (out through valves V13 and V18, with valve V12 closed) red blood cells from its chamber to the donor through the filter chamber 200'. These alternating cycles continue until a desired volume of red blood cells are returned to the donor.

Simultaneously, valves V24, V20, and V8 are opened, so that the drawing pump station PP3 or PP4 also draws saline from the saline container 288' for mixing with red blood cells drawn into the chamber. As before explained, the in line mixing of saline with the red blood cells raises the saline temperature and improves donor comfort, while also lowering the hematocrit of the red blood cells.

Simultaneously, the in-process pump PP1 is operated (i.e., in through valve V1 and out through valve V16) and the plasma pump PP2 (i.e., in through valve V17 and out through valve V11, with valve V9 open) to convey anticoagulated whole blood from the in-process container 312 into the processing chamber for separation, while removing plasma into the plasma container 304, in the manner previously described with respect to the fluid circuit 46.

3. In-Line Addition of Red Blood Cell Additive Solution

Figure 38A:
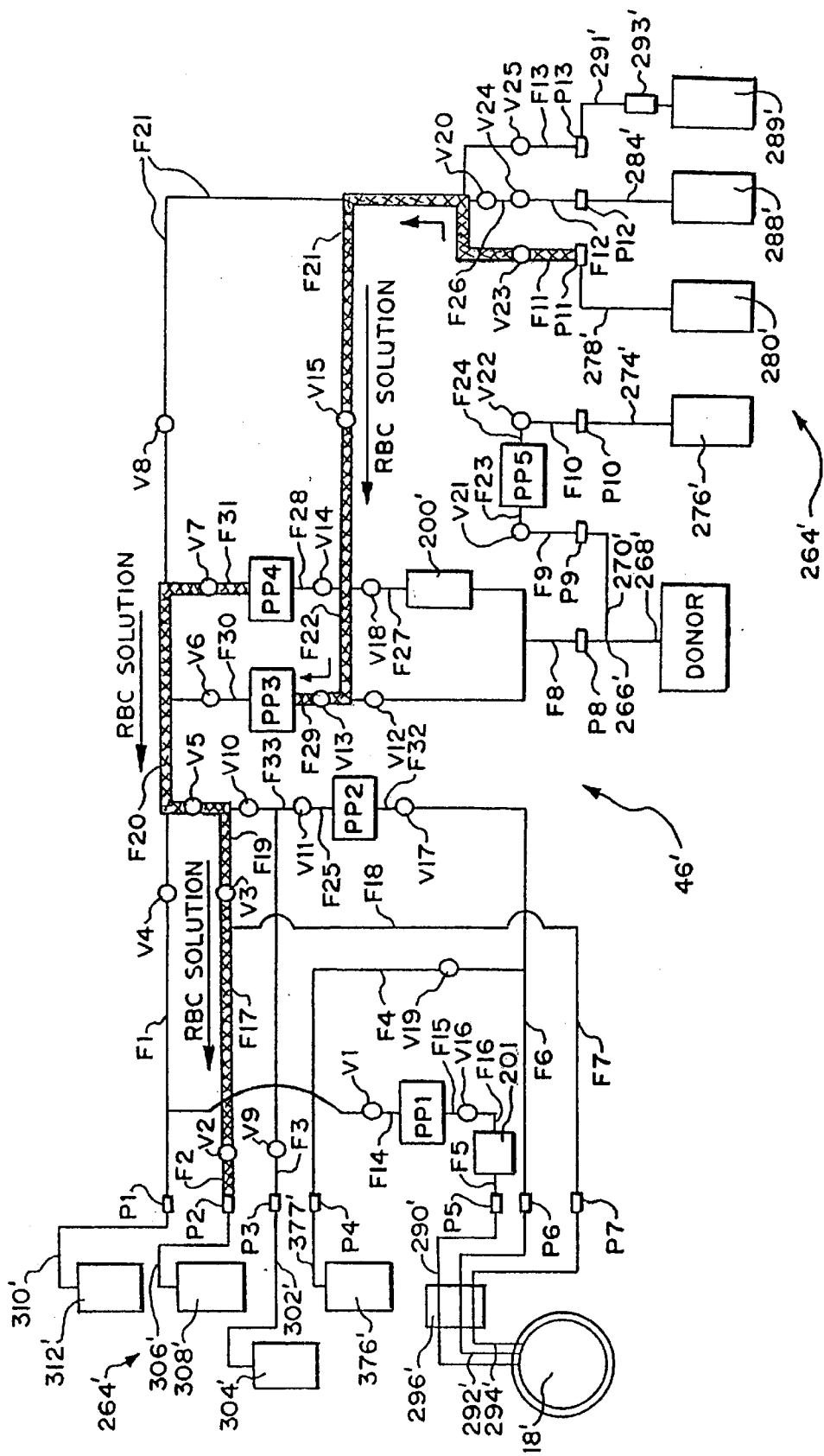
FIGS. 38A and 38B are schematic views of the blood processing circuit shown in FIG. 34, showing the programming of the cassette to carry out fluid flow tasks in connection with on-line transfer of an additive solution into red blood cells separated from whole blood.

In a blood processing procedure where red blood cells are collected for storage (e.g., the Double Red Blood Cell Collection Procedure or the Red Blood Cell and Plasma Collection Procedure) the circuit 46' is programmed to operate the donor interface pump station PP3 in a ten second draw cycle(in through valves V15 and V13, with valve V23 opened and valves V8, V12 and V18 closed) to draw red blood cell storage solution from the container 280' into the pump PP3 (see FIG. 38A). Simultaneously, the circuit 46' is programmed to operate the donor interface pump station PP4 in a one second expel cycle(out through valve V7, with valves V14 and V18 closed) to expel red blood cell storage solution to the container(s) where red blood cells reside (e.g., the in-process container 312 (through open valve V4) or the red blood cell collection container 308' (through open valves V5, V3, and V2, with valve V10 closed).

Figure 38B:
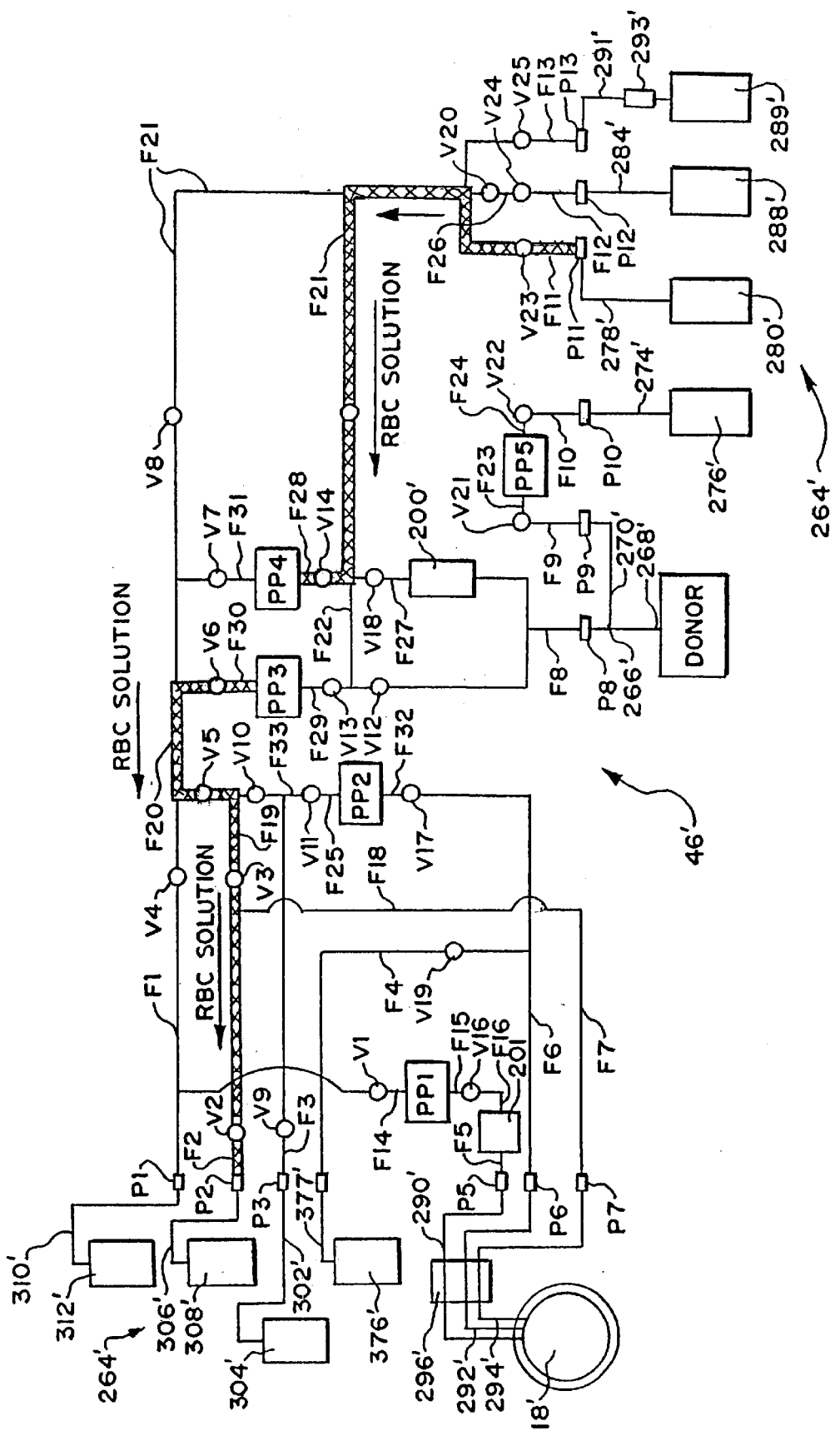

At the end of the draw cycle for pump PP3 (see FIG. 38B), the blood processing circuit 46' is programmed to operate the donor interface pump PP4 in a ten second draw cycle (i.e., in through valve V14, with valves V7, V18, V12, and V13 closed) to draw red blood cell storage solution from the container 280' into the pump PP4. At the same time, the donor interface pump PP3 is operated in a one second expel cycle to expel (out through valve V6, with valves V13 and V12 closed) red blood cell storage solution to the container (s) where red blood cells reside. These alternating cycles continue until a desired volume of red blood cell storage solution is added to the red blood cells.

4. In-Line Leukocyte Depletion

Figure 39A:
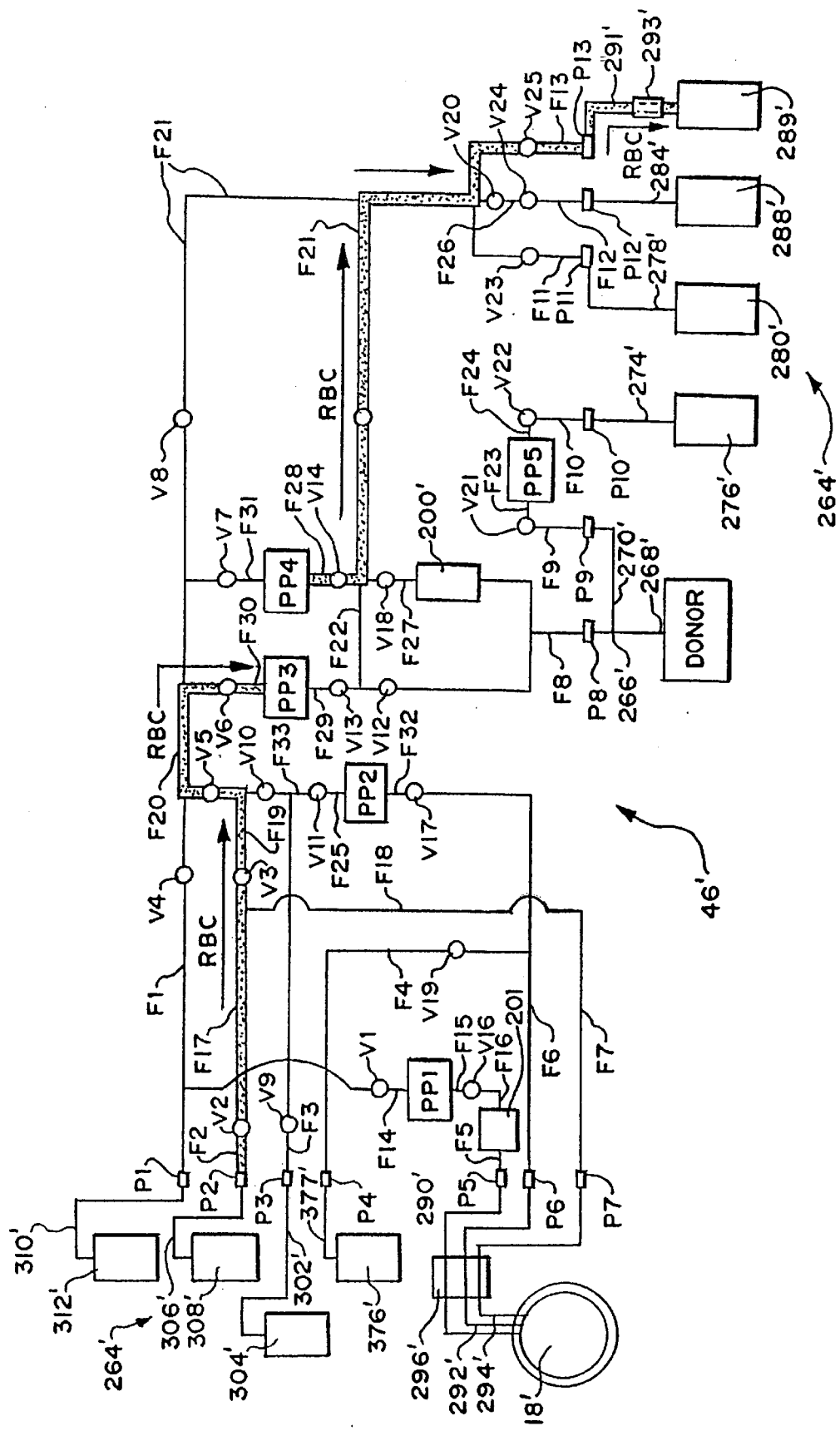
FIGS. 39A and 39B are schematic views of the blood processing circuit shown in FIG. 34, showing the programming of the cassette to carry out fluid flow tasks in connection with on-line transfer of red blood cells separated from whole blood through a filter to remove leukocytes.

Circuit 46' provides the capability to conduct on-line depletion of leukocytes from collected red blood cells. In this mode (see FIG. 39A), the circuit 46' is programmed to operate the donor interface pump station PP3 in a ten second draw cycle(in through valve V6, with valves V13 and V12 closed) to draw red blood cells from the container(s) where red blood cells reside (e.g., the in-process container 312' (through open valve V4) or the red blood cell collection container 308 (through open valves V5, V3, and V2, with valve V10 closed) into the pump PP3. Simultaneously, the circuit 46' is programmed to operate the donor interface pump station PP4 in a one second expel cycle(out through valve V14, with valves V18 and V8 closed and valves V15 and V25 opened) to expel red blood cells through tube 291' through the in-line leukocyte depletion filter 293' to the leukocyte-depleted red blood cell storage container 289'.

Figure 39B:
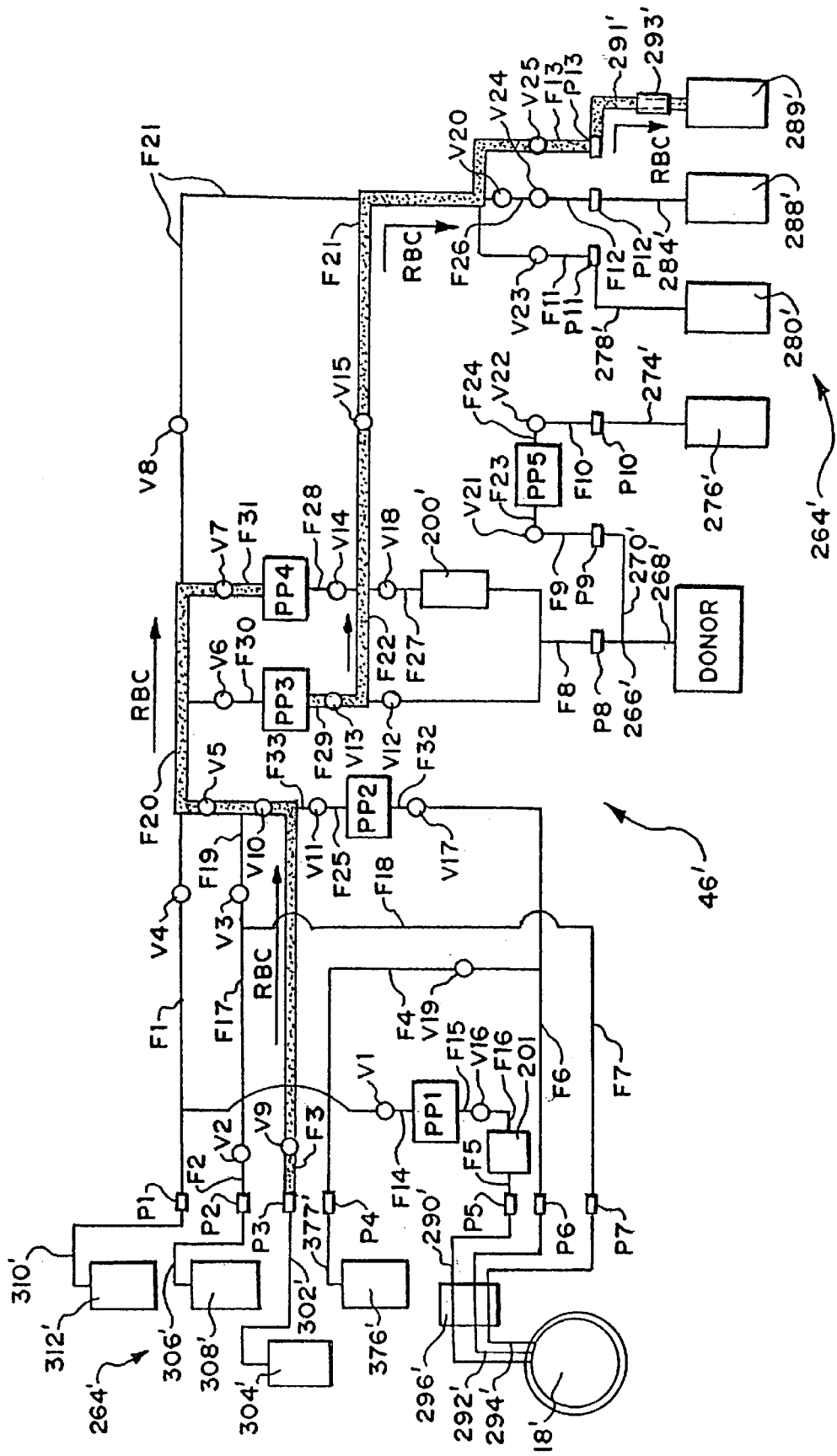

At the end of the draw cycle for pump PP3 (see FIG. 39B), the blood processing circuit 46' is programmed to operate the donor interface pump PP4 in a ten second draw cycle (i.e., in through valve V7, with valves V14 and V18 closed) to draw red blood cells from the container 312' or 308' into the pump PP4. At the same time, the donor interface pump PP3 is operated in a one second expel cycle to expel (out through valve V13, with valve V12 closed and valves V15 and V25 opened) red blood cells through tube 291' through the in-line leukocyte depletion filter 293' to the leukocyte-depleted red blood cell storage container 289'. These alternating cycles continue until a desired volume of red blood cells are transferred through the filter 293 into the container 289'.

5. Staged Buffy Coat Harvesting

In circuit 46 (see FIG. 5), buffy coat is collected through port P4, which is served by flow line F4, which branches from flow line F26, which conveys plasma from the plasma pump station PP2 to the plasma collection container 304 (also see FIG. 10). In the circuit 46' (see FIG. 34), the buffy coat is collected through the port P4 from the flow path F6 as controlled by valve V19. The buffy coat collection path bypasses the plasma pump station PP2, keeping the plasma pump station PP2 free of exposure to the buffy coat, thereby keeping the collected plasma free of contamination by the buffy coat components.

During separation, the system controller (already described) maintains the buffy coat layer within the separation chamber 18' at a distance spaced from the low-G wall, away from the plasma collection line 292 (see FIG. 15A). This allows the buffy coat component to accumulate during processing as plasma is conveyed by operation of the plasma pump PP2 from the chamber into the plasma collection container 304'.

To collect the accumulated buffy coat component, the controller opens the buffy coat collection valve V19, and closes the inlet valve V17 of the plasma pump station PP2 and the red blood cell collection valve V2. The in-process pump PP1 continues to operate, bringing whole blood into the chamber 181. The flow of whole blood into the chamber 18' moves the buffy coat to the low-G wall, inducing an over spill condition) (see FIG. 15B). The buffy coat component enters the plasma collection line 292' and enters flow path F6 through the port P6. The circuit 46' conveys the buffy coat component in F6 through the opened valve V19 directly into path F4 for passage through the port P4 into the collection container 376'.

The valve V19 is closed when the sensing station 332 senses the presence of red blood cells. The plasma pumping station PP2 can be temporarily operated in a reverse flow direction (in through the valve V11 and out through the valve V17, with valve V9 opened) to flow plasma from the collection container 302' through the tube 292' toward the separation chamber, to flush resident red blood from the tube 292' back into the separation chamber. The controller can resume normal plasma and red blood cell collection, by opening the red blood cell collection valve V2 and operating the plasma pumping station PP2 (in through valve V17 and out through valve V11) to resume the conveyance of plasma from the separation chamber to the collection container 302'.

Over spill conditions causing the movement of the buffy coat for collection can be induced at prescribed intervals during the process period, until a desired buffy coat volume is collected in the buffy coat collection container.

6. Miscellaneous

As FIG. 43 shows in phantom lines, the manifold assembly 226' can include an auxiliary pneumatic actuator $A_{AUX}$ selectively apply $P_{HARD}$ to the region of the flexible diaphragm that overlies the interior cavity 201' (see FIG. 35). As previously described, whole blood expelled by the pumping station PP1 (by application of $P_{HARD}$ by actuator PA2), enters flow path F5 through openings 203' and 205' into the processing chamber 18'. During the next subsequent stroke of the PP1, to draw whole blood into the pumping chamber PP1 by application of $V_{GEN}$ by actuator PA2, residual whole blood residing in the cavity 201' is expelled into flow path F5 through opening 205', and into the processing chamber 18' by application of $P_{HARD}$ by $A_{AUX}$. The cavity 201' also serves as a capacitor to dampen the pulsatile pump strokes of the in-process pump PP1 serving the separation chamber 18'.

It is desirable to conduct seal integrity testing of the cassette 28' shown in FIG. 35 and 36 prior to use. The integrity test determines that the pump and valve stations within the cassette 28' function without leaking. In this situation, it is desirable to isolate the cassette 28' from the separation chamber 26'. Valves V19 and V16 (see FIG. 34) in circuit 264' provide isolation for the whole blood inlet and plasma lines 292' and 296' of the chamber 18'. To provide the capability of also isolating the red blood cell line 294', an extra valve fluid actuated station V26 can be added in fluid flow path F7 serving port P7. As further shown in phantom lines in FIG. 43, an addition valve actuator VA26 can be added to the manifold assembly 26', to apply positive pressure to the valve V26, to close the valve V26 when isolation is required, and to apply negative pressure to the valve V26, to open the valve when isolation is not required.

VII. Blood Separation Elements

A. Molded Processing Chamber

Figure 21:
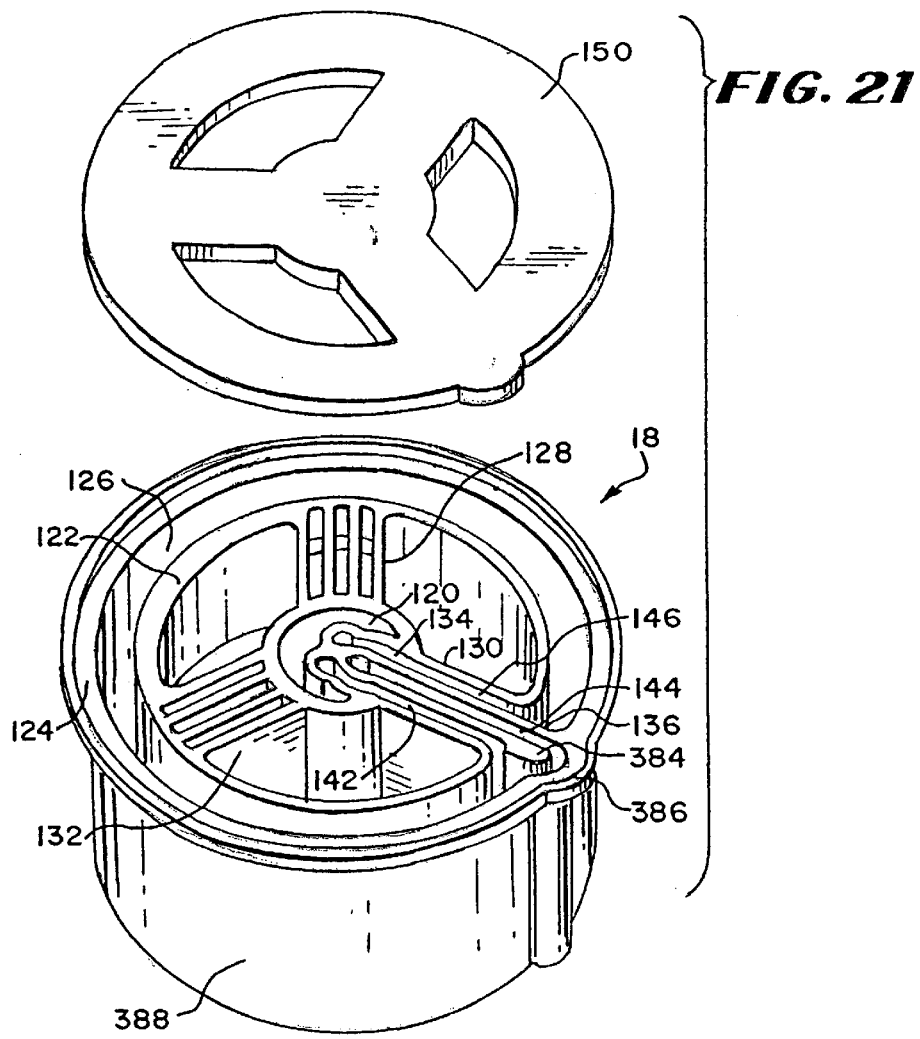
FIG. 21 is an exploded top perspective view of the of a molded centrifugal blood processing container, which can be used in association with the device shown in FIG. 1.

FIGS. 21 to 23 show an embodiment of the centrifugal processing chamber 18, which can be used in association with the system 10 shown in FIG. 1.

In the illustrated embodiment, the processing chamber 18 is preformed in a desired shape and configuration, e.g., by injection molding, from a rigid, biocompatible plastic material, such as a non-plasticized medical grade acrilonitrile-butadiene-styrene (ABS).

The preformed configuration of the chamber 18 includes a unitary, molded base 388. The base 388 includes a center hub 120. The hub 120 is surrounded radially by inside and outside annular walls 122 and 124 (see FIGS. 21 and 23). Between them, the inside and outside annular walls 122 and 124 define a circumferential blood separation channel 126. A molded annular wall 148 closes the bottom of the channel 126 (see FIG. 22).

The top of the channel 126 is closed by a separately molded, flat lid 150 (which is shown separated in FIG. 21 for the purpose of illustration). During assembly, the lid 150 is secured to the top of the chamber 18, e.g., by use of a cylindrical sonic welding horn.

All contours, ports, channels, and walls that affect the blood separation process are preformed in the base 388 in a single, injection molded operation. Alternatively, the base 388 can be formed by separate molded parts, either by nesting cup shaped subassemblies or two symmetric halves.

The lid 150 comprises a simple flat part that can be easily welded to the base 388. Because all features that affect the separation process are incorporated into one injection molded component, any tolerance differences between the base 388 and the lid 150 will not affect the separation efficiencies of the chamber 18.

The contours, ports, channels, and walls that are preformed in the base 388 can vary. In the embodiment shown in FIGS. 21 to 23, circumferentially spaced pairs of stiffening walls 128, 130, and 132 emanate from the hub 120 to the inside annular wall 122. The stiffening walls 128, 130, 132 provide rigidity to the chamber 18.

As seen in FIG. 23, the inside annular wall 122 is open between one pair 130 of the stiffening walls. The opposing stiffening walls form an open interior region 134 in the hub 120, which communicates with the channel 126. Blood and fluids are introduced from the umbilicus 296 into and out of the separation channel 126 through this region 134.

In this embodiment (as FIG. 23 shows), a molded interior wall 136 formed inside the region 134 extends entirely across the channel 126, joining the outside annular wall 124. The wall 136 forms a terminus in the separation channel 126, which interrupts flow circumferentially along the channel 126 during separation.

Additional molded interior walls divide the region 124 into three passages 142, 144, and 146. The passages 142, 144, and 146 extend from the hub 120 and communicate with the channel 126 on opposite sides of the terminus wall 136. Blood and other fluids are directed from the hub 120 into and out of the channel 126 through these passages 142, 144, and 146. As will be explained in greater detail later, the passages 142, 144, and 146 can direct blood components into and out of the channel 126 in various flow patterns.

The underside of the base 388 (see FIG. 22) includes a shaped receptacle 179. Three preformed nipples 180 occupy the receptacle 179. Each nipple 180 leads to one of the passages 142, 144, 146 on the opposite side of the base 388.

Figure 25:
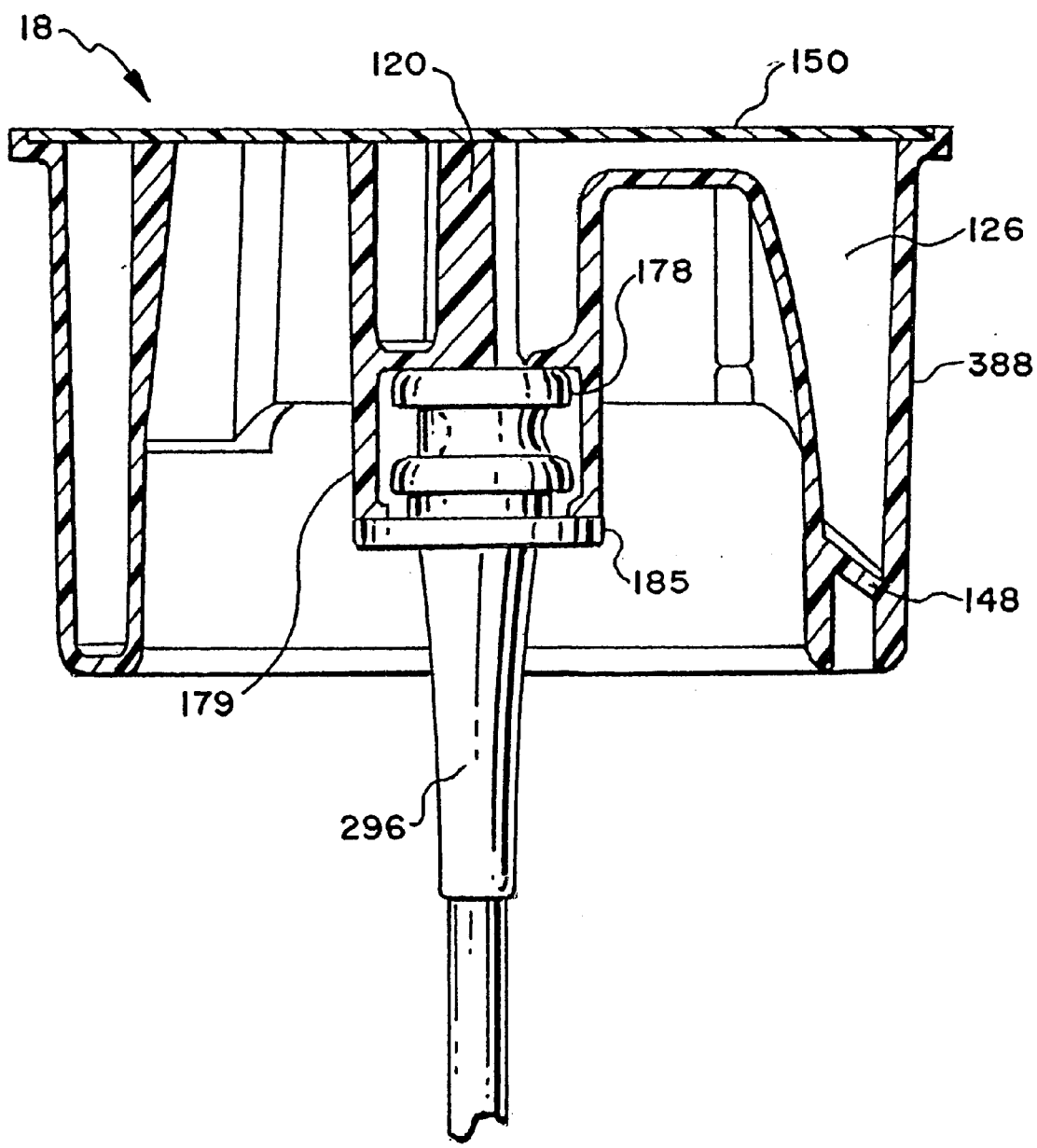
FIG. 25 is a side section view of the molded processing container shown in FIG. 24, after connection of the umbilicus to container.

The far end of the umbilicus 296 includes a shaped mount 178 (see FIGS. 24 and 24A). The mount 178 is shaped to correspond to the shape of the receptacle 179. The mount 178 can thus be plugged into the receptacle 179 (as FIG. 25 shows). The mount 178 includes interior lumens 398 (see FIG. 24A), which slide over the nipples 180 in the hub 120, to couple the umbilicus 296 in fluid communication with the channel 126.

Ribs 181 within the receptacle 179 (see FIG. 22) uniquely fit within a key way 183 formed on the mount 178 (see FIG.

24A). The unique fit between the ribs 181 and the key way 183 is arranged to require a particular orientation for plugging the shaped mount 178 into the shaped receptacle 179. In this way, a desired flow orientation among the umbilicus 296 and the passages 142, 144, and 146 is assured.

In the illustrated embodiment, the umbilicus 296 and mount 178 are formed from a material or materials that withstand the considerable flexing and twisting forces, to which the umbilicus 296 is subjected during use. For example, a Hytrel® polyester material can be used.

This material, while well suited for the umbilicus 296, is not compatible with the ABS plastic material of the base 388, which is selected to provide a rigid, molded blood processing environment. The mount 178 thus cannot be attached by conventional by solvent bonding or ultrasonic welding techniques to the receptacle 179.

In this arrangement (see FIGS. 24 and 25), the dimensions of the shaped receptacle 179 and the shaped mount 178 are preferably selected to provide a tight, dry press fit. In addition, a capturing piece 185, formed of ABS material (or another material compatible with the material of the base 388), is preferably placed about the umbilicus 296 outside the receptacle in contact with the peripheral edges of the receptacle 179. The capturing piece 185 is secured to the peripheral edges of the receptacle 179, e.g., by swaging or ultrasonic welding techniques. The capturing piece 185 prevents inadvertent separation of the mount 178 from the receptacle 181. In this way, the umbilicus 296 can be integrally connected to the base 388 of the chamber 18, even though incompatible plastic materials are used.

Figure 26:
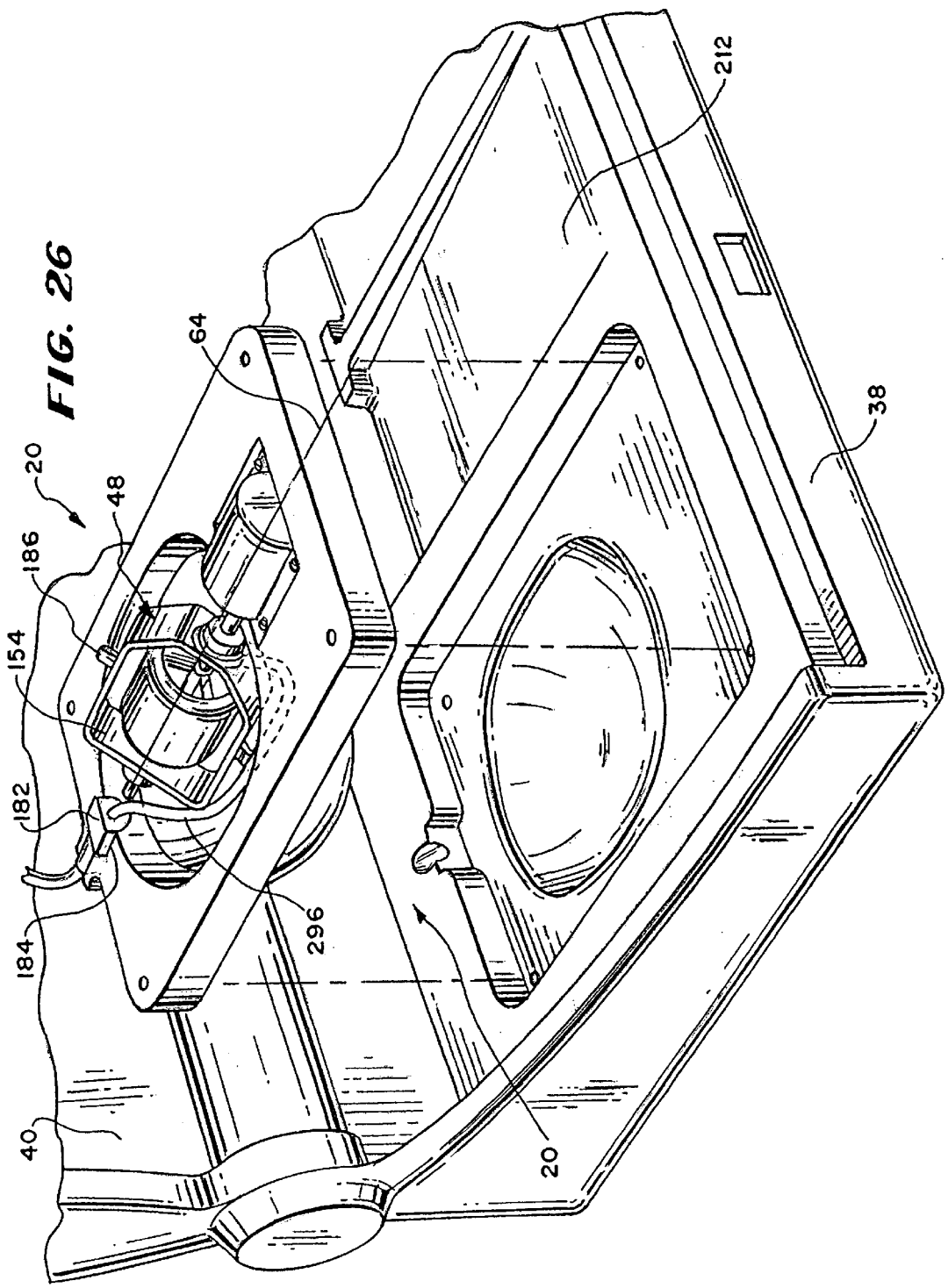
FIG. 26 is an exploded, perspective view of the centrifuge station of the processing device shown in FIG. 1, with the processing container mounted for use.
Figure 27:
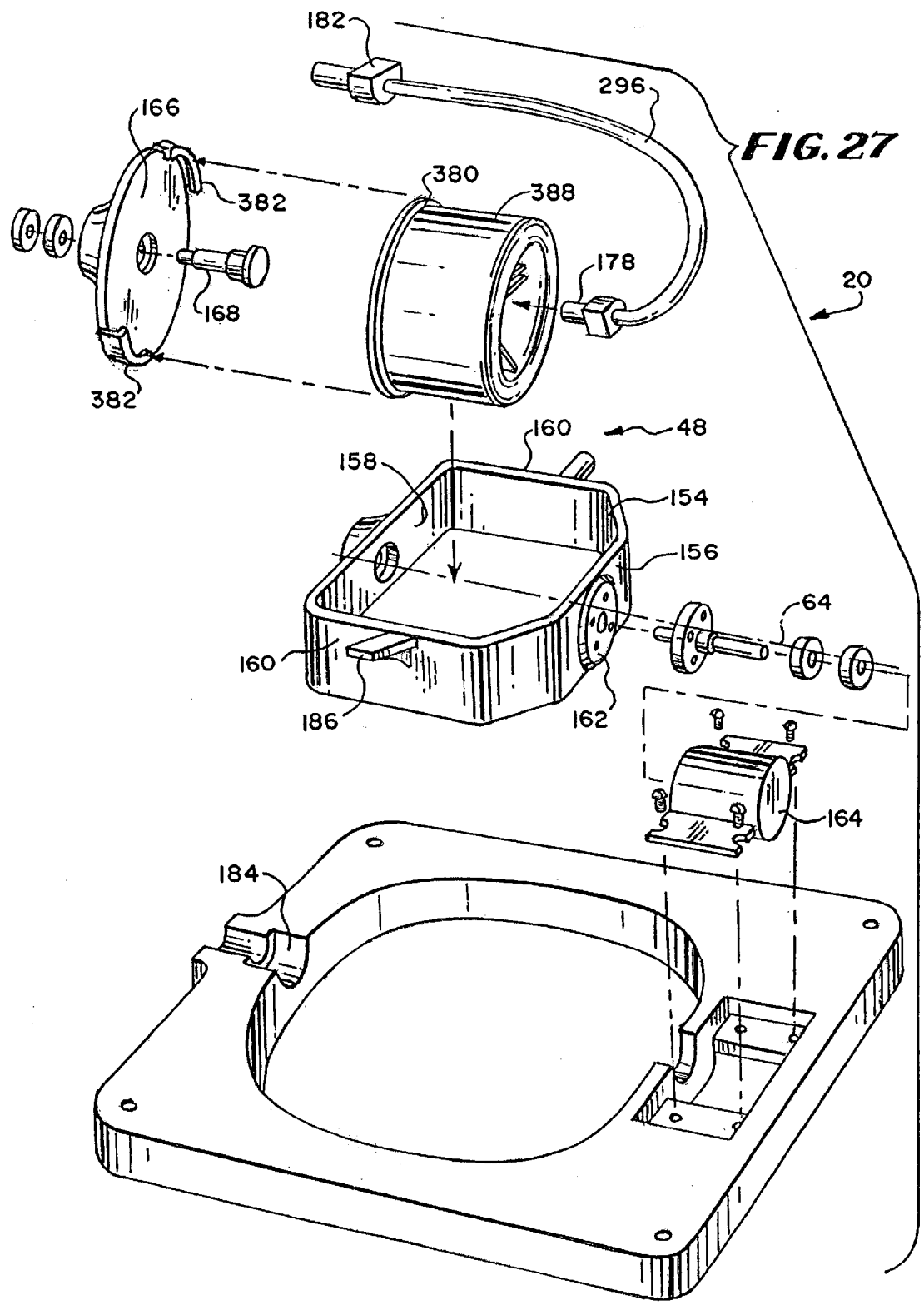
FIG. 27 is a further exploded, perspective view of the centrifuge station and processing container shown in FIG. 26.

The centrifuge station 20 (see FIGS. 26 to 28) includes a centrifuge assembly 48. The centrifuge assembly 48 is constructed to receive and support the molded processing chamber 18 for use.

As illustrated, the centrifuge assembly 48 includes a yoke 154 having bottom, top, and side walls 156, 158, 160. The yoke 154 spins on a bearing element 162 attached to the bottom wall 156. An electric drive motor 164 is coupled via an axle to the bottom wall 156 of the collar 154, to rotate the yoke 154 about an axis 64. In the illustrated embodiment, the axis 64 is tilted about fifteen degrees above the horizontal plane of the base 38, although other angular orientations can be used.

A rotor plate 166 spins within the yoke 154 about its own bearing element 168, which is attached to the top wall 158 of the yoke 154. The rotor plate 166 spins about an axis that is generally aligned with the axis of rotation 64 of the yoke 154.

The top of the processing chamber 18 includes an annular lip 380, to which the lid 150 is secured. Gripping tabs 382 carried on the periphery of the rotor plate 166 make snap-fit engagement with the lip 380, to secure the processing chamber 18 on the rotor plate 166 for rotation.

A sheath 182 on the near end of the umbilicus 296 fits into a bracket 184 in the centrifuge station 20. The bracket 184 holds the near end of the umbilicus 296 in a non-rotating stationary position aligned with the mutually aligned rotational axes 64 of the yoke 154 and rotor plate 166.

An arm 186 protruding from either or both side walls 160 of the yoke 154 contacts the mid portion of the umbilicus 296 during rotation of the yoke 154. Constrained by the bracket 184 at its near end and the chamber 16 at its far end (where the mount 178 is secured inside the receptacle 179), the umbilicus 296 twists about its own axis as it rotates about the yoke axis 64. The twirling of the umbilicus 296 about its axis as it rotates at one omega with the yoke 154 imparts a two omega rotation to the rotor plate 166, and thus to the processing chamber 18 itself.

The relative rotation of the yoke 154 at a one omega rotational speed and the rotor plate 166 at a two omega rotational speed, keeps the umbilicus 296 untwisted, avoiding the need for rotating seals. The illustrated arrangement also allows a single drive motor 164 to impart rotation, through the umbilicus 296, to the mutually rotating yoke 154 and rotor plate 166. Further details of this arrangement are disclosed in Brown et al U.S. Pat. No. 4,120,449, which is incorporated herein by reference.

Blood is introduced into and separated within the processing chamber 18 as it rotates.

Figure 29:
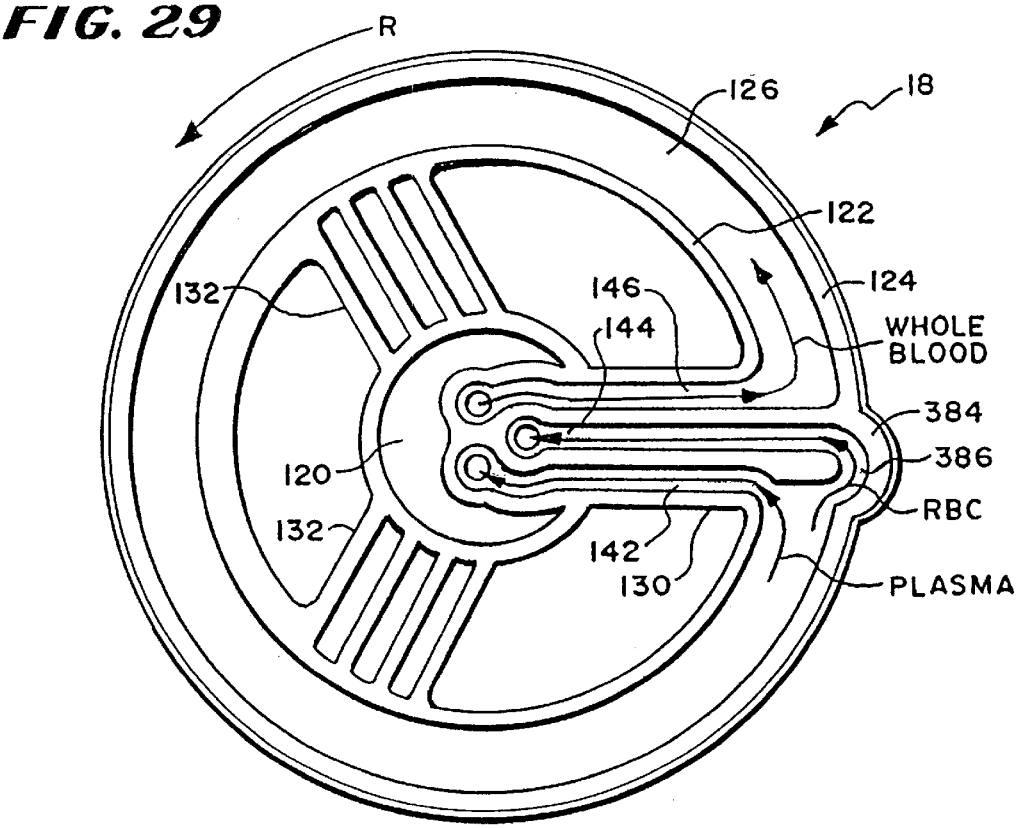
FIG. 29 is a top view of a molded centrifugal blood processing container as shown in FIGS. 21 to 23, showing a flow path arrangement for separating whole blood into plasma and red blood cells.

In one flow arrangement (see FIG. 29), as the processing chamber 18 rotates (arrow R in FIG. 29), the umbilicus 296 conveys whole blood into the channel 126 through the passage 146. The whole blood flows in the channel 126 in the same direction as rotation (which is counterclockwise in FIG. 29). Alternatively, the chamber 18 can be rotated in a direction opposite to the circumferential flow of whole blood, i.e., clockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, a dam 384 projects into the channel 126 toward the high-G wall 124. The dam 384 prevents passage of plasma, while allowing passage of red blood cells into a channel 386 recessed in the high-G wall 124. The channel 386 directs the red blood cells into the umbilicus 296 through the radial passage 144. The plasma constituent is conveyed from the channel 126 through the radial passage 142 into umbilicus 296.

Because the red blood cell exit channel 386 extends outside the high-g wall 124, being spaced further from the rotational axis than the high-g wall, the red blood cell exit channel 386 allows the positioning of the interface between the red blood cells and the buffy coat very close to the high-g wall 124 during blood processing, without spilling the buffy coat into the red blood cell collection passage 144 (creating an over spill condition). The recessed exit channel 386 thereby permits red blood cell yields to be maximized (in a red blood cell collection procedure) or an essentially platelet-free plasma to be collected (in a plasma collection procedure).

Figure 30:
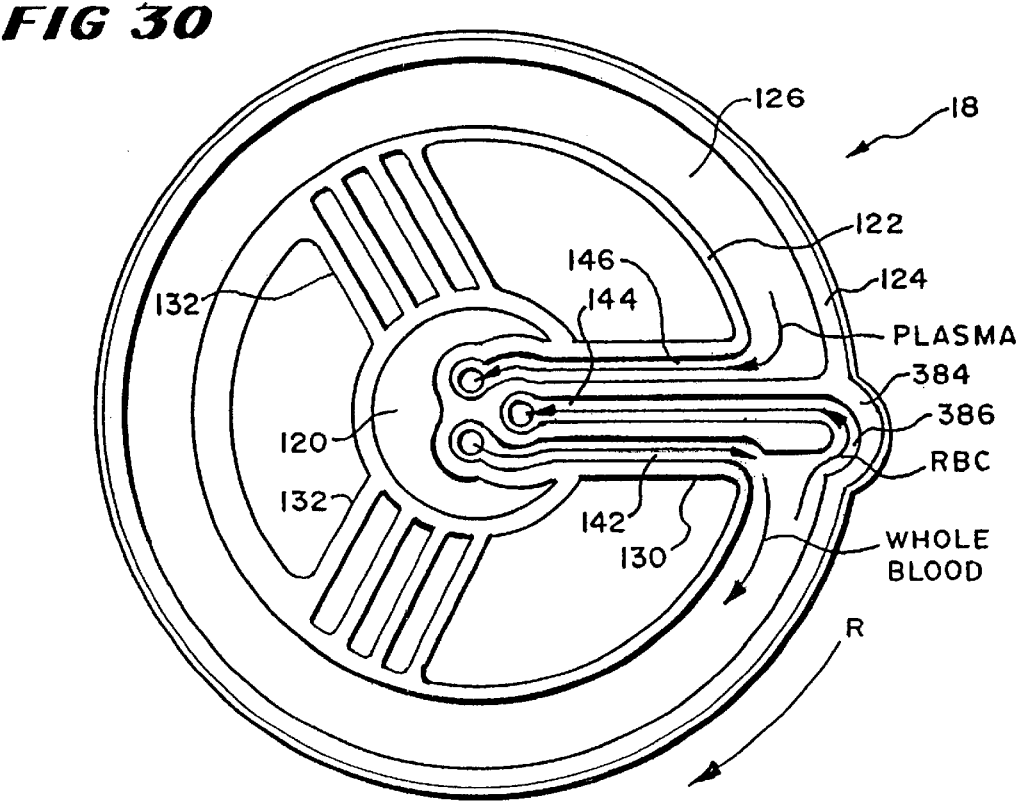
FIGS. 30 to 33 are top views of molded centrifugal blood processing containers as shown in FIGS. 21 to 23, showing other flow path arrangements for separating whole blood into plasma and red blood cells.

In an alternative flow arrangement (see FIG. 30), the umbilicus 296 conveys whole blood into the channel 126 through the passage 142. The processing chamber 18 rotates (arrow R in FIG. 30) in the same direction as whole blood flow (which is clockwise in FIG. 30). Alternatively, the chamber 18 can be rotated in a direction opposite to the circumferential flow of whole blood, i.e., clockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, the dam 384 (previously described) prevents passage of plasma, while allowing passage of red blood cells into the recessed channel 386. The channel 386 directs the red blood cells into the umbilicus 296 through the radial passage 144. The plasma constituent is conveyed from the opposite end of the channel 126 through the radial passage 146 into umbilicus 296.

Figure 31:
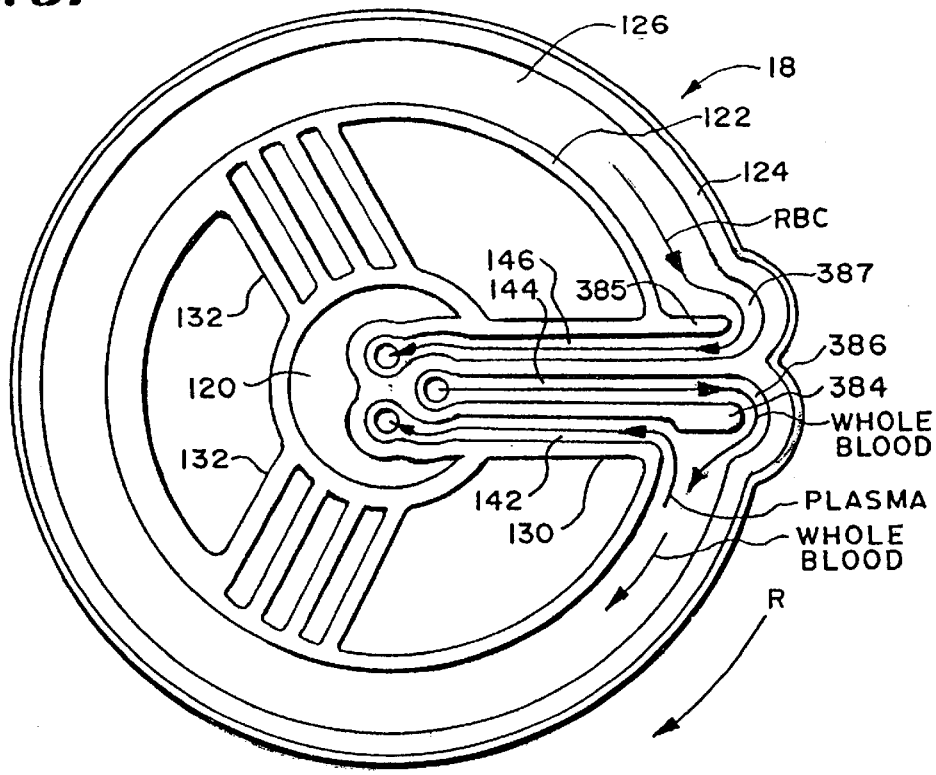

In another alternative flow arrangement (see FIG. 31) the umbilicus 296 conveys whole blood into the channel 126 through the passage 144. The processing chamber 18 is rotated (arrow R in FIG. 31) in the same direction as blood flow (which is clockwise in FIG. 31). Alternatively, the chamber 18 can be rotated in a direction opposite to the circumferential flow of whole blood, i.e., counterclockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, a dam 385 at the opposite end of the channel 126 prevents passage of plasma, while allowing passage of red blood cells into a recessed channel 387. The channel 387 directs the red blood cells into the umbilicus 296 through the radial passage 146. The plasma constituent is conveyed from the other end of the channel 126 through the radial passage 142 into umbilicus 296. In this arrangement, the presence of the dam 384 and the recessed passage 386 (previously described) separates incoming whole blood flow (in passageway 144) from outgoing plasma flow (in passageway 142). This flow arrangement makes possible the collection of platelet-rich plasma, if desired.

Figure 32:
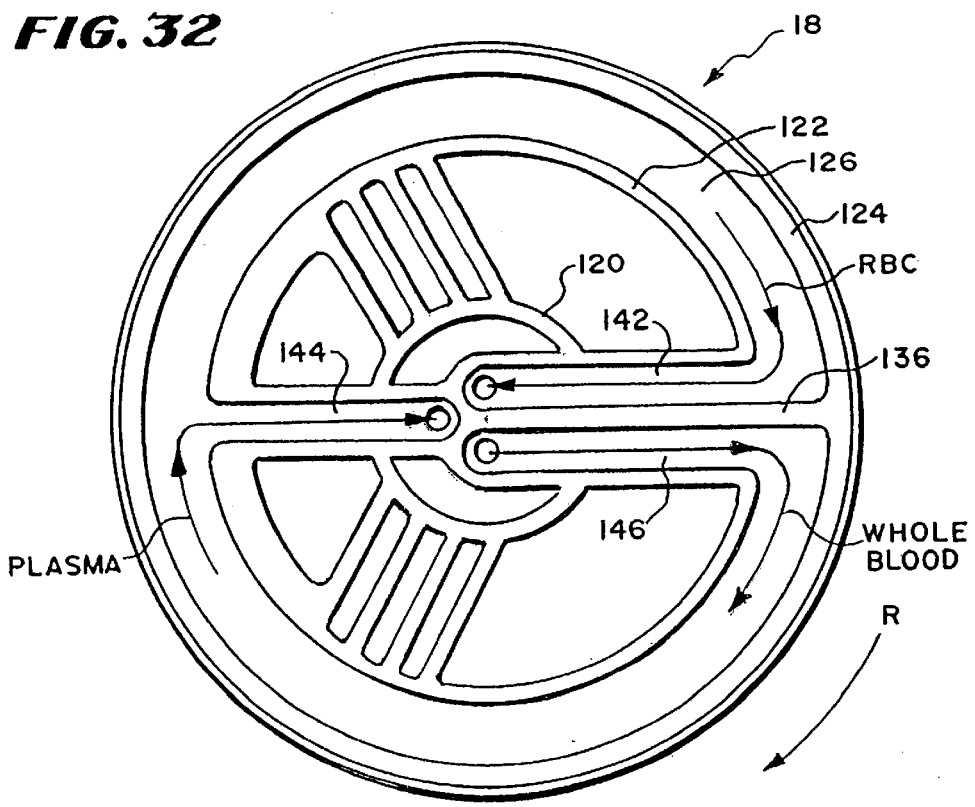

In another alternative flow arrangement (see FIG. 32) the passage 144 extends from the hub 120 into the channel 126 in a direction different than the passages 142 and 146. In this arrangement, the terminus wall 136 separates the passages 142 and 146, and the passage 144 communicates with the channel 126 at a location that lays between the passages 142 and 146. In this arrangement, the umbilicus 296 conveys whole blood into the channel 126 through the passage 146. The processing chamber 18 is rotated (arrow R in FIG. 32) in the same direction as blood flow (which is clockwise in FIG. 32). Alternatively, the chamber 18 can be rotated in a direction opposite to the circumferential flow of whole blood, i.e., counterclockwise. The whole blood separates as a result of centrifugal forces in the manner shown in FIG. 15A. Red blood cells are driven toward the high-G wall 124, while lighter plasma constituent is displaced toward the low-G wall 122.

In this flow pattern, the passage 144 conveys plasma from the channel 126, while the passage 142 conveys red blood cells from the channel 126.

As previously mentioned, in any of the flow patterns shown in FIGS. 28 to 32, the chamber 18 can be rotated in the same direction or in an opposite direction to circumferential flow of whole blood in the channel 126. Blood separation as described will occur in either circumstance. Nevertheless, it has been discovered that, rotating the chamber 18 in the same direction as the flow of whole blood in the channel 126 during separation, appears to minimize disturbances due, e.g., Coriolis effects, resulting in increased separation efficiencies.

EXAMPLE

Figure 28:
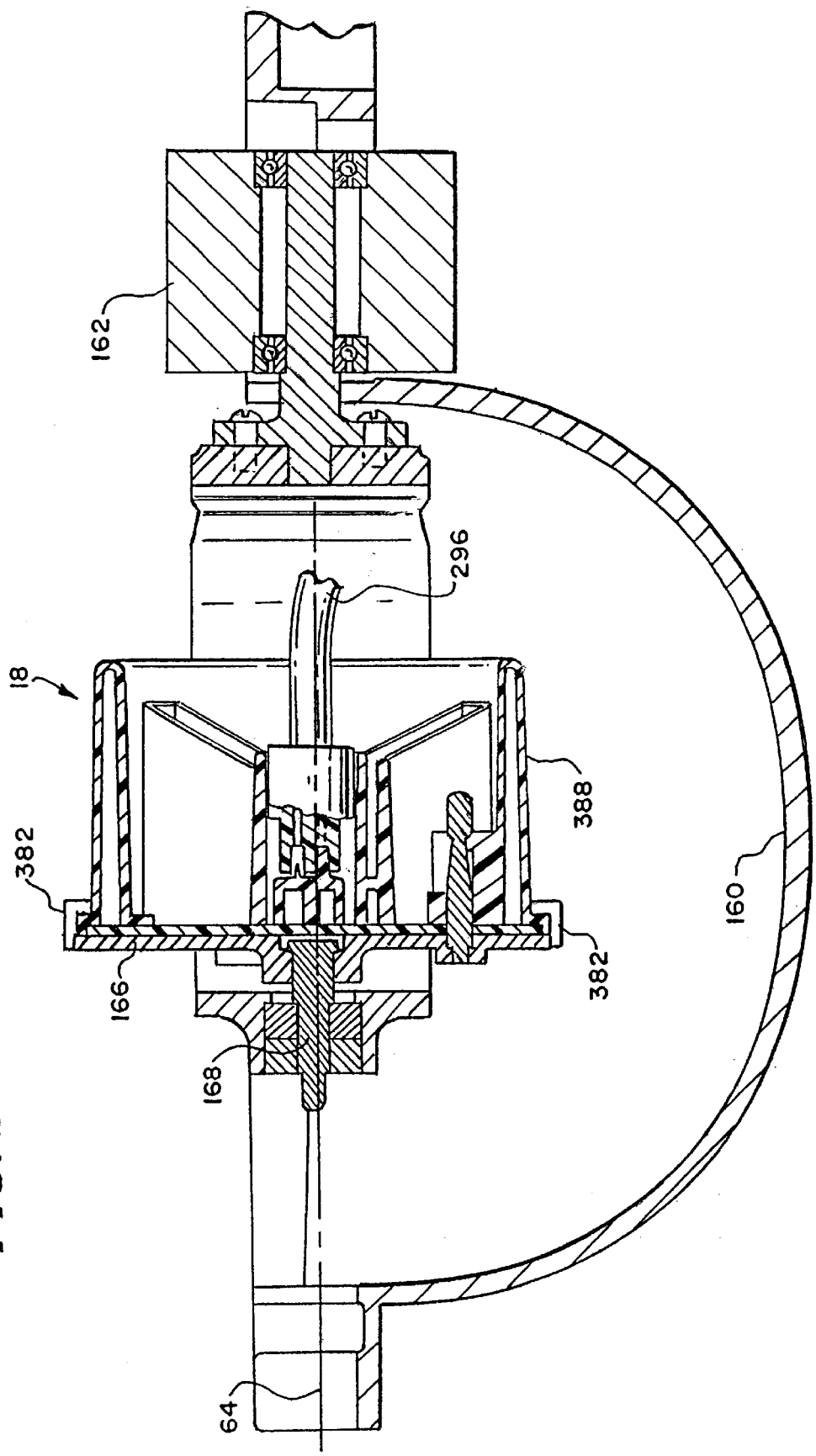
FIG. 28 is a side section view of the centrifuge station of the processing device shown in FIG. 26, with the processing container mounted for use.

Whole blood was separated during various experiments into red blood cells and plasma in processing chambers 18 like that shown in FIG. 28. In one chamber (which will be called Chamber 1), whole blood circumferentially flowed in the channel 126 in the same direction as the chamber 18 was rotated (i.e., the chamber 18 was rotated in a counterclockwise direction). In the other chamber 18 (which will be called Chamber 2), whole blood circumferentially flowed in the channel 126 in a direction opposite to chamber rotation (i.e., the chamber 18 was rotated in a clockwise direction). The average hematocrit for red blood cells collected were measured for various blood volume samples, processed at different combinations of whole blood inlet flow rates and plasma outlet flow rates. The following Tables summarize the results for the various experiments.

TABLE 1

(Flow in the Same Direction as Rotation)

| Number of Blood Samples Processed | Average Whole Blood Hematocrit (%) | Average Hematocrit of Red Blood Cells Collected |
|---|---|---|
| 7 | 45.4 | 74.8 |
| 4 | 40 | 78.8 |

TABLE 2

(Flow in the Opposite Direction as Rotation)

| Number of Blood Samples Processed | Average Whole Blood Hematocrit (%) | Average Hematocrit of Red Blood Cells Collected |
|---|---|---|
| 3 | 43.5 | 55.5 |
| 2 | 42.25 | 58.25 |

Tables 1 and 2 show that, when blood flow in the chamber is in the same direction as rotation, the hematocrit of red blood cells is greater than when blood flow is in the opposite direction. A greater yield of red blood cells also means a greater yield of plasma during the procedure.

Figure 33:
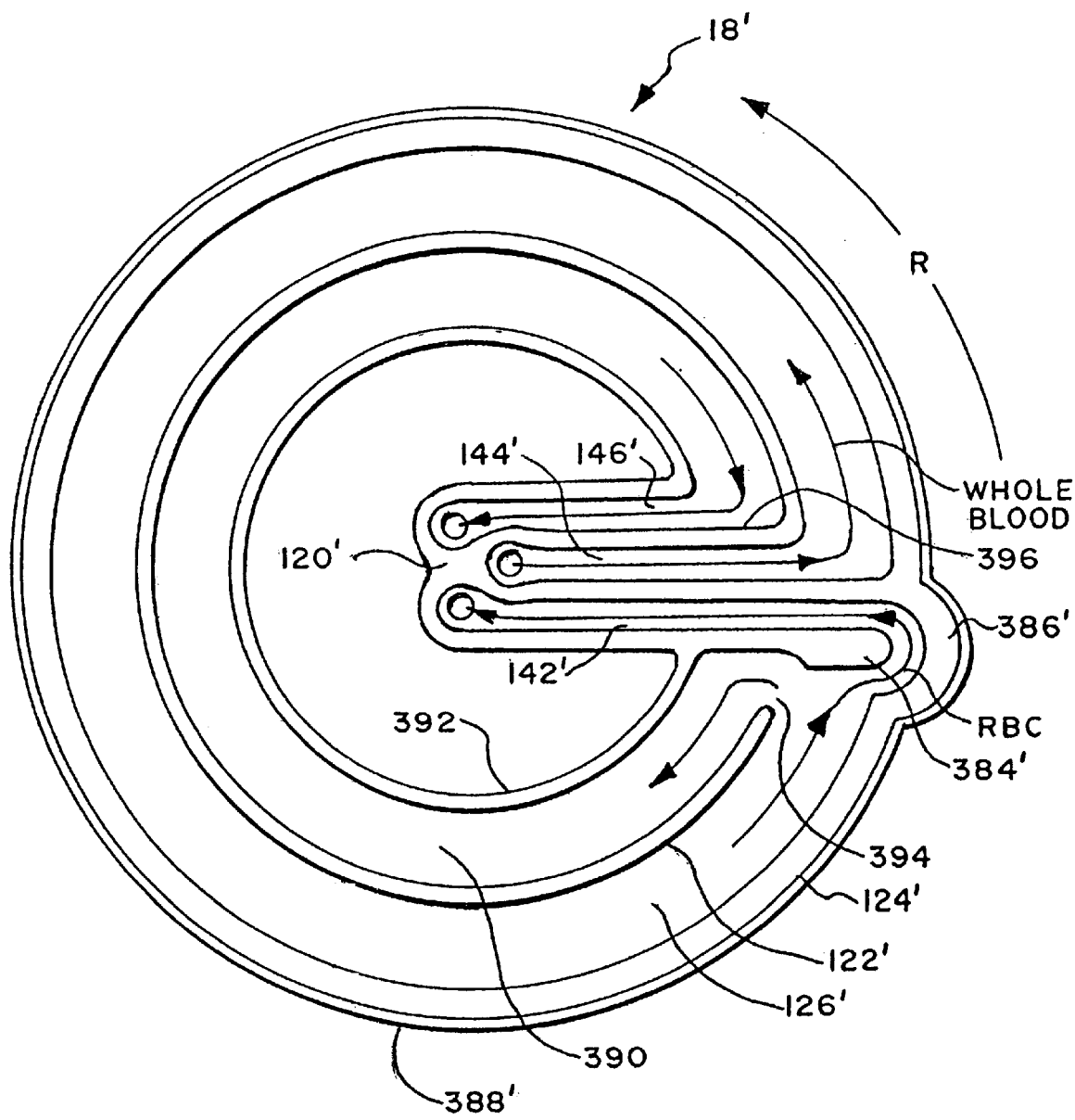

FIG. 33 shows a chamber 18' having a unitary molded base 388' like that shown in FIGS. 21 to 23, but in which two flow paths 126' and 390 are formed. The flow paths 126' and 390 are shown to be concentric, but they need not be. The chamber 18' shares many other structural features in common with the chamber 18 shown in FIG. 23. Common structural features are identified by the same reference number marked with an asterisk.

The base 388' includes a center hub 120' which is surrounded radially by the inside and outside annular walls 122' and 124', defining between them the circumferential blood separation channel 126'. In this embodiment, a second inside annular wall 392 radially surrounds the hub 120'. The second circumferential blood separation channel 390 is defined between the inside annular walls 122' and 392. This construction forms the concentric outside and inside separation channels 126' and 390.

An interruption 394 in the annular wall 122' adjacent to the dam 384' establishes flow communication between the outside channel 126' and the inside channel 390. An interior wall 396 blocks flow communication between the channels 126' and 390 at their opposite ends.

As the processing chamber 18' rotates (arrow R in FIG. 33), the umbilicus 296 conveys whole blood into the outside channel 126' through the passage 144'. The whole blood flows in the channel 126' in the same direction as rotation (which is counterclockwise in FIG. 33). Alternatively, the chamber 18' can be rotated in a direction opposite to the circumferential flow of whole blood, i.e., clockwise. The whole blood separates in the outside channel 126' as a result of centrifugal forces in the manner shown in FIG. 15A. Red blood cells are driven toward the high-G wall 124', while lighter plasma constituent is displaced toward the low-G wall 122'.

As previously described, the dam 384' prevents passage of plasma, while allowing passage of red blood cells into a channel 386' recessed in the high-G wall 124'. The channel 386' directs the red blood cells into the umbilicus 296 through the radial passage 142'. The plasma constituent is conveyed from the channel 126' through the interruption 394 into the inside separation channel 390.

The plasma flows circumferentially flow through the inside channel 390 in a direction opposite to the whole blood in the outside channel 126'. Platelets remaining in the plasma migrate in response to centrifugal forces against the annular wall 124'. The channel 390 directs the plasma constituent to the same end of the chamber 18' where whole blood is initially introduced. The plasma constituent is conveyed from the channel 390 by the passage 146'.

VIII. Other Blood Processing Functions

The many features of the invention have been demonstrated by describing their use in separating whole blood into component parts for storage and blood component therapy. This is because the invention is well adapted for use in carrying out these blood processing procedures. It should be appreciated, however, that the features of the invention equally lend themselves to use in other blood processing procedures.

For example, the systems and methods described, which make use of a programmable cassette in association with a blood processing chamber, can be used for the purpose of washing or salvaging blood cells during surgery, or for the purpose of conducting therapeutic plasma exchange, or in any other procedure where blood is circulated in an extracorporeal path for treatment.

Features of the invention are set forth in the following claims.

We claim:

1. A blood separation chamber comprising
   a formed body, which, in use, rotates about a rotational axis,
   a first interior wall formed on the body, which extends circumferentially about the rotational axis to define a hub,
   inside and outside walls formed on the body, which extend circumferentially about the hub in a spaced apart relationship to define between them a separation channel,
   second interior walls formed on the body, which extend radially from the hub in a spaced apart relationship to define between them at least one passage that communicates with the separation channel to direct blood between the hub and the separation channel,
   a third interior wall formed on the body, which extends partially into the separation chamber from the inside wall toward the outside wall to define a dam that forms a constricted passage along the outside wall, and
   a connector formed on the body to couple exterior tubing to the hub in communication with the passage to convey blood to or from the passage during rotation of the formed body.

2. A blood separation chamber according to claim 1 wherein the second interior walls define an inlet passage to direct blood from the hub into the separation channel and an outlet passage to direct a blood component from the separation channel to the hub.

3. A blood separation chamber according to claim 2 wherein the connector includes first and second couplers to couple exterior tubing in communication with, respectively, the inlet and outlet passages.

4. A blood separation chamber according to claim 1 further including a fourth interior wall formed on the body, which extends across the separation channel to define a terminus in the separation channel.

5. A blood separation chamber according to claim 4 wherein the second interior walls define a first passage communicating with the separation channel on one side of the terminus and a second passage communicating with the separation channel on an opposite side of the terminus.

6. A blood separation chamber according to claim 5 wherein the connector includes first and second couplers to couple exterior tubing in communication with, respectively, the first and second passages.

7. A blood separation chamber according to claim 1 wherein the formed second interior walls define a first passage communicating with the separation channel on one side of the constricted passage and a second passage communicating with the separation channel on another side of the constricted passage.

8. A blood separation chamber according to claim 7 wherein the connector includes first and second couplers to couple exterior tubing in communication with, respectively, the first and second passages.

9. A blood separation chamber according to claim 7 wherein the constricted channel includes a recess in the outside wall radially spaced from the rotational axis farther than adjacent regions of the formed outside wall.

10. A blood separation chamber according to claim 9 wherein the second interior walls define a first passage communicating with the separation channel on one side of the recess and a second passage communicating with the separation channel on another side of the recess.

11. A blood separation chamber according to claim 10 wherein the connector includes first and second couplers to couple exterior tubing in communication with, respectively, the first and second passages.

12. A blood separation chamber according to claim 1 wherein, during rotation of the formed body, blood separates in the separation channel into a blood component, wherein the second interior walls define an inlet passage to direct blood from the hub into the separation channel and an outlet passage to direct the blood component from the separation channel to the hub.

13. A blood separation chamber according to claim 12 wherein the connector includes first and second couplers to couple exterior tubing in communication with, respectively, the inlet and outlet passages.

14. A blood separation chamber according to claim 1 wherein, during rotation of the formed body, blood separates in the separation channel into first and second blood components,
    wherein the second interior walls define an inlet passage to direct blood from the hub into the separation channel, a first outlet passage to direct the first blood component from the separation channel to the hub, and a second outlet passage to direct the second blood component from the separation channel to the hub.

15. A blood separation chamber according to claim 14 wherein the connector includes first, second, and third couplers to couple exterior tubing in communication with, respectively, the inlet and first and second outlet passages.

16. A blood separation chamber according to claim 1 further including an umbilicus that forms a part of the exterior tubing coupled to the connector.

17. A blood separation chamber according to claim 16 wherein the umbilicus carries a connector that mates with the connector formed on the body to establish communication between the exterior tubing and the passage.

18. A blood separation chamber according to claim 1
wherein the inside and outside walls extend circumferentially about the hub in a spaced apart relationship to define between them inner and outer separation channels, and
wherein the second interior walls extend radially from the hub in a spaced apart relationship to define between them at least one passage that communicates with the inner separation channel and at least one passage that communicates with the outer separation channel to direct blood between the hub and the inner and outer separation channels, and
wherein the connector couples exterior tubing to the hub in communication with the passages to convey blood to or from the passage during rotation of the formed body.

19. A blood separation chamber according to claim 18
wherein an interior passage outside the hub provides communication between the inner and outer separation channels.

20. A blood separation chamber according to claim 1
wherein the formed body includes a component to releasably attach the blood separation chamber as a unit to a rotor mechanism for rotation about the rotational axis.

21. A blood separation chamber for use in a blood centrifuge of the type that rotates an umbilicus in concert with a centrifuge rotor to prevent twisting of the umbilicus, the blood separation chamber comprising
a unitary base including formed walls that define a hub, formed inner and outer walls that define between them a separation channel that extends circumferentially about the hub, a formed interior wall that extends partially into the separation chamber from the inside wall toward the outside wall to define a dam that forms a constricted passage along the outside wall, and formed walls that define between them a flow passage that extends radially between the hub and the separation channel, the hub being further formed to enable attachment of the umbilicus to convey blood to and from the separation channel through the hub, and
a lid covering the base and closing the separation channel on a side opposite to the hub, the lid being formed to enable releasable attachment of the blood processing chamber as a unit to the centrifuge rotor for rotation to separate blood in the separation channel.

22. A blood separation chamber according to claim 21 wherein the base comprises an molded body.

23. A blood separation chamber comprising
a formed body, which, in use, rotates about a rotational axis,
a first interior wall formed on the body, which extends circumferentially about the rotational axis to define a hub,
inside and outside walls formed on the body, which extend circumferentially about the hub in a spaced apart relationship to define between them a separation channel in which, during rotation of the formed body, blood separates into first and second blood components,
second interior walls formed on the body, which extend radially from the hub in a spaced apart relationship to define between them an inlet passage to direct blood from the hub into the separation channel, a first outlet passage to direct the first blood component from the separation channel to the hub, and a second outlet passage to direct the second blood component from the separation channel to the hub,
a connector formed on the body to couple exterior tubing to the hub in communication with the inlet and first and second outlet passages to convey blood to or from the inlet and first and second outlet passages during rotation of the formed body, and
an interior wall formed on the body, which extends partially into the separation channel to define a dam in the separation channel.

24. A blood separation chamber according to claim 23
wherein the dam projects from the inside wall toward the outside wall to form a constricted channel along the outside wall.

25. A blood separation chamber according to claim 24
wherein the constricted channel includes a recess in the outside wall radially spaced from the rotational axis farther than adjacent regions of the formed outside wall.

26. A blood separation chamber comprising
a formed body, which, in use, rotates about a rotational axis,
a first interiorwall formed on the body, which extends circumferentially aboutthe rotational axis to define a hub,
inside and outside walls formed on the body, which extend circumferentially about the hub in a spaced apart relationship to define between them inner and outer separation channels,
second interior walls formed on the body, which extend radially from the hub in a spaced apart relationship to define between at least one passage that communicates with the inner separation channel and at least one passage that communicates with the outer separation channel to direct blood between the hub and the inner and outer separation channels, and
a connector formed on the body to couple exterior tubing to the hub in communication with the passage to convey blood to or from the passages during rotation of the formed body.

27. A blood separation chamber according to claim 26
wherein an interior passage outside the hub provides communication between the inner and outer separation channels.

28. A blood separation chamber according to claim 26
wherein the formed body includes a component to releasably attach the blood separation chamber as a unit to a rotor mechanism for rotation about the rotational axis.

29. A blood separation chamber for use in a blood centrifuge of the type that rotates an umbilicus in concert with a centrifuge rotor to prevent twisting of the umbilicus, the blood separation chamber comprising
a unitary base including formed walls that define a hub, formed inner and outer walls which extend circumferentially about the hub in a spaced apart relationship to define between them inner and outer separation channels, and formed walls that extend radially from the hub in a spaced apart relationship to define between them at least one passage that communicates with the inner separation channel and at least one passage that communicates with the outer separation channel to direct blood between the hub and the inner and outer separation channels, and
a lid covering the base and closing the separation channel on a side opposite to the hub, the lid being formed to enable releasable attachment of the blood processing chamber as a unit to the centrifuge rotor for rotation to separate blood in the separation channel.

30. A blood separation chamber according to claim 29 wherein the base comprises an molded body.

\* \* \* \* \*